(12) United States Patent
Nomura et al.

(10) Patent No.: US 8,481,176 B2
(45) Date of Patent: Jul. 9, 2013

(54) OXADIAZOLE DERIVATIVE, AND LIGHT-EMITTING ELEMENT, LIGHT-EMITTING DEVICE, ELECTRONIC DEVICE, AND LIGHTING DEVICE USING OXADIAZOLE DERIVATIVE

(75) Inventors: Hiroko Nomura, Fukuoka (JP); Hiroshi Kadoma, Kanagawa (JP); Takahiro Ushikubo, Kanagawa (JP); Satoko Shitagaki, Kanagawa (JP); Sachiko Kawakami, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 330 days.

(21) Appl. No.: 12/750,354

(22) Filed: Mar. 30, 2010

(65) Prior Publication Data

US 2010/0244673 A1   Sep. 30, 2010

(30) Foreign Application Priority Data

Mar. 31, 2009 (JP) ................................ 2009-084933

(51) Int. Cl.
*H01L 51/54* (2006.01)
*C07D 271/10* (2006.01)

(52) U.S. Cl.
USPC ........... 428/690; 428/917; 313/504; 313/506; 548/145

(58) Field of Classification Search
None
See application file for complete search history.

(56) References Cited

U.S. PATENT DOCUMENTS

2008/0152950 A1* 6/2008 Je et al. ........................ 428/704
2008/0230747 A1   9/2008 Nomura et al.

FOREIGN PATENT DOCUMENTS

| JP | 10-152676 |   | 6/1998 |
| JP | 11-323323 | * | 11/1999 |
| JP | 11-329732 | * | 11/1999 |

OTHER PUBLICATIONS

Macromolecules, (2010), 43(8), pp. 3613-3623.*
Machine translation for JP 11-329732, which was published Nov. 1999.*
Machine-generated translation for JP 10-152676 A (publication date Jun. 1998).*
Tsuji, T. et al, "23.3: Distinguished Paper: Red-Phosphorescent OLEDs Employing Bis(8-Quinolinolato)-Phenolato-Aluminum(III) Complexes as Emission-Layer Hosts," SID Digest '04: SID International Symposium Digest of Technical Papers, vol. 35, 2004, pp. 900-903.

* cited by examiner

*Primary Examiner* — Dawn Garrett
(74) *Attorney, Agent, or Firm* — Husch Blackwell LLP

(57) ABSTRACT

An object is to provide a novel oxadiazole derivative represented by General Formula (G1) as a substance having a high electron-transport property. In the formula, $Ar^1$ represents a substituted or unsubstituted aryl group having 6 to 10 carbon atoms in a ring. When $Ar^1$ has a substituent, the substituent is an alkyl group having 1 to 4 carbon atoms or an aryl group having 6 to 10 carbon atoms in a ring. $Ar^2$ represents a substituted or unsubstituted aryl group having 6 to 10 carbon atoms in a ring or a substituted or unsubstituted heteroaryl group having 4 to 9 carbon atoms. When $Ar^2$ has a substituent, the substituent is an alkyl group having 1 to 4 carbon atoms or an aryl group having 6 to 10 carbon atoms in a ring. $R^1$ and $R^2$ independently represent a hydrogen atom or an alkyl group having 1 to 4 carbon atoms.

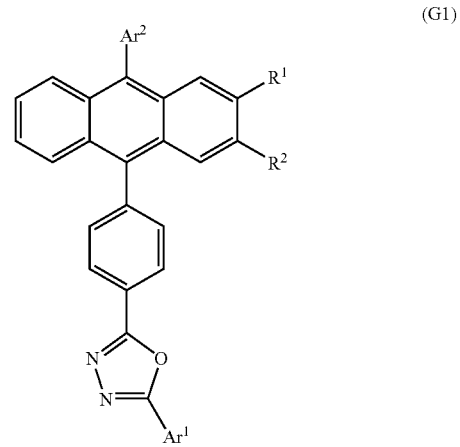

(G1)

20 Claims, 30 Drawing Sheets

OXADIAZOLE DERIVATIVE, AND LIGHT-EMITTING ELEMENT, LIGHT-EMITTING DEVICE, ELECTRONIC DEVICE, AND LIGHTING DEVICE USING OXADIAZOLE DERIVATIVE

BACKGROUND OF THE INVENTION

1. Field of the Invention

The present invention relates to an oxadiazole derivative, and a light-emitting element, a light-emitting device, an electronic device and a lighting device each using the oxadiazole derivative.

2. Description of the Related Art

In recent years, research and development of light-emitting elements using electroluminescence have been extensively conducted. In the basic structure of such a light-emitting element, a layer including a light-emitting substance is interposed between a pair of electrodes. By applying a voltage to this element, light emission can be obtained from the light-emitting substance.

Since this type of light-emitting element is a self-luminous type, it has advantages over a liquid crystal display in that visibility of a pixel is high and that no backlight is needed. Therefore, light-emitting elements are thought to be suitable as flat panel display elements. Further, such a light-emitting element also has advantages in that the element can be formed to be thin and lightweight and that response speed is very high.

Further, since this type of a light-emitting element can be formed to have a film shape, surface light emission can be easily obtained. Therefore, a large-area element using the surface light emission can be formed. This feature is difficult to realize with point light sources typified by a filament lamp and an LED or with linear light sources typified by a fluorescent light. Therefore, such light-emitting elements also have a high utility value as surface light source that can be applied to lighting apparatuses or the like.

Light-emitting elements using electroluminescence are broadly classified according to whether their light-emitting substance is an organic compound or an inorganic compound. When an organic compound is used as a light-emitting substance, by application of a voltage to a light-emitting element, carriers (i.e., electrons and holes) are injected into a layer including the light-emitting organic compound from a pair of electrodes, whereby a current flows. Then, the carriers recombine to place the light-emitting organic compound into an excited state. The light-emitting organic compound returns to a ground state from the excited state, thereby emitting light.

An improvement in characteristics of such light-emitting elements involves a large number of material-dependent problems. To solve them, developments in element structures and materials and the like have been made.

For instance, as an electron-transport material for light-emitting elements, tris(8-quinolinolato)aluminum(III) (abbreviation: Alq) has been widely used (see Non-Patent Document 1). Yet, commercialization of light-emitting elements requires a further reduction in drive voltage. Thus, new materials have been extensively studied to improve element characteristics.

REFERENCE

Patent Document

[Non-Patent Document 1] Taishi TSUJI et al., SID 04 DIGEST, 35, PP. 900-903 (2004)

SUMMARY OF THE INVENTION

An object of one embodiment of the present invention is to provide a novel oxadiazole derivative as a substance having a high electron-transport property. Another object is, by applying a novel oxadiazole derivative to a light-emitting element, to improve its element characteristics. Still another object is to provide a light-emitting device, an electronic device, and a lighting device having low power consumption.

One embodiment of the present invention is an oxadiazole derivative represented by the following General Formula (G1).

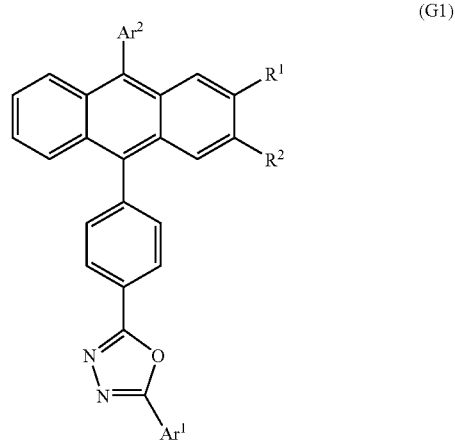

In the formula, $Ar^1$ represents a substituted or unsubstituted aryl group having 6 to 10 carbon atoms in a ring. Note that when $Ar^1$ has a substituent, the substituent is an alkyl group having 1 to 4 carbon atoms or an aryl group having 6 to 10 carbon atoms in a ring. In addition, $Ar^2$ represents a substituted or unsubstituted aryl group having 6 to 10 carbon atoms in a ring or a substituted or unsubstituted heteroaryl group having 4 to 9 carbon atoms. Note that when $Ar^2$ has a substituent, the substituent is an alkyl group having 1 to 4 carbon atoms or an aryl group having 6 to 10 carbon atoms in a ring. In addition, $R^1$ and $R^2$ independently represent a hydrogen atom or an alkyl group having 1 to 4 carbon atoms.

Another embodiment of the present invention is an oxadiazole derivative represented by the following General Formula (G2)."

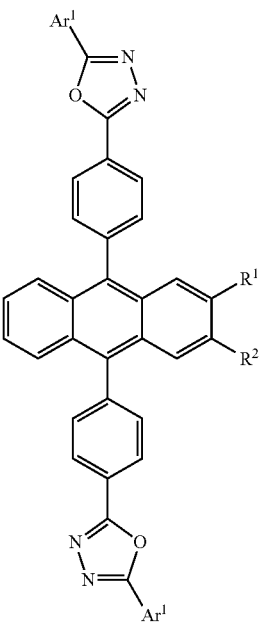

(G2)

In the formula, $Ar^1$ represents a substituted or unsubstituted aryl group having 6 to 10 carbon atoms in a ring. Note that when $Ar^1$ has a substituent, the substituent is an alkyl group having 1 to 4 carbon atoms or an aryl group having 6 to 10 carbon atoms in a ring. In addition, $R^1$ and $R^2$ independently represent a hydrogen atom or an alkyl group having 1 to 4 carbon atoms.

Yet another embodiment of the present invention is an oxadiazole derivative represented by the following General Formula (G3).

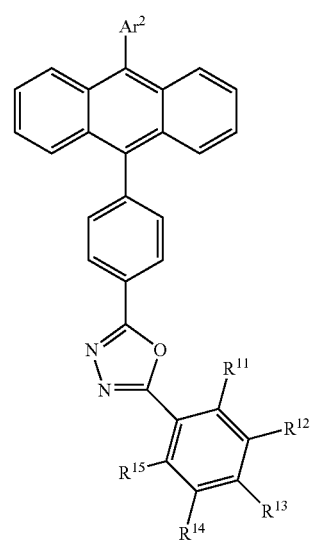

(G3)

In the formula, $Ar^2$ represents a substituted or unsubstituted phenyl group or a substituted or unsubstituted pyridyl group. Note that when $Ar^2$ has a substituent, the substituent is an alkyl group having 1 to 4 carbon atoms or an aryl group having 6 to 10 carbon atoms in a ring. In addition, $R^{11}$ to $R^{15}$ independently represent a hydrogen atom, an alkyl group having 1 to 4 carbon atoms, or an aryl group having 6 to 10 carbon atoms in a ring.

Still another embodiment of the present invention is an oxadiazole derivative represented by the following General Formula (G4).

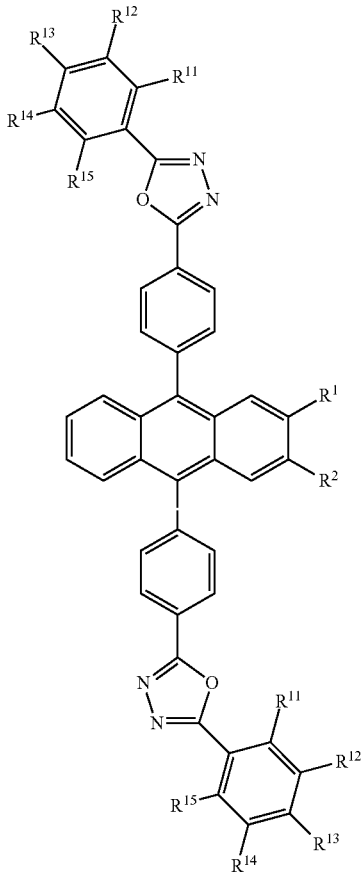

(G4)

In the formula, $R^{11}$ to $R^{15}$ independently represent a hydrogen atom, an alkyl group having 1 to 4 carbon atoms, or an aryl group having 6 to 10 carbon atoms in a ring, and $R^1$ and $R^2$ independently represent a hydrogen atom or an alkyl group having 1 to 4 carbon atoms.

Note that the above oxadiazole derivatives which are embodiments of the present invention have an electron-transport property. Thus, another embodiment of the present invention is a light-emitting element having an EL layer between a pair of electrodes which includes any of the above-described oxadiazole derivatives.

Further, another embodiment of the present invention is a light-emitting device formed using the above-described light-emitting element. Note that the term light-emitting device in this specification includes an image display device, a light-emitting device, a light source, and the like. Further, the category of the light-emitting device includes: a module in which a connector such as a flexible printed circuit (FPC), a tape automated bonding (TAB) tape, or a tape carrier package (TCP) is attached to a light-emitting device, a module in which the top of a TAB tape, or a TCP is provided with a printed wire board, and a module in which an integrated circuit (IC) is directly mounted on a light-emitting element by a chip on glass (COG) technique.

Another embodiment of the present invention is an electronic device formed using the above light-emitting device. Yet another embodiment of the present invention is a lighting device formed using the above light-emitting device.

Embodiments of the present invention can provide the oxadiazole derivatives having a high electron-transport property. Further, by use of any of the oxadiazole derivatives which are embodiments of the present invention, a light-emitting element having high current efficiency can be fainted. Also, by use of the above light-emitting element which is one embodiment of the present invention, a light-emitting device, an electronic device, and a lighting device having low power consumption and low drive voltage can be obtained.

DETAILED DESCRIPTION OF THE INVENTION

Figure 1:
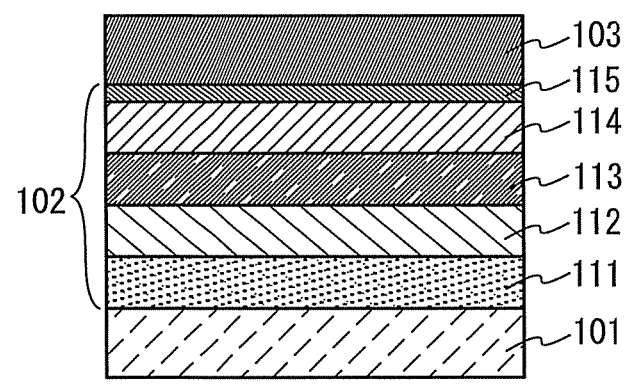
FIG. 1 illustrates a light-emitting element which is one embodiment of the present invention.

Hereinafter, embodiments of the present invention will be described using the accompanying drawings. Note that the present invention is not limited to the description below, and the modes and details of the present invention can be easily modified in various ways by those skilled in the art without departing from the spirit and scope of the present invention. Therefore, the embodiments of the present invention should not be construed as being limited to the description of the embodiment modes and examples below.

Embodiment 1

In Embodiment 1, the oxadiazole derivatives which are embodiments of the present invention will be described.

An oxadiazole derivative which is one embodiment of the present invention is the oxadiazole derivative represented by General Formula (G1).

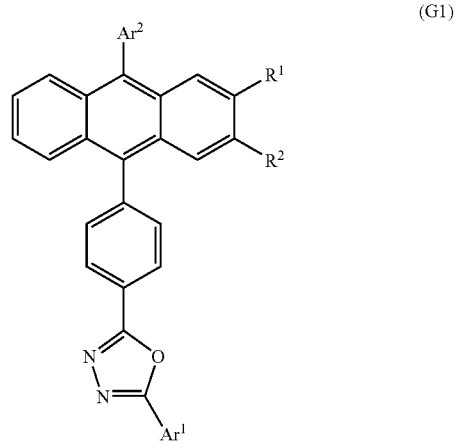

(G1)

In the formula, $Ar^1$ represents a substituted or unsubstituted aryl group having 6 to 10 carbon atoms in a ring. Note that when $Ar^1$ has a substituent, the substituent is an alkyl group having 1 to 4 carbon atoms or an aryl group having 6 to 10 carbon atoms in a ring. In addition, $Ar^2$ represents a substituted or unsubstituted aryl group having 6 to 10 carbon atoms in a ring or a substituted or unsubstituted heteroaryl group having 4 to 9 carbon atoms. Note that when $Ar^2$ has a substituent, the substituent is an alkyl group having 1 to 4 carbon atoms or an aryl group having 6 to 10 carbon atoms in a ring. In addition, $R^1$ and $R^2$ independently represent a hydrogen atom or an alkyl group having 1 to 4 carbon atoms.

Note that the number of carbon atoms of the aryl group described in this specification represents the number of carbon atoms which form a ring of the main skeleton, and is exclusive of the number of carbon atoms of a substituent bonded to carbon atoms which form a ring of the main skeleton.

An oxadiazole derivative which is one embodiment of the present invention is the oxadiazole derivative represented by General Formula (G2).

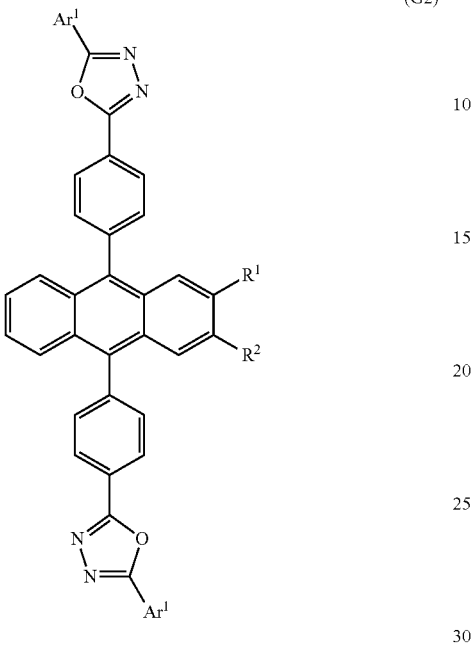

(G2)

In the formula, $Ar^1$ represents a substituted or unsubstituted aryl group having 6 to 10 carbon atoms in a ring. Note that when $Ar^1$ has a substituent, the substituent is an alkyl group having 1 to 4 carbon atoms or an aryl group having 6 to 10 carbon atoms in a ring. In addition, $R^1$ and $R^2$ independently represent a hydrogen atom or an alkyl group having 1 to 4 carbon atoms.

An oxadiazole derivative which is one embodiment of the present invention is the oxadiazole derivative represented by General Formula (G3).

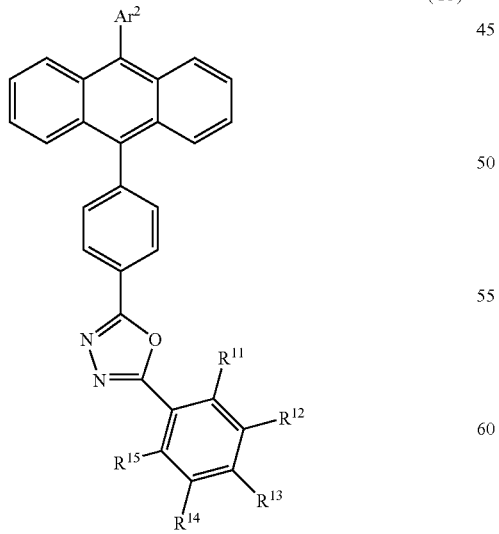

(G3)

In the formula, $Ar^2$ represents a substituted or unsubstituted phenyl group or a substituted or unsubstituted pyridyl group. Note that when $Ar^2$ has a substituent, the substituent is an alkyl group having 1 to 4 carbon atoms or an aryl group having 6 to 10 carbon atoms in a ring. In addition, $R^{11}$ to $R^{15}$ independently represent a hydrogen atom, an alkyl group having 1 to 4 carbon atoms, or an aryl group having 6 to 10 carbon atoms in a ring.

An oxadiazole derivative which is one embodiment of the present invention is the oxadiazole derivative represented by General Formula (G4).

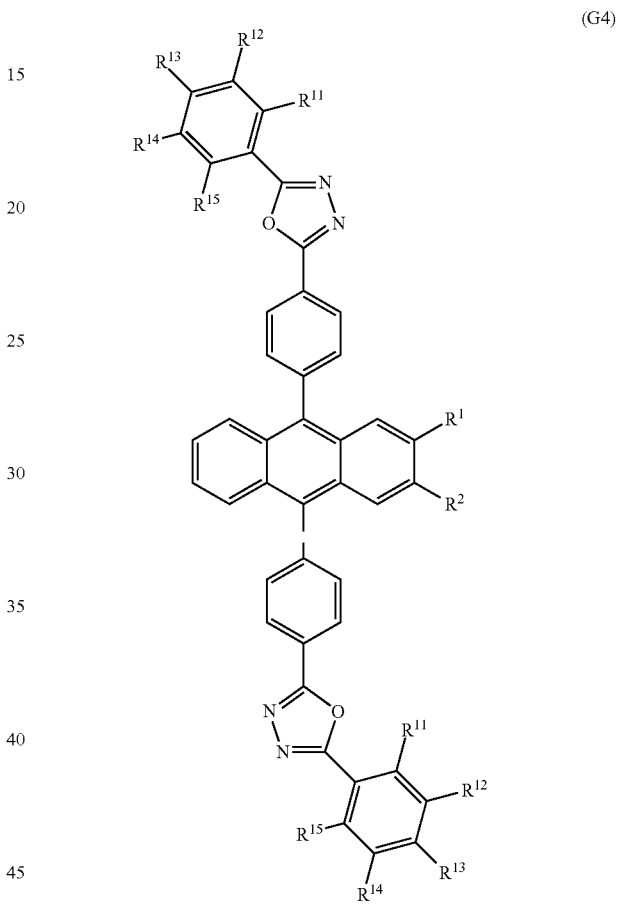

(G4)

In the formula, $R^{11}$ to $R^{15}$ independently represent a hydrogen atom, an alkyl group having 1 to 4 carbon atoms, or an aryl group having 6 to 10 carbon atoms in a ring, and $R^1$ and $R^2$ independently represent a hydrogen atom or an alkyl group having 1 to 4 carbon atoms.

As examples of specific structures of $Ar^1$ in the above General Formulas (G1) and (G2), there are substituents represented by Structural Formulas (1-1) to (1-17).

(1-1)

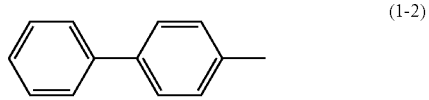

(1-2)

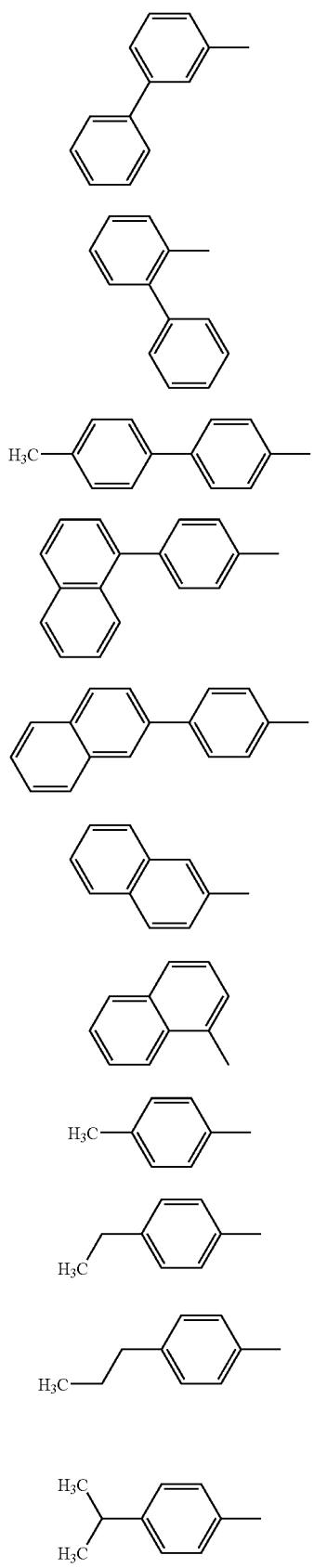
(1-3)
(1-4)
(1-5)
(1-6)
(1-7)
(1-8)
(1-9)
(1-10)
(1-11)
(1-12)
(1-13)
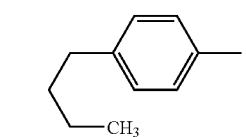
(1-14)
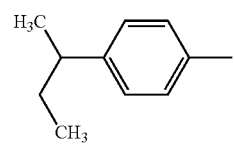
(1-15)
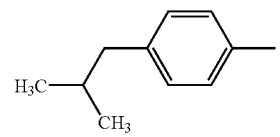
(1-16)
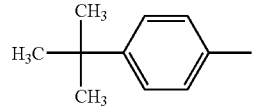
(1-17)
Further, as examples of specific structures of $Ar^2$ in General Formulas (G1) and (G3), there are substituents represented by Structural Formulas (2-1) to (2-17) and (3-1) to (3-36).
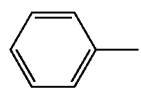
(2-1)
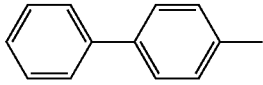
(2-2)
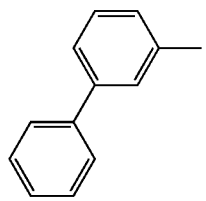
(2-3)
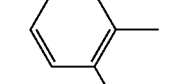
(2-4)
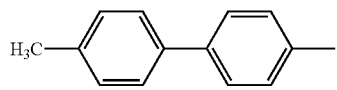
(2-5)
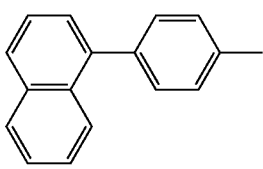
(2-6)

(2-7) 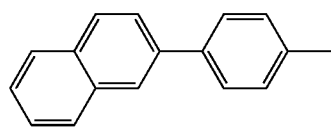
(2-8) 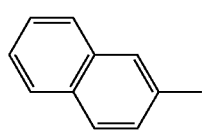
(2-9) 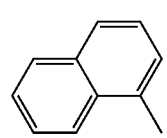
(2-10) 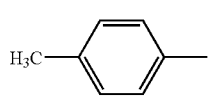
(2-11) 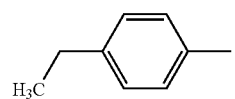
(2-12) 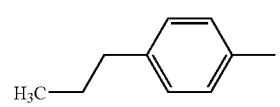
(2-13) 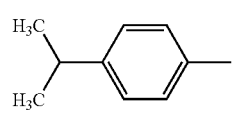
(2-14) 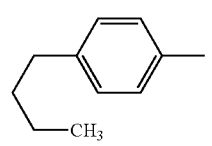
(2-15) 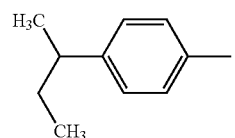
(2-16) 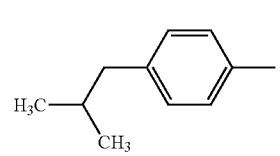
(2-17) 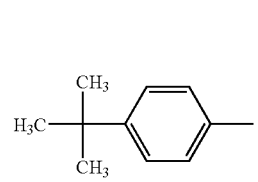
(3-1) 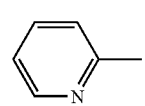
(3-2) 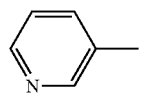
(3-3) 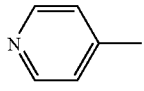
(3-4) 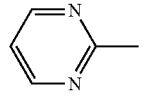
(3-5) 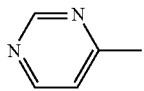
(3-6) 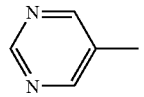
(3-7) 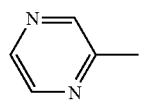
(3-8) 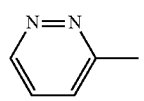
(3-9) 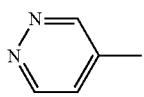
(3-10) 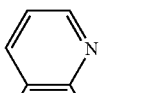
(3-11) 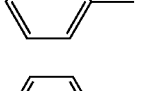
(3-12) 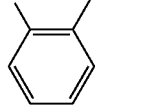
(3-13) 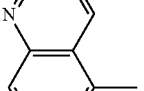
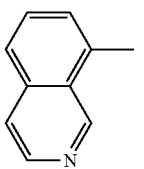

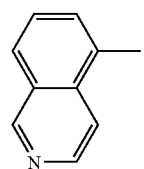 (3-14)
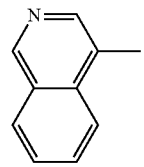 (3-15)
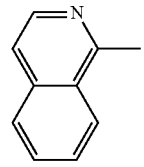 (3-16)
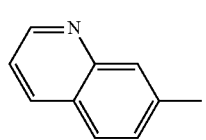 (3-17)
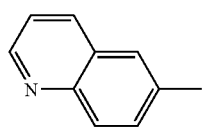 (3-18)
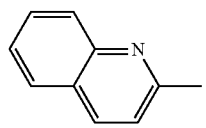 (3-19)
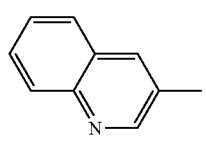 (3-20)
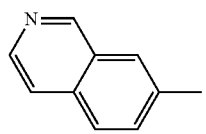 (3-21)
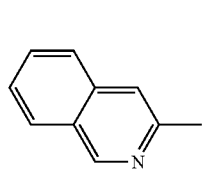 (3-22)
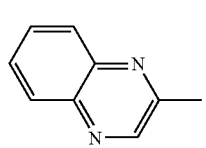 (3-23)
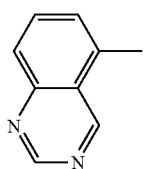 (3-24)
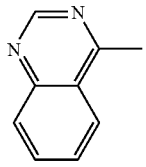 (3-25)
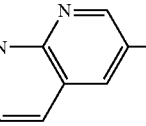 (3-26)
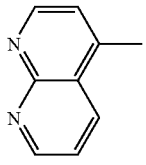 (3-27)
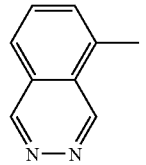 (3-28)
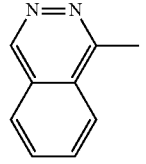 (3-29)
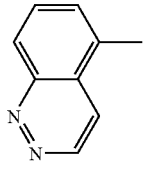 (3-30)
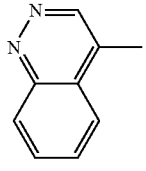 (3-31)
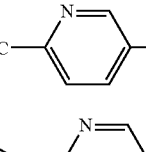 (3-32)
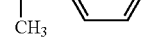 (3-33)

-continued
(3-34)
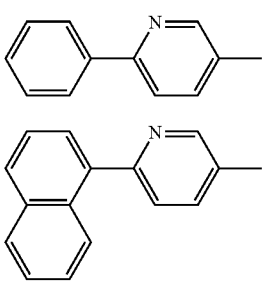
(3-35)
-continued
(3-36)
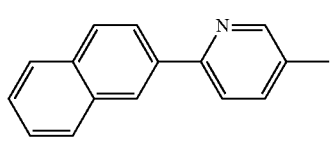
Note that specific examples of the oxadiazole derivatives represented by the above General Formulas (G1) to (G4) which are embodiments of the present invention include, but are not limited to, oxadiazole derivatives represented by Structural Formulas (100) to (173).
(100)
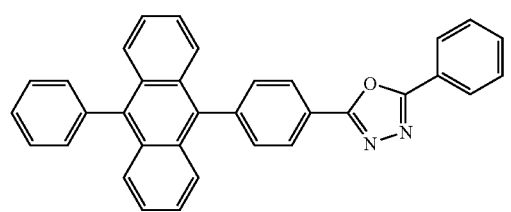
(101)
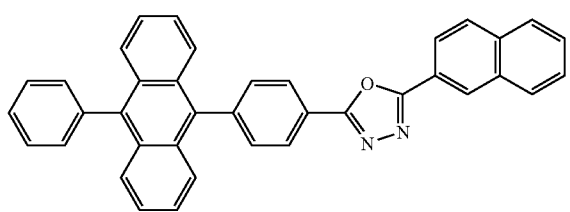
(102)
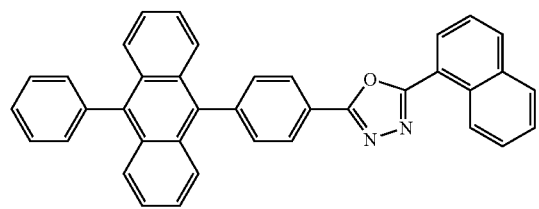
(103)
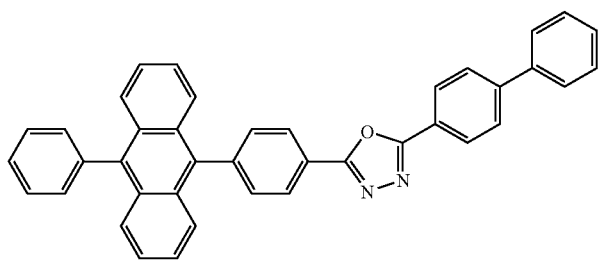
(104)
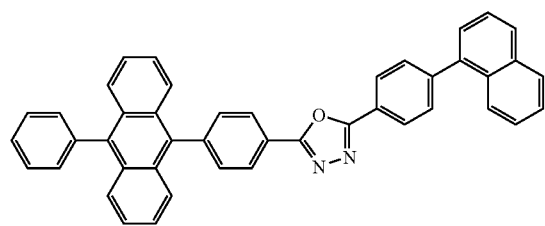
(105)
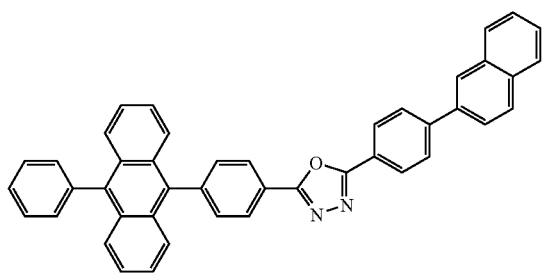
(106)
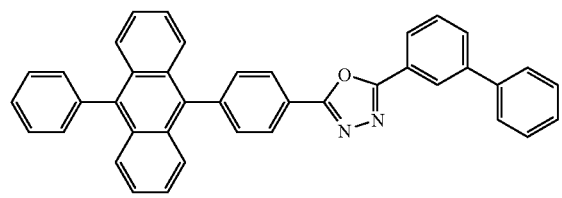
(107)
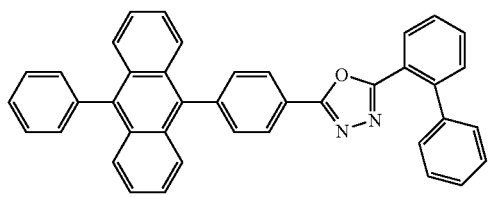
(108)
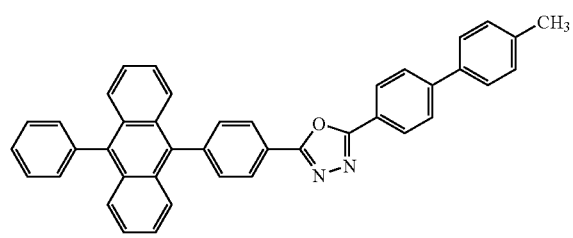
(109)
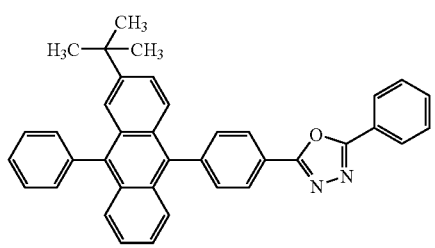

-continued
(110)
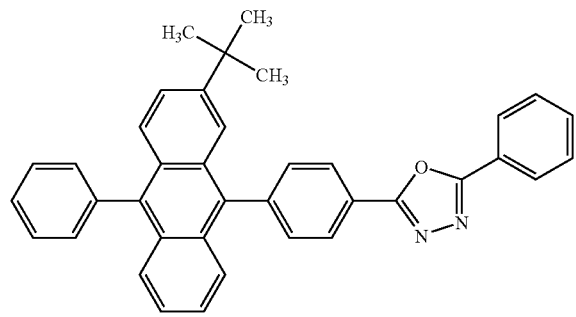
(111)
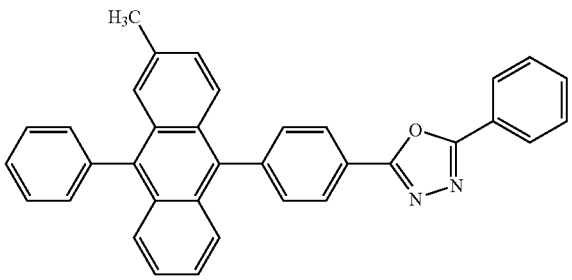
(112)
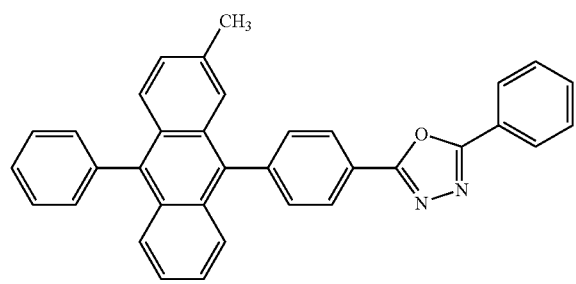
(113)
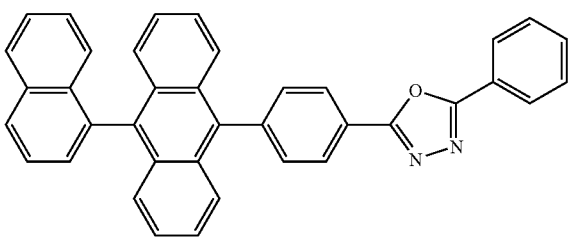
(114)
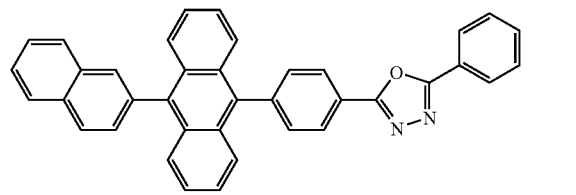
(115)
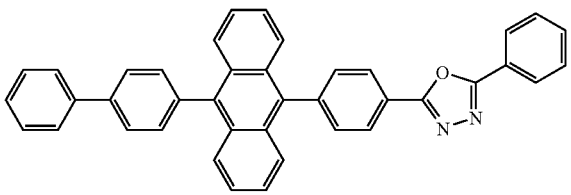
(116)
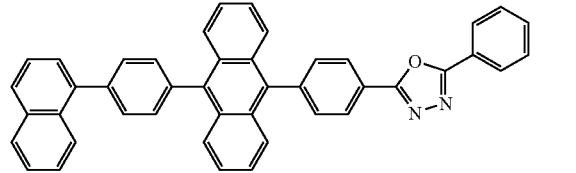
(117)
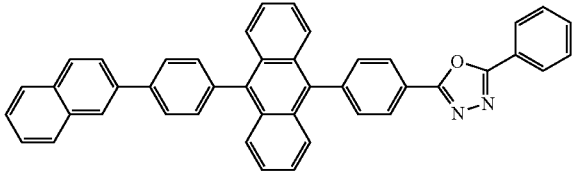
(118)
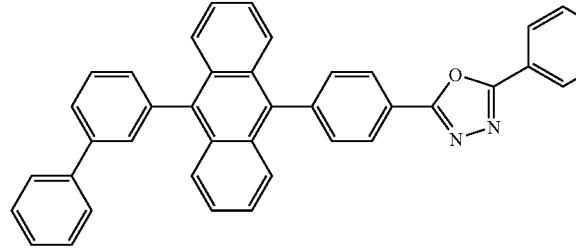
(119)
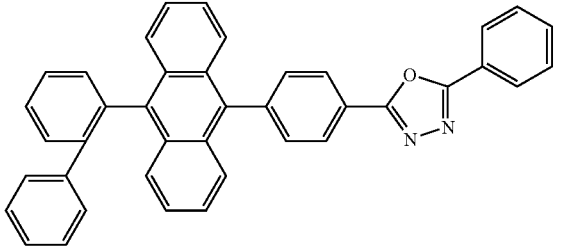
(120)
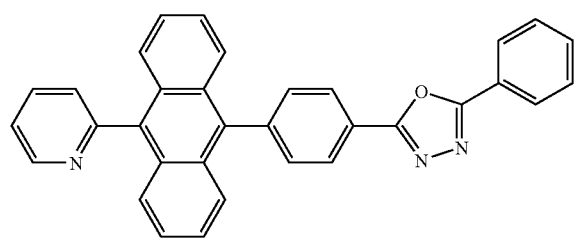
(121)
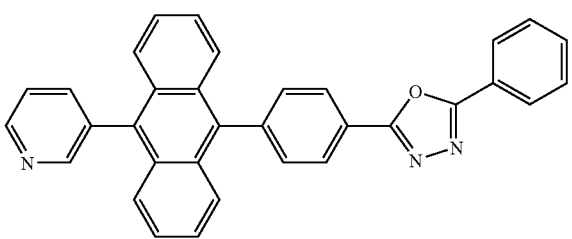

-continued
(122)
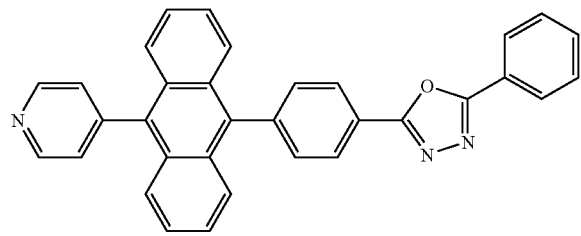
(123)
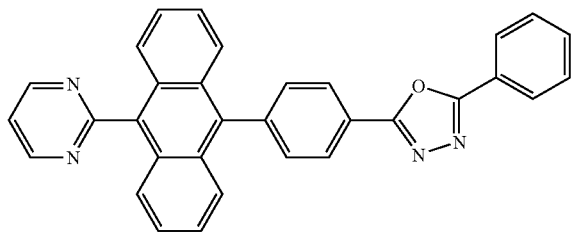
(124)
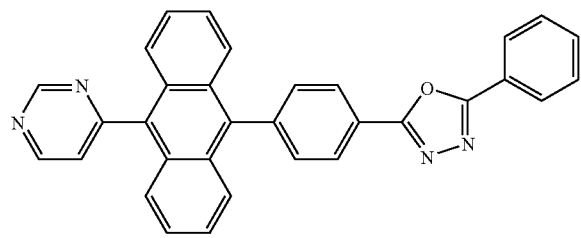
(125)
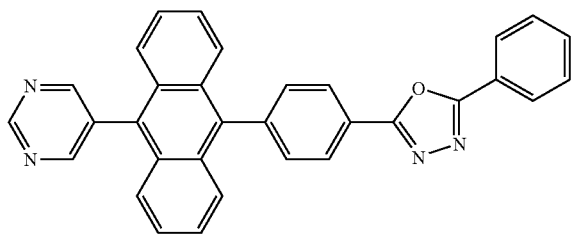
(126)
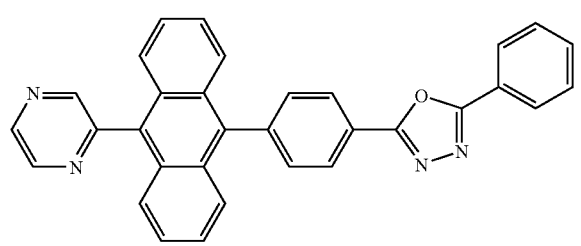
(127)
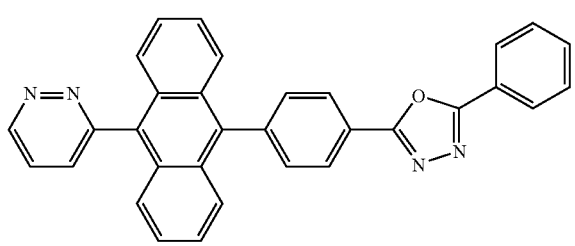
(128)
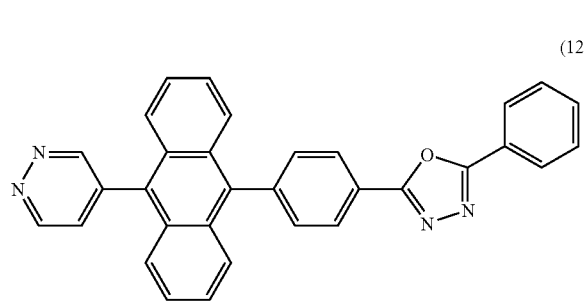
(129)
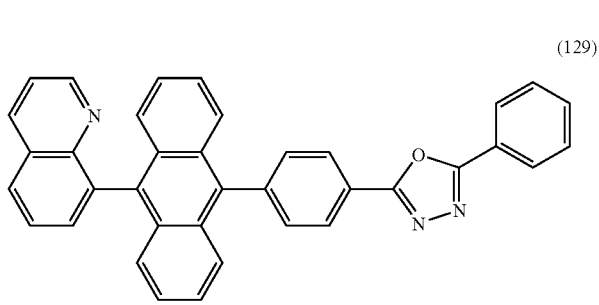
(130)
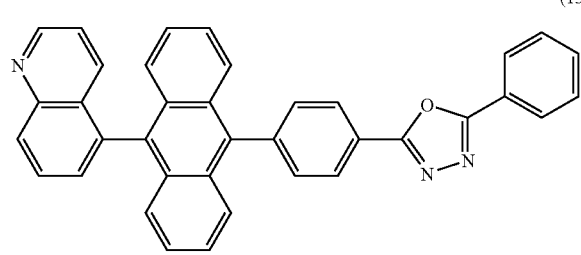
(131)
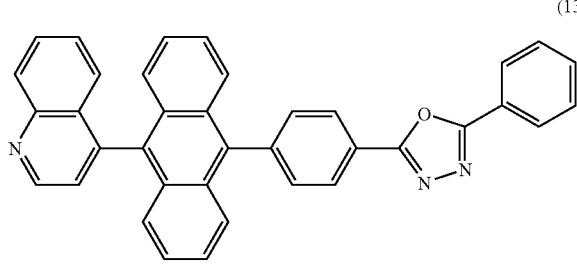
(132)
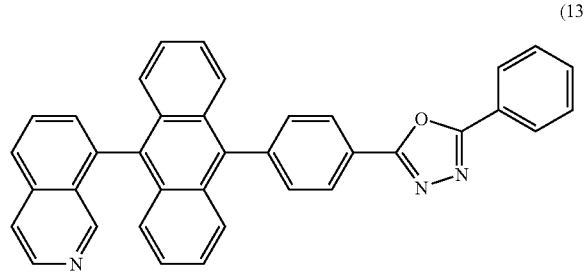
(133)
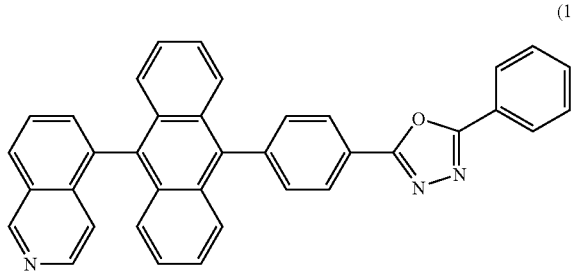

-continued
(134)
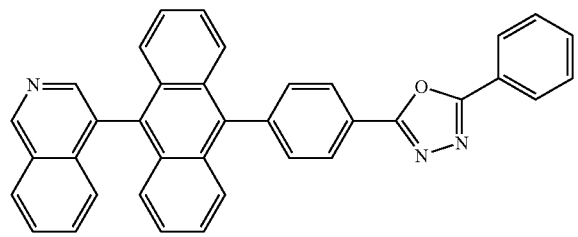
(135)
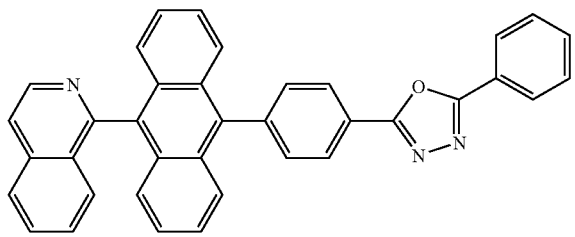
(136)
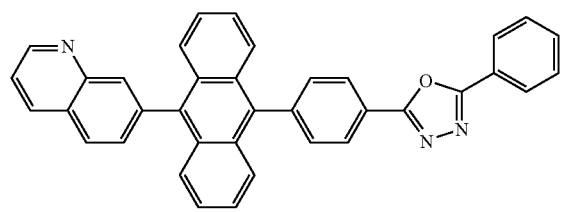
(137)
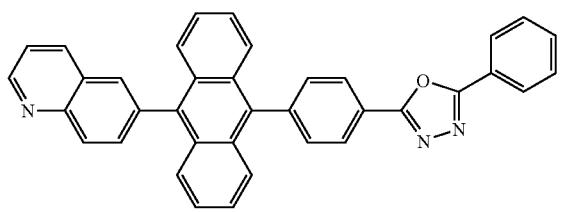
(138)
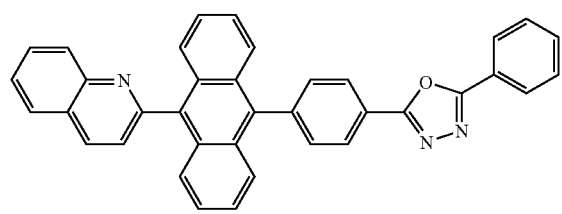
(139)
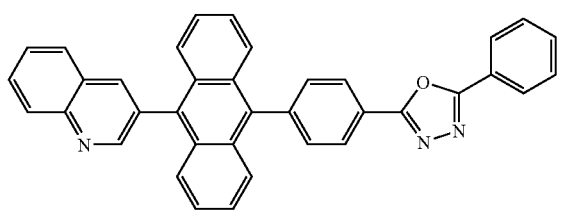
(140)
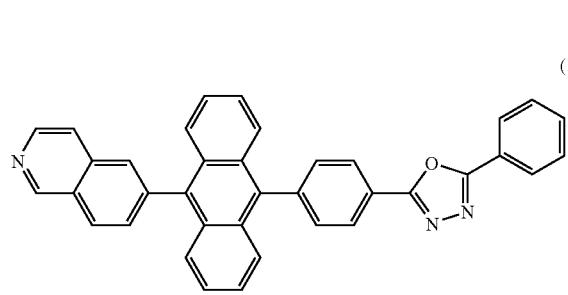
(141)
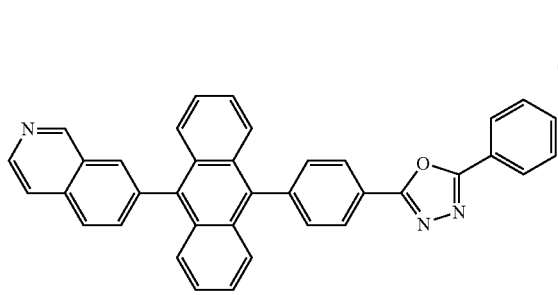
(142)
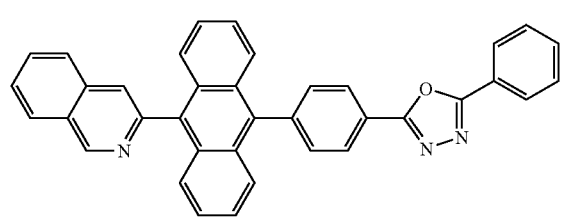
(143)
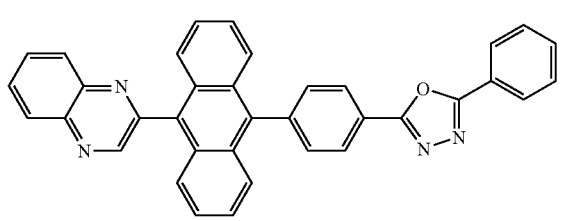
(144)
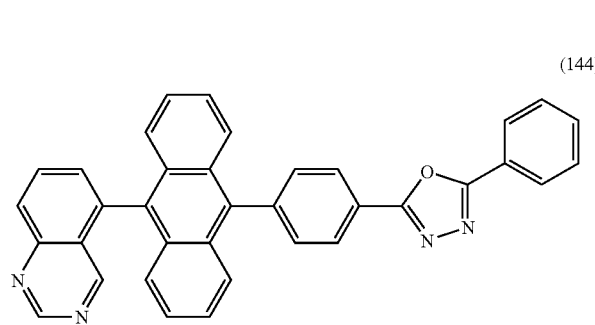
(145)
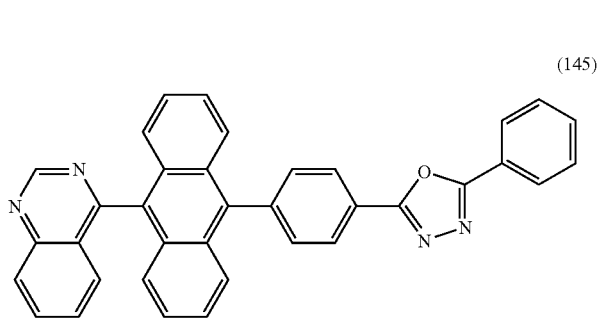

-continued
(146) 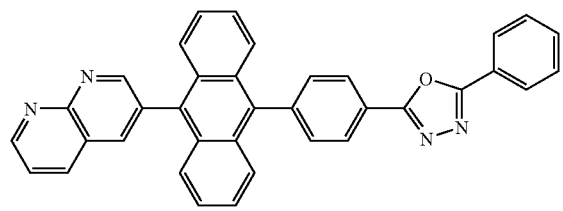
(147) 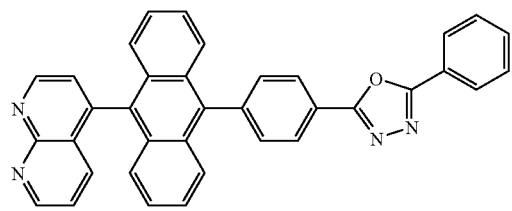
(148) 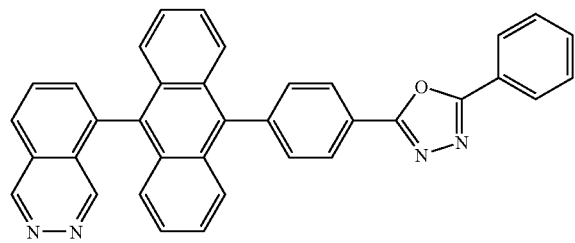
(149) 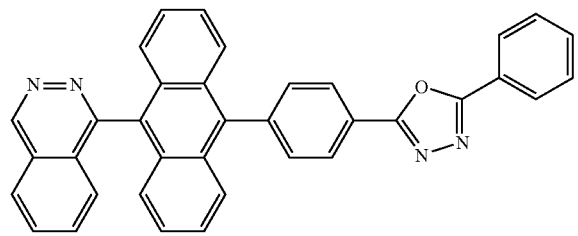
(150) 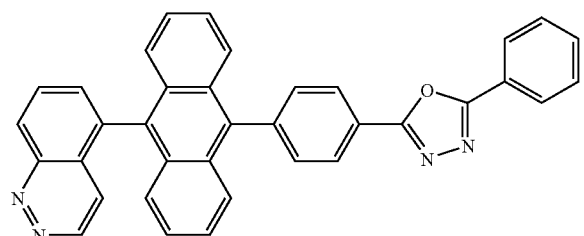
(151) 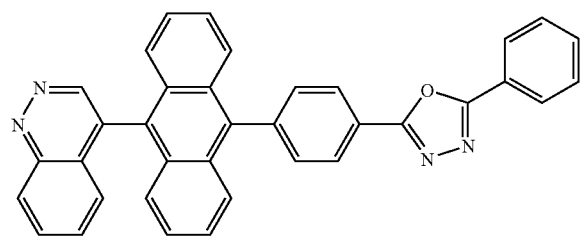
(152) 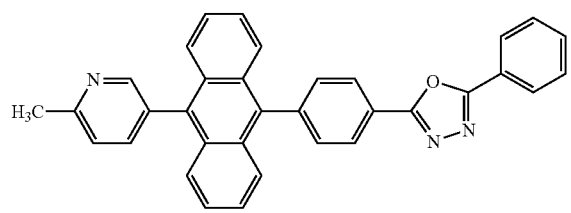
(153) 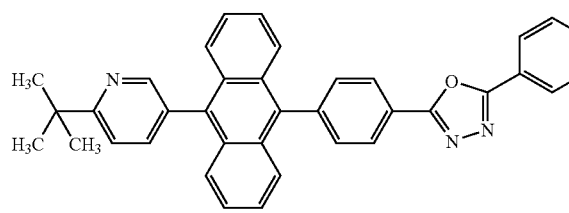
(154) 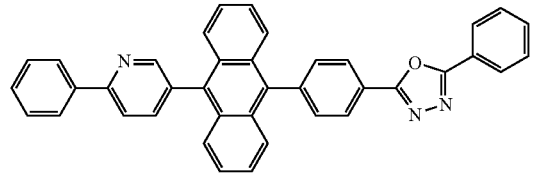
(155) 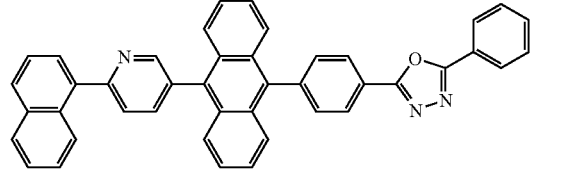
(156) 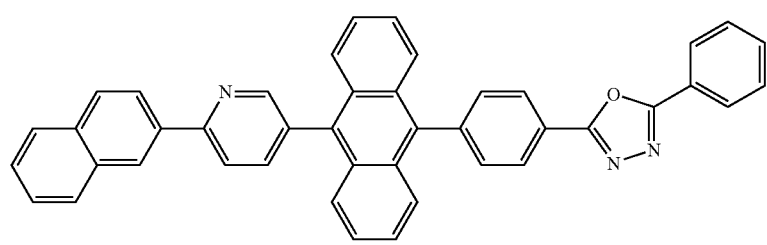
(157) 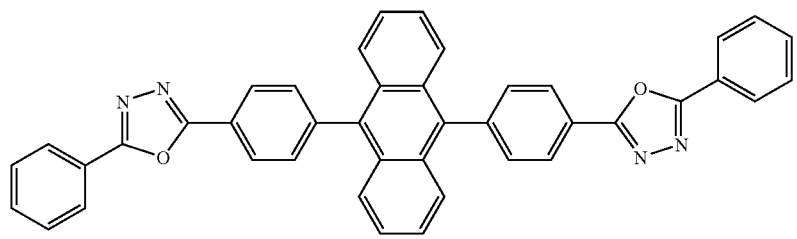

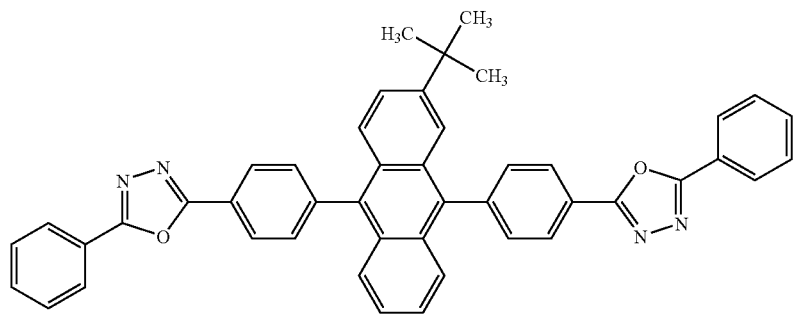
(158)
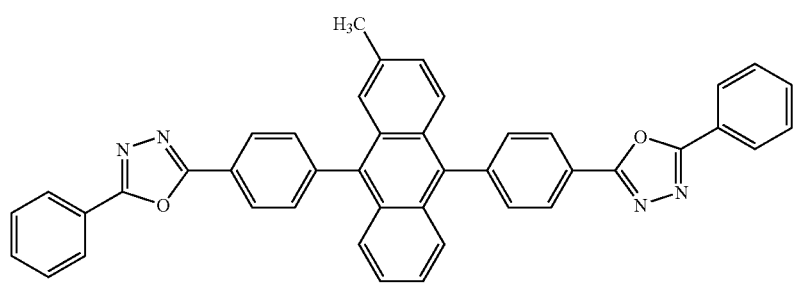
(159)
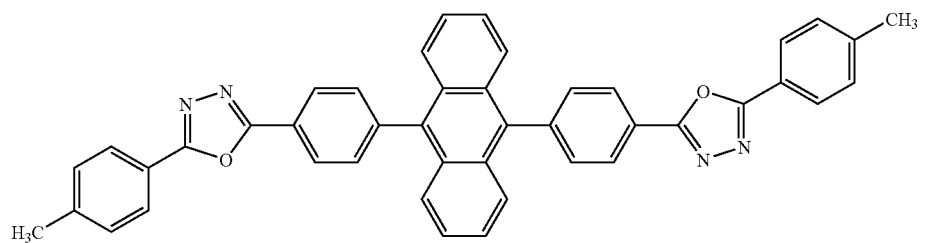
(160)
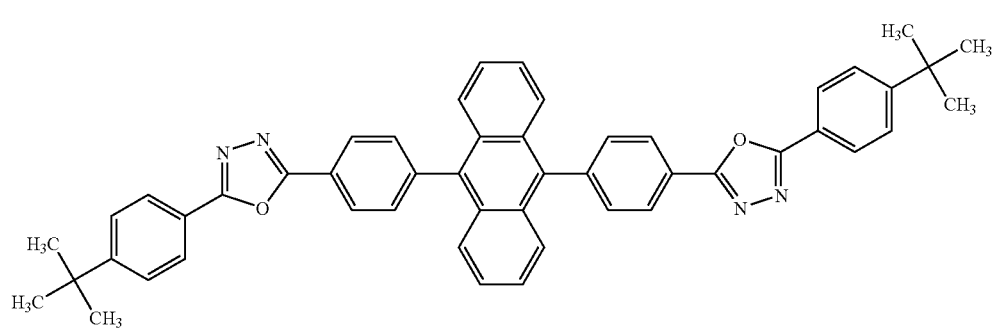
(161)

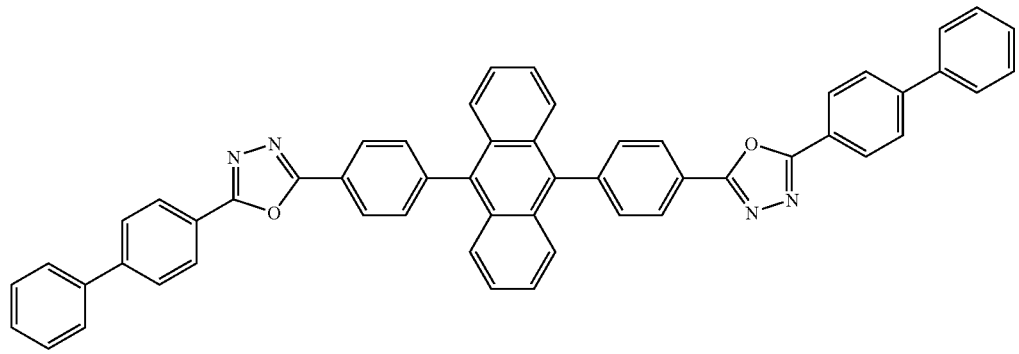
(162)
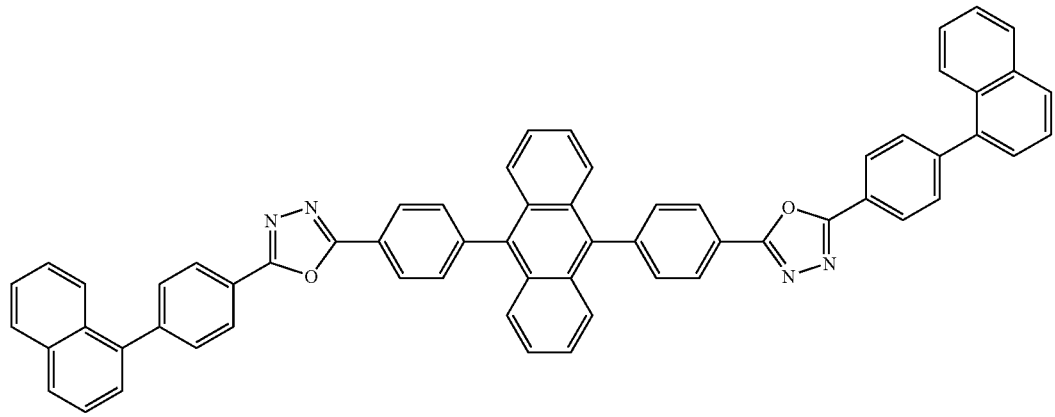
(163)
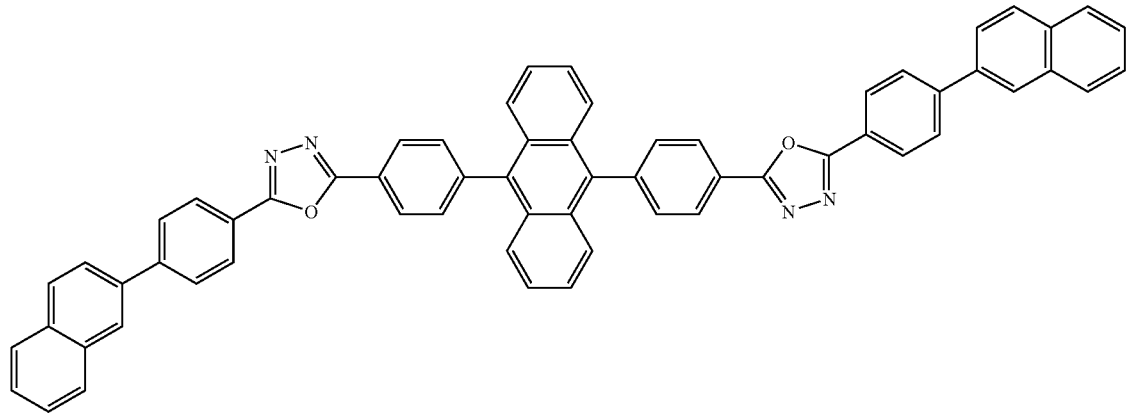
(164)
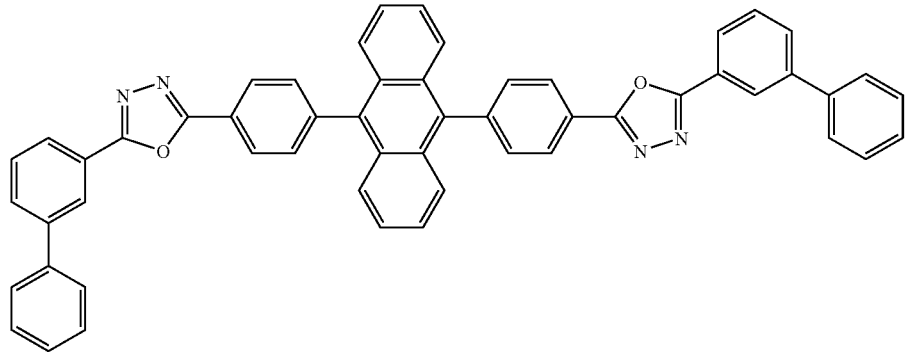
(165)

-continued

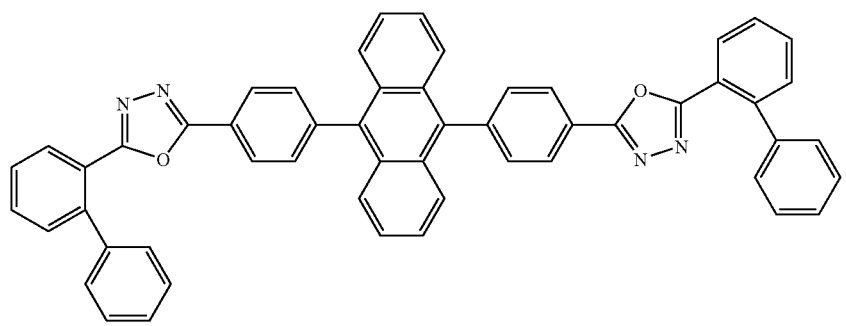
(166)

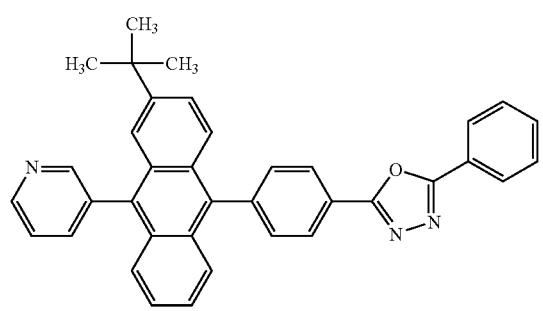
(167)

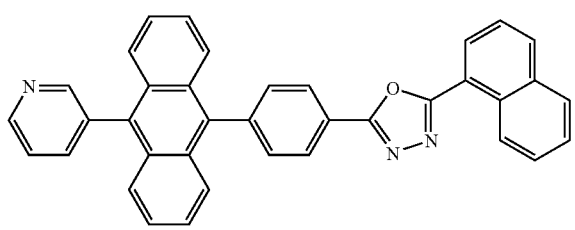
(168)

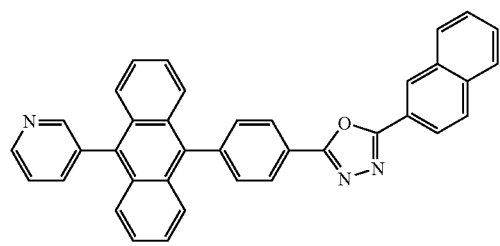
(169)

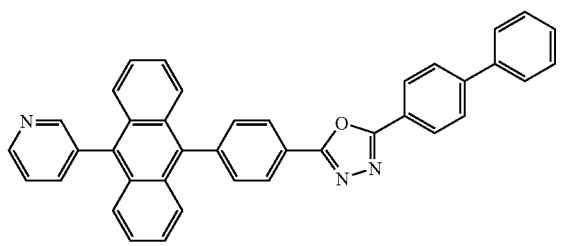
(170)

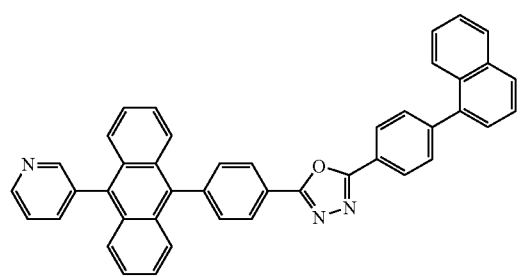
(171)

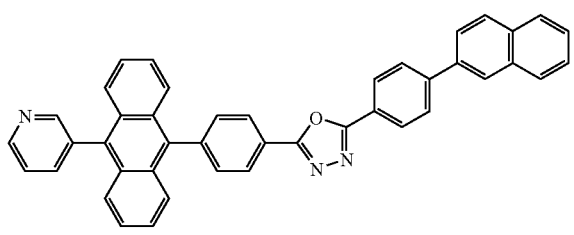
(172)

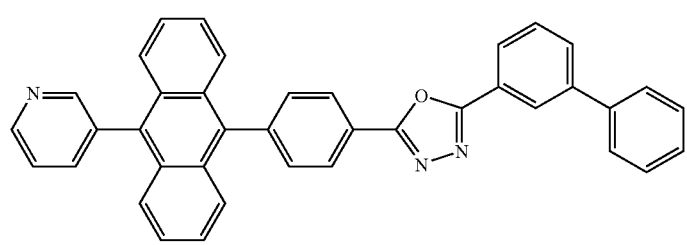
(173)

A variety of reactions can be applied to methods for synthesizing the oxadiazole derivatives which are embodiments of the present invention. For example, the oxadiazole derivatives represented by General Formulas (G1) and (G2) which are embodiments of the present invention can be synthesized by performing synthesis reactions described hereinbelow. Note that methods for synthesizing the oxadiazole derivatives which are embodiments of the present invention are not limited to the following synthesis method.

<Method 1 for Synthesizing Oxadiazole Derivative Represented by General Formula (G1)>

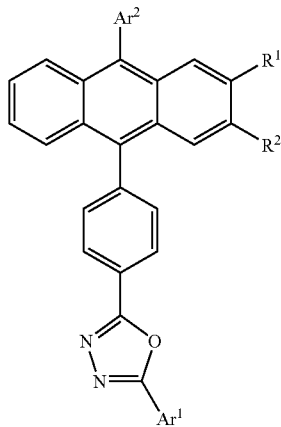

(G1)

In the formula, Ar$^1$ represents a substituted or unsubstituted aryl group having 6 to 10 carbon atoms in a ring. Note that when Ar$^1$ has a substituent, the substituent is an alkyl group having 1 to 4 carbon atoms or an aryl group having 6 to 10 carbon atoms in a ring. In addition, Ar$^2$ represents a substituted or unsubstituted aryl group having 6 to 10 carbon atoms in a ring or a substituted or unsubstituted heteroaryl group having 4 to 9 carbon atoms. Note that when Ar$^2$ has a substituent, the substituent is an alkyl group having 1 to 4 carbon atoms or an aryl group having 6 to 10 carbon atoms in a ring. In addition, R$^1$ and R$^2$ independently represent a hydrogen atom or an alkyl group having 1 to 4 carbon atoms.

The oxadiazole derivative represented by General Formula (G1) can be synthesized according to Synthetic Scheme (A-1) below. Specifically, coupling of boronic acid of an anthracene derivative (Compound A1) and a halide oxadiazole derivative (Compound B1) according to a Suzuki-Miyaura reaction using a palladium catalyst in the presence of a base can provide the oxadiazole derivative (General Formula (G1)) which is described in this embodiment (Synthetic Scheme (A-1)).

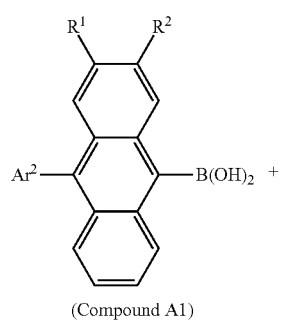
(Compound A1)

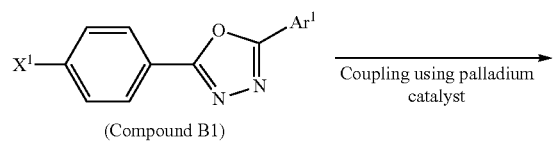
(Compound B1)

(A-1)

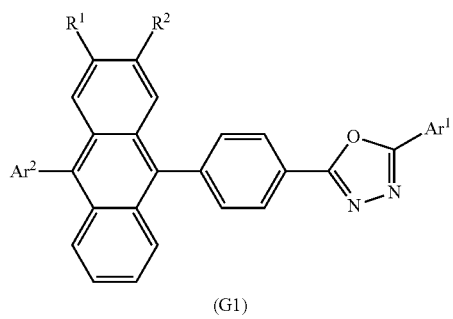
(G1)

Note that in Synthetic Scheme (A-1), X$^1$ represents halogen. Examples of halogen include iodine and bromine.

Examples of palladium catalysts that can be used in Synthesis Scheme (A-1) include palladium(II) acetate, tetrakis(triphenylphosphine)palladium(0), and the like. Examples of ligands of the palladium catalyst include tri(ortho-tolyl)phosphine, triphenylphosphine, tricyclohexylphosphine, and the like.

Examples of bases that can be used in Synthesis Scheme (A-1) include an organic base such as sodium tert-butoxide, an inorganic base such as potassium carbonate, and the like.

Examples of solvents that can be used in Synthesis Scheme (A-1) include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as 1,2-dimethoxyethane and water; and the like. It is also possible to use a mixed solvent of toluene and water, a mixed solvent of toluene, ethanol and water, or the like.

<Method 2 for Synthesizing Oxadiazole Derivative Represented by General Formula (G1)>

Alternatively, the oxadiazole derivative represented by General Formula (G1) can be synthesized according to Synthesis Scheme (B-1) below. Specifically, coupling of a halide anthracene derivative (Compound A2) and boronic acid of an oxadiazole derivative (Compound B2) according to a Suzuki-Miyaura reaction using a palladium catalyst in the presence of a base can provide the oxadiazole derivative (General Formula (G1)) which is described in this embodiment (Synthetic Scheme (B-1)).

(B-1)

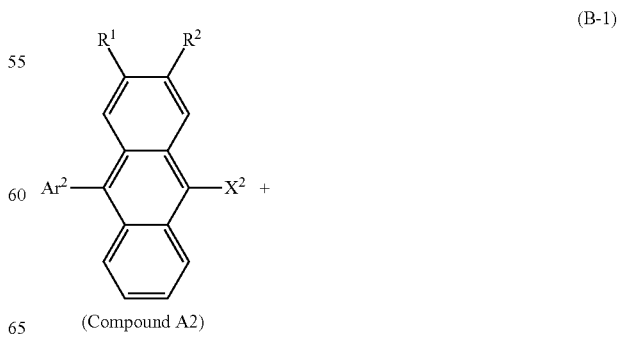
(Compound A2)

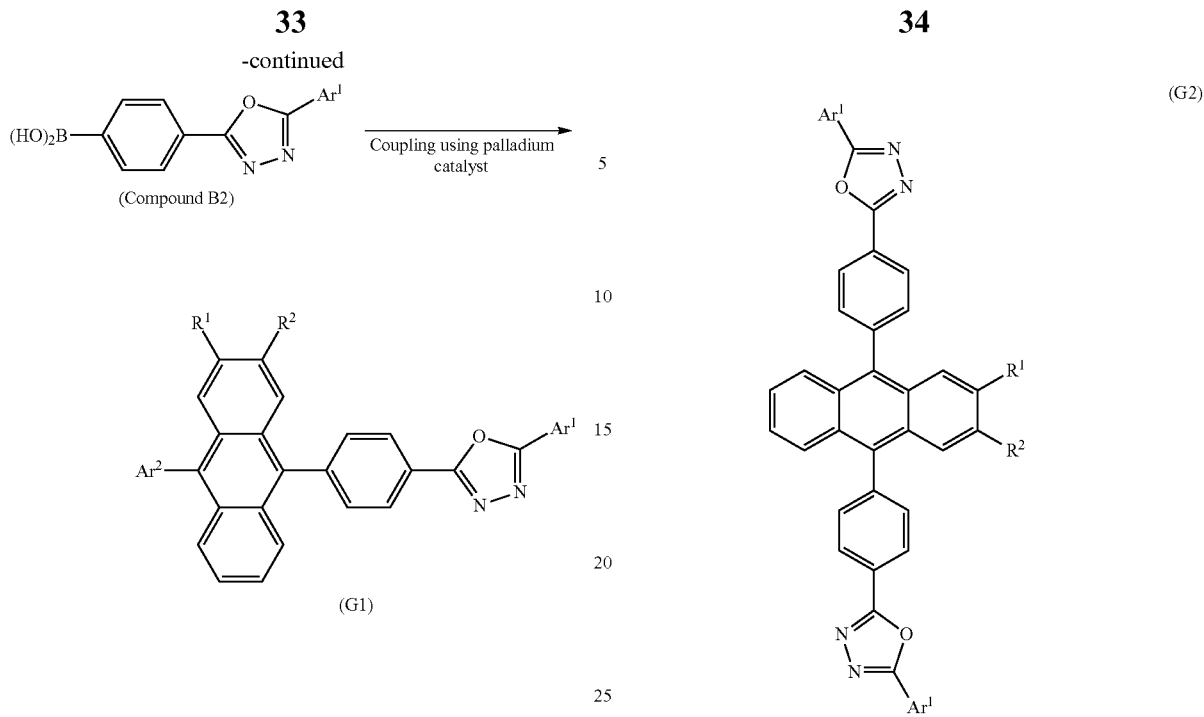

In the above Synthesis Scheme (B-1), $X^2$ represents halogen. Examples of halogen include iodine and bromine.

Examples of palladium catalysts that can be used in Synthesis Scheme (B-1) include palladium(II) acetate, tetrakis(triphenylphosphine)palladium(0), and the like. Examples of ligands of the palladium catalyst include tri(ortho-tolyl)phosphine, triphenylphosphine, tricyclohexylphosphine, and the like.

Examples of bases that can be used in Synthesis Scheme (B-1) include an organic base such as sodium tert-butoxide, an inorganic base such as potassium carbonate, and the like.

Examples of solvents that can be used in Synthesis Scheme (B-1) include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as 1,2-dimethoxyethane and water; and the like. It is also possible to use a mixed solvent of toluene and water, a mixed solvent of toluene, ethanol and water, or the like.

Note that the above synthesis methods are non-limiting examples; thus, the oxadiazole derivative represented by General Formula (G1) can be synthesized by some other method.

<Method of Synthesizing Oxadiazole Derivative Represented by General Formula (G2)>

Next, a method of synthesizing the oxadiazole derivative represented by the following General Formula (G2) is described.

In the formula, $Ar^1$ represents a substituted or unsubstituted aryl group having 6 to 10 carbon atoms in a ring. Note that when $Ar^1$ has a substituent, the substituent is an alkyl group having 1 to 4 carbon atoms or an aryl group having 6 to 10 carbon atoms in a ring. In addition, $R^1$ and $R^2$ independently represent a hydrogen atom or an alkyl group having 1 to 4 carbon atoms.

(Step 1)

First, an anthraquinone derivative (Compound C1) and oxadiazole aryllithium (Compound D1) are reacted, whereby a diol of a 9,10-dihydroanthracene derivative (Compound E1) can be obtained (Synthetic Scheme (C-1)).

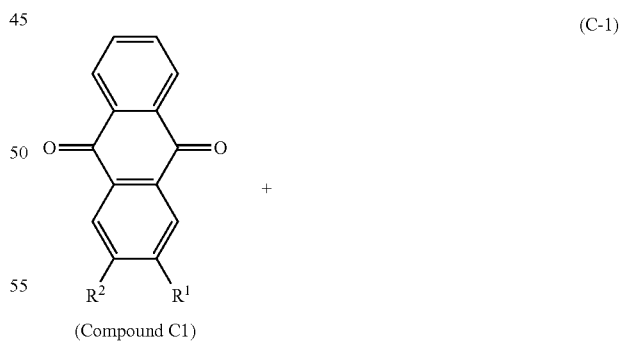

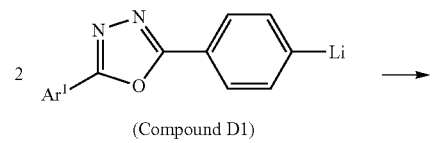

-continued

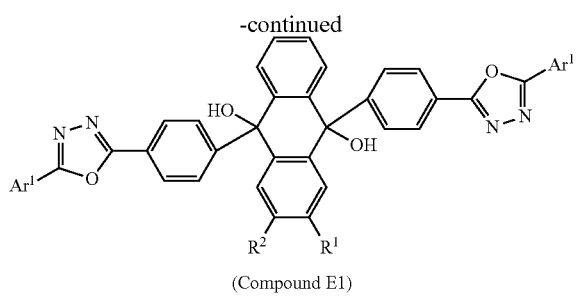

(Compound E1)

(Step 2)

Next, using the diol of a 9,10-dihydroanthracene derivative (Compound E1), sodium phosphinate monohydrate, potassium iodide, and acetic acid, the oxadiazole derivative (General Formula (G2)) which is described in this embodiment can be obtained (Synthetic Scheme (D-1)).

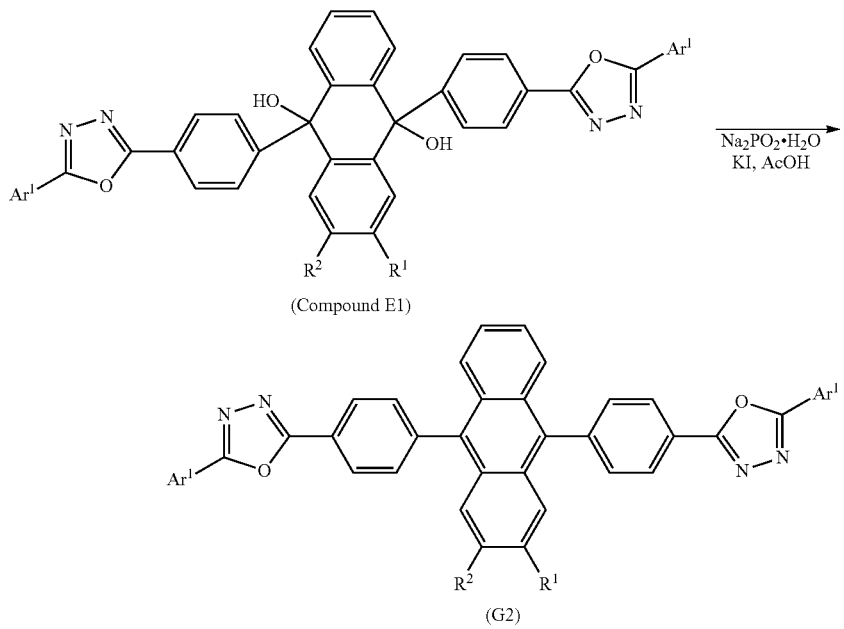

Embodiment 2

In this embodiment, description is given for a light-emitting element formed using any of the oxadiazole derivatives which are embodiments of the present invention for a light-emitting layer, with reference to FIG. 1.

FIG. 1 illustrates a light-emitting element in which an EL layer 102 including a light-emitting layer 113 is interposed between a first electrode 101 and a second electrode 103. In addition, the EL layer 102 includes any of the oxadiazole derivatives which are embodiments of the present invention as described in Embodiment 1.

By applying a voltage to such a light-emitting element, holes injected from the first electrode 101 side and electrons injected from the second electrode 103 side recombine in the light-emitting layer 113, whereby light is emitted. Note that in the light-emitting element described, in this embodiment, the first electrode 101 and the second electrode 103 function as an anode and a cathode, respectively.

When the first electrode 101 functions as an anode, it is preferably formed using a metal, an alloy, an electrically conductive compound, a mixture thereof, or the like which has a high work function (specifically, a work function of 4.0 eV or more). Specific examples include indium oxide-tin oxide (ITO: indium tin oxide), indium oxide-tin oxide containing silicon or silicon oxide, indium oxide-zinc oxide (IZO: indium zinc oxide), and indium oxide containing tungsten oxide and zinc oxide, and the like. Other than these, gold (Au), platinum (Pt), nickel (Ni), tungsten (W), chromium (Cr), molybdenum (Mo), iron (Fe), cobalt (Co), copper (Cu), palladium (Pd), titanium (Ti), or the like can be used.

Note that any of a variety of metals, alloys, or electrically conductive compounds, a mixture thereof, or the like can be used for the first electrode 101 regardless of the work function, when a layer which is included in the EL layer 102 and in contact with the first electrode 101 is formed using the later-described composite material including a mixture of an organic compound and an electron acceptor. For instance, aluminum (Al), silver (Ag), an alloy containing aluminum (e.g., Al—Si), or the like can be used.

Note that the first electrode 101 can be formed by, for example, a sputtering method, an evaporation method (including a vacuum evaporation method), or the like.

The EL layer 102 formed over the first electrode 101 has at least the light-emitting layer 113. The EL layer 102 is formed so as to include any of the oxadiazole derivatives which are embodiments of the present invention. For part of the EL layer 102, a known substance can be used. Also, either a low molecular compound or a high molecular compound can be used. Note that the substance for forming the EL layer 102 may have not only a structure formed of only an organic compound but also a structure including an inorganic compound.

Further, as illustrated in FIG. 1, the EL layer 102 includes the light-emitting layer 113 and also the following layers stacked in appropriate combination: a hole-injection layer 111 including a substance having a high hole-injection property, a hole-transport layer 112 including a substance having a high hole-transport property, an electron-transport layer 114 including a substance having a high electron-transport property, an electron-injection layer 115 including a layer including a substance to which electrons are easy to be injected or a layer including a substance promoting an electron-injection from the cathode, and the like.

The hole-injection layer 111 includes a substance having a high hole-injection property. As the substance having a high hole-injection property, a metal oxide such as molybdenum oxide, titanium oxide, vanadium oxide, rhenium oxide, ruthenium oxide, chromium oxide, zirconium oxide, hafnium oxide, tantalum oxide, silver oxide, tungsten oxide, or manganese oxide can be used. Alternatively, a phthalocyanine-based compound such as phthalocyanine (abbreviation: $H_2Pc$), copper(II) phthalocyanine (abbreviation: CuPc), or vanadyl phthalocyanine (abbreviation: VOPc) can be used.

Further, as examples of low molecular organic compounds, any of the following aromatic amine compounds can be used: 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1), and the like.

Further alternatively, any of high molecular compounds (e.g., oligomers, dendrimers, or polymers) can be used. For example, any of the following high molecular compounds can be used: poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). Alternatively, a high molecular compound to which acid is added, such as poly(3,4-ethylenedioxythiophene)/poly(styrenesulfonic acid) (PEDOT/PSS), or polyaniline/poly(styrenesulfonic acid) (PAni/PSS), can be used.

Alternatively, for the hole-injection layer 111, a composite material formed by combining an organic compound and an electron acceptor may be used. Such a composite material has excellent hole-injection and -transport properties because the electron acceptor produces holes in the organic compound. In this case, as the organic compound, a material that can efficiently transport the produced holes (a substance having a high hole-transport property) is preferably used.

As the organic compound used for the composite material, a variety of compounds such as aromatic amine compounds, carbazole derivatives, aromatic hydrocarbon, and high molecular compounds (e.g., oligomers, dendrimers, or polymers) can be used. Note that an organic compound used for the composite material preferably has a high hole-transport property. Specifically, a substance having a hole mobility of $10^{-6}$ cm$^2$/Vs or more is preferably used. Further, any other substance may be used as long as it has a higher hole-transport property than an electron-transport property. Organic compounds that can be used for the composite material are specifically given below.

Examples of the organic compounds that can be used for the composite material include aromatic amine compounds such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), and N,N'-bis(3-methylphenyl)-N,N'-diphenyl-[1,1'-biphenyl]-4,4'-diamine (abbreviation: TPD) and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl-2,3,5,6-tetraphenylbenzene.

Any of the following aromatic hydrocarbon compounds may be used: 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, and 2,3,6,7-tetramethyl-9,10-di(1-naphthyl)anthracene.

Any of the following aromatic hydrocarbon compounds may also be used: 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA).

Further, as examples of electron acceptors, there are organic compounds such as 7,7,8,8-tetracyano-2,3,5,6-tetrafluoroquinodimethane (abbreviation: $F_4$-TCNQ) and chloranil, transition metal oxides, and the like. Oxides of metals belonging to Group 4 to Group 8 of the periodic table of the elements may be used. Specifically, vanadium oxide, niobium oxide, tantalum oxide, chromium oxide, molybdenum oxide, tungsten oxide, manganese oxide, and rhenium oxide are suitable because of their high electron-accepting properties. Among these, molybdenum oxide is preferably used because it is stable in air and its hygroscopic property is low so that it can be easily handled.

Note that a composite material may be formed using any of the above-mentioned high molecular compounds such as PVK, PVTPA, PTPDMA, and Poly-TPD and any of the above-mentioned electron acceptors so as to be used for the hole-injection layer 111.

The hole-transport layer 112 includes a substance having a high hole-transport property. As a substance having a high hole-transport property, there are aromatic amine compounds such as NPB, TPD, 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). The substances mentioned here are mainly substances having a hole mobility of $10^{-6}$ cm$^2$/Vs or more. However, any other substance may also be used as long as it has a higher hole-transport property than an electron-transport property. Note that the layer including a high hole-transport property is not limited to a single layer and may be a stack of two or more layers including any of the above substances.

Further alternatively, for the hole-transport layer 112, a high molecular compound such as PVK, PVTPA, PTPDMA, or Poly-TPD can be used.

The light-emitting layer 113 includes a substance having a high light-emitting property, and can be formed using any of a variety of materials. As the substance having a high light-emitting property, a fluorescent compound which emits fluorescence or a phosphorescent compound which emits phosphorescence can be used, for example.

Examples of the phosphorescent compound that can be used for the light-emitting layer 113 are given below. Examples of materials for blue light emission include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA), and the like. In addition, examples of materials for green light emission include N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N,N-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. Further, examples of materials for yellow light emission include rubrene, 5,12-bis(1,1'-biphenyl-4-yl)-6,11-diphenyltetracene (abbreviation: BPT), and the like. Furthermore, examples of materials for red light emission include N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), and the like.

Examples of the phosphorescent compound that can be used for the light-emitting layer 113 are given below. As light-emitting materials for blue light emission, there are bis[2-(4',6'-difluorophenyl)pyridinato-N,$C^{2'}$]iridium(III)tetrakis(1-pyrazolyl)borate (abbreviation: FIr6), bis[2-(4',6'-difluorophenyl)pyridinato-N,$C^{2'}$]iridium(III)picolinate (abbreviation: FIrpic), bis[2-(3',5'-bistrifluoromethylphenyl)pyridinato-N,$C^{2'}$]iridium(III)picolinate (abbreviation: Ir(CF$_3$ppy)$_2$(pic)), bis[2-(4',6'-difluorophenyl)pyridinato-N,$C^{2'}$]iridium(III)acetylacetonate (abbreviation: FIracac), and the like. As light-emitting materials for green light emission, there are tris(2-phenylpyridinato-N,$C^{2'}$)iridium(III) (abbreviation: Ir(ppy)$_3$), bis(2-phenylpyridinato-N,$C^{2'}$)iridium(III)acetylacetonate (abbreviation: Ir(ppy)$_2$(acac)), bis(1,2-diphenyl-1H-benzimidazolato)iridium(III)acetylacetonate (abbreviation: Ir(pbi)$_2$(acac)), bis(benzo[h]quinolinato)iridium(III)acetylacetonate (abbreviation: Ir(bzq)$_2$(acac)), and the like. As light-emitting materials for yellow light emission, there are bis(2,4-diphenyl-1,3-oxazolato-N,$C^{2'}$)iridium(III)acetylacetonate (abbreviation: Ir(dpo)$_2$(acac)), bis[2-(4'-(perfluorophenylphenyl)pyridinato]iridium(III)acetylacetonate (abbreviation: Ir(p-PF-ph)$_2$(acac)), bis(2-phenylbenzothiazolato-N,$C^{2'}$)iridium(III)acetylacetonate (abbreviation: Ir(bt)$_2$(acac)), and the like. As light-emitting materials for orange light emission, there are tris(2-phenylquinolinato-N,$C^{2'}$)iridium(III) (abbreviation: Ir(pq)$_3$), bis(2-phenylquinolinato-N,$C^{2'}$)iridium(III)acetylacetonate (abbreviation: Ir(pq)$_2$(acac)), and the like. As light-emitting materials for red light emission, there are organic metal complexes such as bis[2-(2'-benzo[4,5-α]thienyl)pyridinato-N,$C^{3'}$)iridium(III)acetylacetonate (abbreviation: Ir(btp)$_2$(acac)), bis(1-phenylisoquinolinato-N,$C^{2'}$)iridium(III)acetylacetonate (abbreviation: Ir(piq)$_2$(acac), (acetylacetonato)bis[2,3-bis(4-fluorophenyl)quinoxalinato]iridium(III) (abbreviation: Ir(Fdpq)$_2$(acac)), and 2,3,7,8,12,13,17,18-octaethyl-21H,23H-porphine platinum(II) (abbreviation: PtOEP). In addition, rare earth metal complexes such as tris(acetylacetonato)(monophenanthroline)terbium(III) (abbreviation: Tb(acac)$_3$(Phen)), tris(1,3-diphenyl-1,3-propanedionato)(monophenanthroline)europium(III) (abbreviation: Eu(DBM)$_3$(Phen)), and tris[1-(2-thenyl)-3,3,3-trifluoroacetonato](monophenanthroline)europium(III) (abbreviation: Eu(TTA)$_3$(Phen)) emit light from a rare earth metal ion (electron transition between different multiplicities); therefore, such rare earth metal complexes can be used as a phosphorescent compound.

Note that the light-emitting layer may have a structure in which any of the above substances having a high light-emitting property (a guest material) is dispersed into another substance (a host material). As a substance in which the substance having a high light-emitting property is dispersed, various kinds of substances can be used, and it is preferable to use a substance whose lowest unoccupied molecular orbital (LUMO) level is higher and highest occupied molecular orbital (HOMO) level is lower than that of the substance with having a high light-emitting property.

As the substance in which the substance having a high light-emitting property is dispersed, specifically, any of the following materials can be used: metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), and bathocuproine (BCP); condensed aromatic compounds such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB3), 9,10-diphenylanthracene (abbreviation: DPAnth), and 6,12-dimethoxy-5,11-diphenylchrysene; aromatic amine compounds such as N,N-dipheyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]pheny}-9H-carbazol-3-amine (abbreviation: PCAPBA), N-(9,10-diphenyl-2-anthryl)-N,9-diphenyl-9H-carbazol-3-amine (abbreviation: 2PCAPA), NPB (or α-NPD), TPD, DFLDPBi, and BSPB; or the like.

Furthermore, as a substance (a host material) in which the substance having a high light-emitting property (a guest material) is dispersed, plural kinds of substances can be used.

As the light-emitting layer 113, a high molecular compound can also be used. Specifically, examples of materials for blue light emission include poly(9,9-dioctylfluorene-2,7- diyl) (abbreviation: PFO), poly[(9,9-dioctylfluorene-2,7-diyl)-co-(2,5-dimethoxybenzene-1,4-diyl)] (abbreviation: PF-DMOP), poly{(9,9-dioctylfluorene-2,7-diyl)-co-[N,N'-di-(p-butylphenyl)-1,4-diaminobenzene]} (abbreviation: TAB-PFH), and the like. Further, examples of materials for green light emission include poly(p-phenylenevinylene) (abbreviation: PPV), poly[(9,9-dihexylfluorene-2,7-diyl)-alt-co-(benzo[2,1,3]thiadiazole-4,7-diyl)] (abbreviation: PFBT), poly[(9,9-dioctyl-2,7-divinylenefluorenylene)-alt-co-(2-methoxy-5-(2-ethylhexyloxy)-1,4-phenylene)], and the like. Furthermore, examples of materials for orange to red light emission include poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-dihexyl-2,7-bis(1-cyanovinylene)fluorenylene]-alt-co-[2,5-bis(N,N'-diphenyl amino)-1,4-phenylene]}, poly{[2-methoxy-5-(2-ethylhexyloxy)-1,4-bis(1-cyanovinylenephenylene)]-alt-co-[2,5-bis(N,N-diphenylamino)-1,4-phenylene]} (abbreviation: CN-PPV-DPD), and the like.

Note that any of the oxadiazole derivatives which are embodiments of the present invention can be used also as a substance having a high light-emitting property (a guest material). The use of the oxadiazole derivative enables the light-emitting layer 113 to be a light-emitting layer having a high electron-transport property.

The electron-transport layer 114 includes a substance having a high electron-transport property. The oxadiazole derivatives described in Embodiment 1 have an excellent electron-transport property and therefore can be suitably used for the electron-transport layer 114. Note that the electron-transport layer is not limited to a single layer and may be a stack of two or more layers.

When the electron-transport layer 114 is a stack of two or more layers, the following are examples of low molecular organic compounds used as an additional substance having a high electron-transport property: metal complexes such as $Alq_3$, tris(4-methyl-8-quinolinolato)aluminum (abbreviation: $Almq_3$), bis(10-hydroxybenzo[h]quinolinato)beryllium (abbreviation: $BeBq_2$), BAlq, $Zn(BOX)_2$, and bis[2-(2'-hydroxyphenyl)benzothiazolato]zinc(II) (abbreviation: $Zn(BTZ)_2$). Alternatively, it is possible to use a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs). Further alternatively, it is possible to use a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy). The substances described here are mainly substances having electron mobility of $10^{-6}$ cm$^2$/Vs or more. Note that a substance other than the above substances may be used for the electron-transport layer as long as it has a higher electron-transport property than a hole-transport property.

The electron-injection layer 115 includes a layer including a substance to which electrons are easy to be injected or a layer including a substance promoting an electron-injection from the cathode. For the electron-injection layer 115, an alkali metal, an alkaline earth metal, or a compound thereof, such as lithium (Li), cesium (Cs), calcium (Ca), lithium fluoride (LiF), cesium fluoride (CsF), calcium fluoride ($CaF_2$), or lithium oxide (LiOx), can be used. Alternatively, a rare earth metal compound such as erbium fluoride ($ErF_3$) can also be used. Further alternatively, any of the above-described substances that are used to form the electron-transport layer 114 can be used.

For the electron-injection layer 115, a composite material formed by combining an organic compound and an electron donor may be used. Such a composite material has excellent electron-injection and -transport properties because the electron donor produces electrons in the organic compound. In this case, as the organic compound, a material that can efficiently transport the produced electrons is preferably used: for example, any of the above-described substances that are used to form the electron-transport layer 114 (e.g., a metal complex or a heteroaromatic compound) can be used. As the electron donor, a substance exhibiting an electron-donating property to the organic compound is used. Specifically, it is preferable to use any of alkali metals, alkali earth metals, or rare earth metals, such as lithium, cesium, magnesium, calcium, erbium, ytterbium, or the like. Alternatively, it is preferable to use any of alkali metal oxides or alkaline earth metal oxides: lithium oxide, calcium oxide, barium oxide, or the like. A Lewis base such as magnesium oxide can also be used. Alternatively, an organic compound such as tetrathiafulvalene (abbreviation: TTF) can be used.

Note that the hole-injection layer 111, hole-transport layer 112, light-emitting layer 113, electron-transport layer 114, and electron-injection layer 115 which are described above can each be formed by an evaporation method (including a vacuum evaporation method), an inkjet method, a coating method, or the like.

When the second electrode 103 functions as a cathode, it is preferably formed using a metal, an alloy, an electrically conductive compound, a mixture thereof, or the like which has a low work function (preferably, 3.8 eV or lower), or the like. Specifically, any of the following materials can be used: aluminum, silver, and the like, as well as elements that belong to Group 1 or Group 2 of the periodic table of the elements, that is, alkali metals such as lithium and cesium or alkaline earth metals such as magnesium, calcium, and strontium, or alloys thereof; rare earth metals such as europium and ytterbium, or alloys thereof.

Note that any of a variety of conductive materials such as Al, Ag, ITO, or indium oxide-tin oxide containing silicon or silicon oxide can be used regardless of the work function, when a layer which is included in the EL layer 102 and in contact with the second electrode 103 is formed using the above composite material including a mixture of the organic compound and the electron donor.

In the formation of the second electrode 103, a vacuum evaporation method or a sputtering method can be used. Alternatively, when a silver paste or the like is used, a coating method, an inkjet method, or the like can be used.

In the above-described light-emitting element, a current flows by applying a potential difference between the first electrode 101 and the second electrode 103 and holes and electrons recombine in the EL layer 102, whereby light is emitted. Then, the emitted light is extracted outside through one or both of the first electrode 101 and the second electrode 103. Therefore, one or both of the first electrode 101 and the second electrode 103 are electrodes having a property of transmitting visible light.

Note that with the use of the light-emitting element described in this embodiment, a passive matrix light-emitting device or an active matrix light-emitting device in which drive of the light-emitting element is controlled by a thin film transistor (TFT) can be fabricated.

Note that there is no particular limitation on the structure of the TFT in the case of fabricating an active matrix light-emitting device. A staggered TFT or an inverted staggered TFT can be employed in appropriate. Further, a driver circuit formed over a substrate may be formed using both of an n-type TFT and a p-type TFT or only either an n-type TFT or a p-type TFT. Furthermore, there is no particular limitation on the crystallinity of a semiconductor film used for the TFT. For example, an amorphous semiconductor film, a crystalline semiconductor film, an oxide semiconductor film, or the like can be used.

In the light-emitting element described in this embodiment, the electron-transport layer 114 is formed using any of the oxadiazole derivatives having an excellent electron-transport property which are embodiments of the present invention, whereby element efficiency such as current efficiency can be improved.

Note that in Embodiment 2, the structures described in Embodiment 1 can be used in appropriate combination.

Embodiment 3

Figure 2:
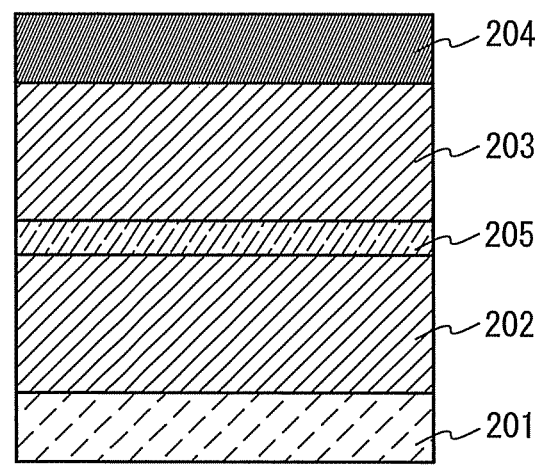
FIG. 2 illustrates a light-emitting element which is one embodiment of the present invention.

In this embodiment, a structure in which a plurality of EL layers is provided in a light-emitting element (hereinafter, referred to as a stacked-type element) is described as one embodiment of the present invention with reference to FIG. 2. This light-emitting element is a stacked-type light-emitting element that has a plurality of EL layers (a first EL layer 202 and a second EL layer 203) between a first electrode 201 and a second electrode 204. Note that although the number of the EL layers is two in this embodiment, it may be three or more.

In this embodiment, the first electrode 201 functions as an anode, and the second electrode 204 functions as a cathode. Note that the first electrode 201 and the second electrode 204 can have structures similar to those described in Embodiment 2. Further, the plurality of EL layers (the first EL layer 202 and the second EL layer 203) can have a structure similar to the structure in Embodiment 2. In addition, the structures of the plurality of EL layers (the first EL layer 202 and the second EL layer 203) may be the same or different from each other.

Further, a charge generation layer 205 is provided between the plurality of EL layers (the first EL layer 202 and the second EL layer 203). The charge generation layer 205 has a function of injecting electrons into one of the EL layers and injecting holes into the other of the EL layers when a voltage is applied to the first electrode 201 and the second electrode 204. In this embodiment, when a voltage is applied so that the potential of the first electrode 201 is higher than that of the second electrode 204, the charge generation layer 205 injects electrons into the first EL layer 202 and injects holes into the second EL layer 203.

Note that the charge generation layer 205 preferably has the property of transmitting visible light in terms of light extraction efficiency. Further, the electric conductivity of the charge generation layer 205 may be lower than that of the first electrode 201 or the second electrode 204.

The charge generation layer 205 may have either a structure in which an electron acceptor is added to an organic compound having a high hole-transport property or a structure in which an electron donor is added to an organic compound having a high electron-transport property. Alternatively, a stack of both structures may be used.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]-biphenyl (abbreviation: BSPB), or the like can be used. The substances described here are mainly materials having hole mobility of $10^{-6}$ cm$^2$/Vs or more. However, any substance other than the above substances may be used as long as it is an organic compound in which the hole-transport property is higher than the electron-transport property.

In addition, examples of the electron acceptor include 7,7,8,8-tetracyano-2,3,5,6-tetrafluoroquinodimethane (abbreviation: $F_4$-TCNQ), chloranil and transition metal oxides. Other examples are oxides of metals belonging to Group 4 to Group 8 of the periodic table. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in air and its hygroscopic property is low so that it can be easily handled.

Further, in the case of the structure in which an electron donor is added to an organic compound having a high electron-transport property, as the organic compound having a high electron-transport property, as well as any of the oxadiazole derivatives which are embodiments of the present invention, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Besides the metal complexes, PBD, OXD-7, TAZ, BPhen, BCP, or the like can also be used. The substances described here are mainly materials having electron mobility of $10^{-6}$ cm$^2$/Vs or more. Note that any substance other than the above substances may be used as long as it is an organic compound in which the electron-transport property is higher than the hole-transport property.

Further, as the electron donor, an alkali metal, an alkaline earth metal, a rare earth metal, a metal belonging to Group 13 of the periodic table, or an oxide or carbonate thereof can be used. Specifically, lithium, cesium, magnesium, calcium, ytterbium, indium, lithium oxide, cesium carbonate, or the like is preferably used. Alternatively, an organic compound such as tetrathianaphthacene may be used as the electron donor.

Note that forming the charge generation layer 205 by using the above materials can suppress an increase in drive voltage caused by the stack of the EL layers.

In this embodiment, the light-emitting element having two EL layers is described. However, the present invention can be applied to a light-emitting element in which three or more EL layers are stacked, in a similar manner. As in the light-emitting element according to this embodiment, by arranging a plurality of EL layers between a pair of electrodes so that the plurality of EL layers can be partitioned by a charge generation layer, light emission in a high luminance region can be achieved with current density kept low; thus, a light-emitting element having long lifetime can be realized. Further, when the light-emitting element is applied to a lighting apparatus, voltage drop due to the resistance of the electrode materials can be suppressed; thus, uniform light emission in a large area can be achieved. Furthermore, a light-emitting device capable of low-voltage driving with low power consumption can be realized.

Further, by forming the EL layers to emit light of different colors from each other, light emission of a desired color which is provided by the light-emitting element as a whole can be obtained. For example, by forming a light-emitting element having two EL layers such that the emission color of the first EL layer and the emission color of the second EL layer are complementary colors, the light-emitting element can provide white light emission as a whole.

As for a light-emitting element having three EL layers, for example, the light-emitting element as a whole can provide white light emission when the emission color of the first EL layer is red, the emission color of the second EL layer is green, and the emission color of the third EL layer is blue.

Note that the structure described in Embodiment 3 can be used in appropriate combination with any structure described in Embodiments 1 and 2.

Embodiment 4

In Embodiment 4, description is made of a passive-matrix light-emitting device and an active-matrix light-emitting device which are light-emitting devices fabricated using a light-emitting element, as embodiments of the present invention.

FIGS. 3A to 3D and FIG. 4 each exemplify a passive-matrix light-emitting device.

In the passive-matrix (also called simple-matrix) light-emitting device, a plurality of anodes arranged in stripes (in stripe form) is provided orthogonal to a plurality of cathodes arranged in stripes. A light-emitting layer is interposed at each intersection. Accordingly, light is emitted from a pixel at an intersection of an anode selected (to which a voltage is applied) and a cathode selected.

Figure 3A:
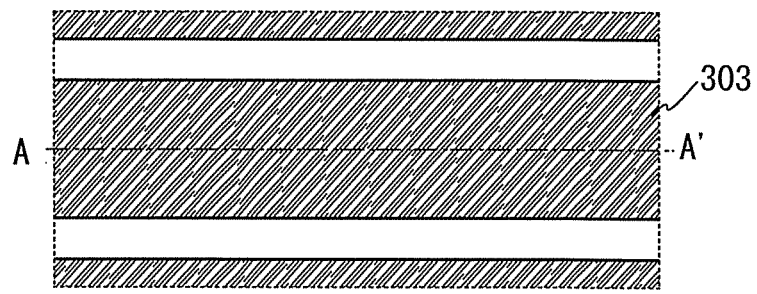
FIGS. 3A to 3D illustrate a passive matrix light-emitting device.
Figure 3B:
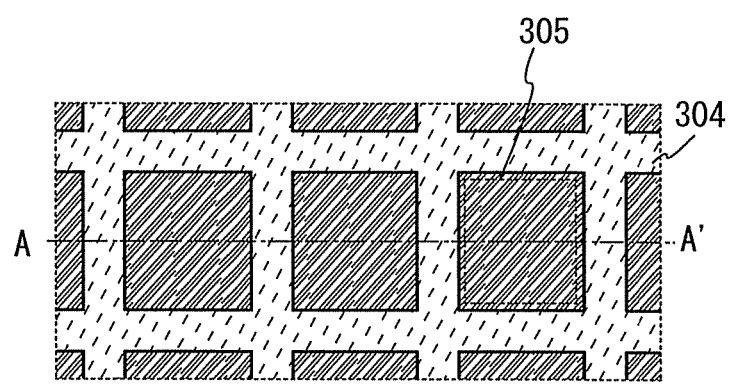
Figure 3C:
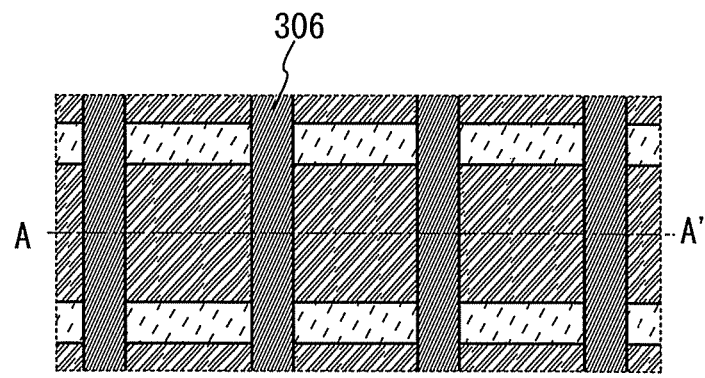
Figure 3D:
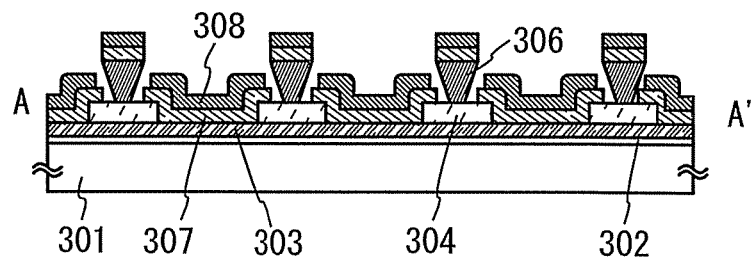

FIGS. 3A to 3C are top views of a pixel portion before sealing. FIG. 3D is a cross-sectional view taken along dashed line A-A' in each of FIGS. 3A to 3C.

Over a substrate 301, an insulating layer 302 is formed as a base insulating layer. Note that the base insulating layer is not necessarily formed. Over the insulating layer 302, a plurality of first electrodes 303 is arranged in stripes at regular intervals (see FIG. 3A).

A partition wall 304 having openings each corresponding to a pixel is provided over the first electrodes 303. The partition wall 304 having openings is formed using an insulating material (a photosensitive or nonphotosensitive organic material (polyimide, acrylic, polyamide, polyimide amide, resist, or benzocyclobutene) or an SOG film (such as a $SiO_x$ film containing an alkyl group)). Note that an opening 305 corresponding to each pixel acts as a light-emitting region (FIG. 3B).

Over the partition wall 304 that has openings, a plurality of mutually parallel reversely tapered partition walls 306 are provided to intersect with the first electrodes 303 (FIG. 3C). The reversely tapered partition walls 306 are formed by a photolithography method using a positive-type photosensitive resin by which a portion unexposed to light remains as a pattern, and the amount of light exposure or the length of development time is adjusted so that a lower portion of the pattern is etched more.

After the reversely tapered partition walls 306 are formed as illustrated in FIG. 3C, EL layers 307 and second electrodes 308 are sequentially formed as illustrated in FIG. 3D. The sum of the height of the partition wall 304 having openings and the height of the reversely tapered partition wall 306 exceeds the sum of the thickness of the EL layer 307 and the thickness of the second electrode 308. Therefore, as illustrated in FIG. 3D, the EL layers 307 and the second electrodes 308 which are separated into a plurality of regions are formed. Note that the plurality of separated regions are electrically isolated from one another.

The second electrodes 308 are parallel to each other in stripes and extend in the direction in which they intersect with the first electrodes 303. Note that parts that are supposed to form the EL layers 307 and parts of a conductive layer which are supposed to form the second electrodes 308 are formed over the reversely tapered partition walls 306. These parts are separated from the EL layers 307 and the second electrodes 308.

Note that the first electrode 303 may serve as an anode and the second electrode 308 may serve as a cathode, or vice versa. Further, the stack structure of the EL layer 307 may be adjusted depending on the polarities of the electrodes, as appropriate.

In addition, a sealing member such as a sealing can or a glass substrate may be attached to the substrate 301 with adhesive such as a sealant so that the light-emitting element may be placed in a sealed space, if necessary. In this manner, the light-emitting element can be prevented from deteriorating. The sealed space may be filled with filler or a dry inert gas. In addition, a desiccant or the like may be put between the substrate and the sealing member so that deterioration of the light-emitting element due to moisture or the like can be prevented. The desiccant removes a minute amount of moisture, thereby achieving sufficient desiccation. The desiccant can be a substance which absorbs moisture by chemical adsorption such as an oxide of an alkaline earth metal typified by calcium oxide or barium oxide. Note that a substance which absorbs moisture by physical adsorption such as zeolite or silica gel may be used as well.

Figure 4:
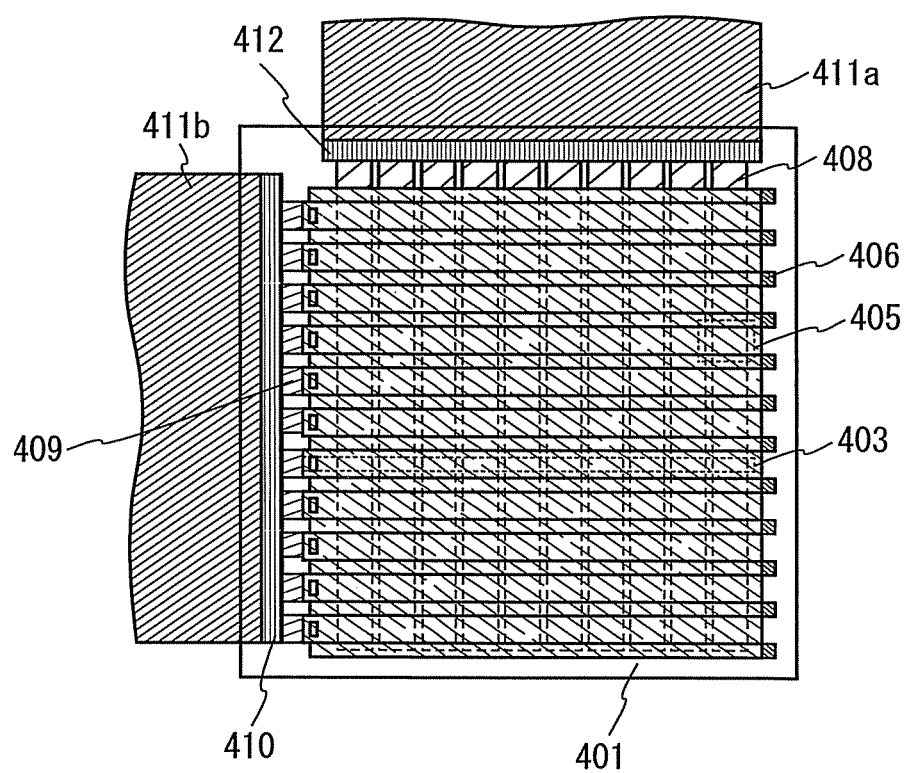
FIG. 4 illustrates a passive matrix light-emitting device.

FIG. 4 is a top view of the case where the passive-matrix light-emitting device illustrated in FIGS. 3A to 3D is provided with an FPC or the like.

As illustrated in FIG. 4, in a pixel portion forming an image display, scanning lines and data lines intersect with each other so that they are orthogonal to each other.

The first electrodes 303 in FIGS. 3A to 3D correspond to scan lines 403 in FIG. 4; the second electrodes 308 in FIGS. 3A to 3D correspond to data lines 408 in FIG. 4; and the reversely tapered partition walls 306 correspond to partition walls 406. The EL layers 307 illustrated in FIG. 3D are interposed between the data lines 408 and the scanning lines 403, and an intersection indicated by a region 405 corresponds to one pixel.

Note that the scanning lines 403 are electrically connected at their ends to connection wirings 409, and the connection wirings 409 are connected to an FPC 411 via an input terminal 410. The data lines 408 are connected to an FPC 411a via an input terminal 412.

If necessary, a polarizing plate, a circularly polarizing plate (including an elliptically polarizing plate), a retardation plate (a quarter-wave plate or a half-wave plate), or an optical film such as a color filter may be appropriately provided over a light-emitting surface. Further, the polarizing plate or the circularly polarizing plate may be provided with an anti-reflection film. For example, anti-glare treatment may be carried out by which reflected light can be diffused by projections and depressions on the surface so as to reduce the reflection.

Although FIG. 4 illustrates the example in which a driver circuit is not provided over a substrate 401, an IC chip including a driver circuit may be mounted on the substrate.

When the IC chip is mounted, a data line side IC and a scanning line side IC, in each of which the driver circuit for transmitting a signal to a pixel portion is formed, are mounted on the periphery of (outside) the pixel portion by a COG method. The mounting may be performed using TCP or a wire bonding method other than the COG method. TCP is TAB tape mounted with an IC, and the TAB tape is connected to a wiring over the substrate and the IC is mounted. Each of the data line side IC and the scanning line side IC may be formed using a silicon substrate or may be formed by formation of a driver circuit using a T over a glass substrate, a quartz substrate, or a plastic substrate.

Figure 5A:
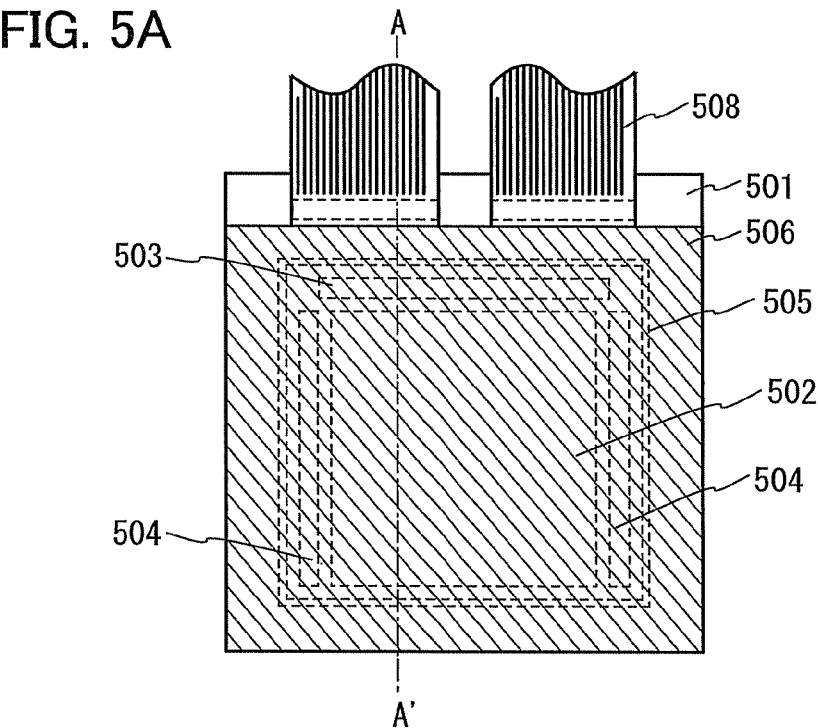
FIGS. 5A and 5B illustrate an active matrix light-emitting device.
Figure 5B:
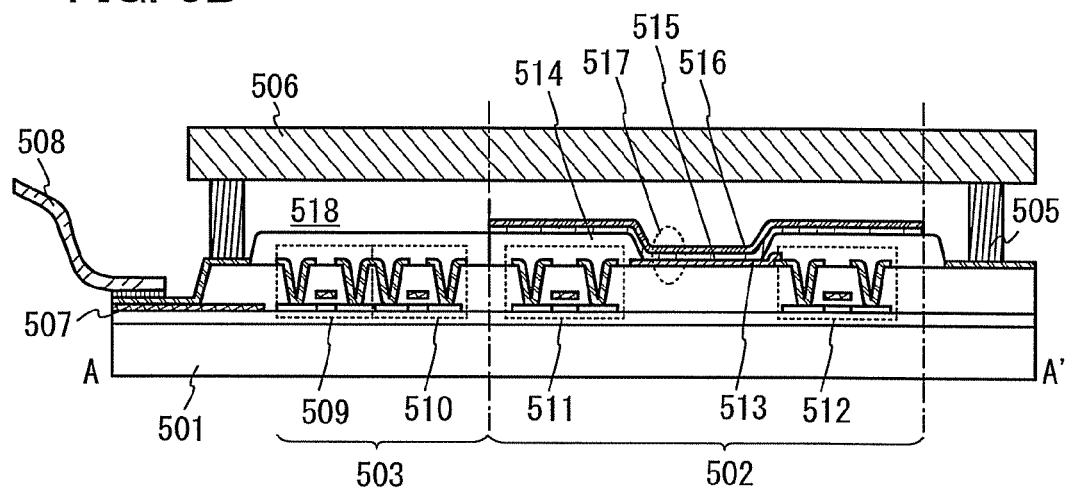

Next, an example of an active-matrix light-emitting device is described with reference to FIGS. 5A and 5B. Note that FIG. 5A is a top view illustrating a light-emitting device and FIG. 5B is a cross-sectional view taken along chain line A-A' in FIG. 5A. The active-matrix light-emitting device of this embodiment includes, over an element substrate 501, a pixel portion 502, a driver circuit portion (a source side driver circuit) 503, and a driver circuit portion (a gate side driver circuit) 504. The pixel portion 502, the driver circuit portion 503, and the driver circuit portion 504 are sealed with a sealant 505 between the element substrate 501 and a sealing substrate 506.

In addition, over the element substrate 501, a lead wiring 507 for connecting an external input terminal, through which a signal (e.g., a video signal, a clock signal, a start signal, a reset signal, or the like) or electric potential from the outside is transmitted to the driver circuit portion 503 and the driver circuit portion 504, is provided. Here, an example is described in which a flexible printed circuit (FPC) 508 is provided as the external input terminal. Although only the FPC is illustrated here, this FPC may have a printed wiring board (PWB) attached. The light-emitting device in this specification includes not only a light-emitting device itself but also a state in which an FPC or a PWB is attached thereto.

Next, a cross-sectional structure will be described with reference to FIG. 5B. Although the driver circuit portions and the pixel portion are formed over the element substrate 501, here, the pixel portion 502 and the driver circuit portion 503 which is the source side driver circuit are illustrated.

An example is illustrated in which a CMOS circuit which is a combination of an n-channel TFT 509 and a p-channel TFT 510 is formed as the driver circuit portion 503. Note that a circuit included in the driver circuit portion may be formed using various CMOS circuits, PMOS circuits, or NMOS circuits. Although a driver integrated type in which the driver circuit is formed over the substrate is described in this embodiment, the driver circuit is not necessarily formed over the substrate, and the driver circuit can be formed outside, not over the substrate.

Further, the pixel portion 502 has a plurality of pixels, each including a switching TFT 511, a current control TFT 512, and an anode 513 electrically connected to a wiring (a source electrode or a drain electrode) of the current control TFT 512. An insulator 514 is formed so as to cover an edge portion of the anode 513. In this embodiment, the insulator 514 is formed using a positive photosensitive acrylic resin.

In addition, in order to obtain favorable coverage by a film which is to be stacked over the insulator 514, the insulator 514 is preferably formed so as to have a curved surface with curvature at an upper edge portion or a lower edge portion. For example, in the case of using a positive photosensitive acrylic resin as a material for the insulator 514, the insulator 514 is preferably formed so as to have a curved surface with a curvature radius (0.2 μm to 3 μm) at the upper edge portion. Either a negative photosensitive material which becomes insoluble in an etchant by light or a positive photosensitive material which becomes soluble in an etchant by light can be used for the insulator 514. As the insulator 514, without limitation to an organic compound, an inorganic compound such as silicon oxide or silicon oxynitride can be used.

An EL layer 515 and a cathode 516 are stacked over the anode 513. Note that when an ITO film is used as the anode 513, and a stacked film of a titanium nitride film and a film containing aluminum as its main component or a stacked film of a titanium nitride film, a film containing aluminum as its main component, and a titanium nitride film is used as a wiring of the current control TFT 512 which is connected to the anode 513, resistance of the wiring can be low and favorable ohmic contact with the ITO film can be obtained. Note that, although not illustrated, the cathode 516 is electrically connected to the FPC 508 which is an external input terminal.

Note that in the EL layer 515, at least the light-emitting layer is provided and that a hole-injection layer, a hole-transport layer, an electron-transport layer, and/or an electron-injection layer may further be provided as appropriate. The light-emitting element 517 has a stack structure of the anode 513, the EL layer 515, and the cathode 516.

In addition, although the cross-sectional view of FIG. 5B illustrates only one light-emitting element 517, a plurality of light-emitting elements are arranged in matrix in the pixel portion 502. Light-emitting elements that emit light of three kinds of colors (R, G, and B) are selectively formed in the pixel portion 502, whereby a light-emitting device capable of full color display can be obtained. Alternatively, a light-emitting device which is capable of full color display may be manufactured by a combination with color filters.

By attachment of the sealing substrate 506 to the element substrate 501 with the sealant 505, a structure in which the light-emitting element 517 is provided in a space 518 surrounded by the element substrate 501, the sealing substrate 506, and the sealant 505 is obtained. Note that the space 518 may be filled with an inert gas (such as nitrogen and argon) or the sealant 505.

It is preferable to use an epoxy-based resin for the sealant 505. In addition, preferably, the material does not transmit moisture or oxygen as much as possible. As the sealing substrate 506, a plastic substrate formed of fiberglass-reinforced plastics (FRP), polyvinyl fluoride (PVF), polyester, acrylic, or the like can be used besides a glass substrate or a quartz substrate.

As described above, an active-matrix light-emitting device can be obtained.

Note that the structure described in Embodiment 4 can be used in appropriate combination with any structure described in Embodiments 1 to 3.

Embodiment 5

In this embodiment, with reference to FIGS. 6A to 6E and FIG. 7, description is given of examples of a variety of electronic devices and lighting devices that are completed by using any light-emitting device which is one embodiment of the present invention.

Examples of the electronic devices to which the light-emitting device is applied include television sets (also referred to as televisions or television receivers), monitors of computers or the like, cameras such as digital cameras or digital video cameras, digital photo frames, cellular phones (also referred to as mobile phones or cellular phone sets), portable game consoles, portable information terminals, audio reproducing devices, large-sized game machines such as pachinko machines, and the like. Further, examples of the lighting devices to which the light-emitting device is applied include desk lamps, ceiling lights, wall lights, and the like. Some specific examples of these electronic devices and lighting devices are illustrated in FIGS. 6A to 6E and FIG. 7.

Figure 6A:
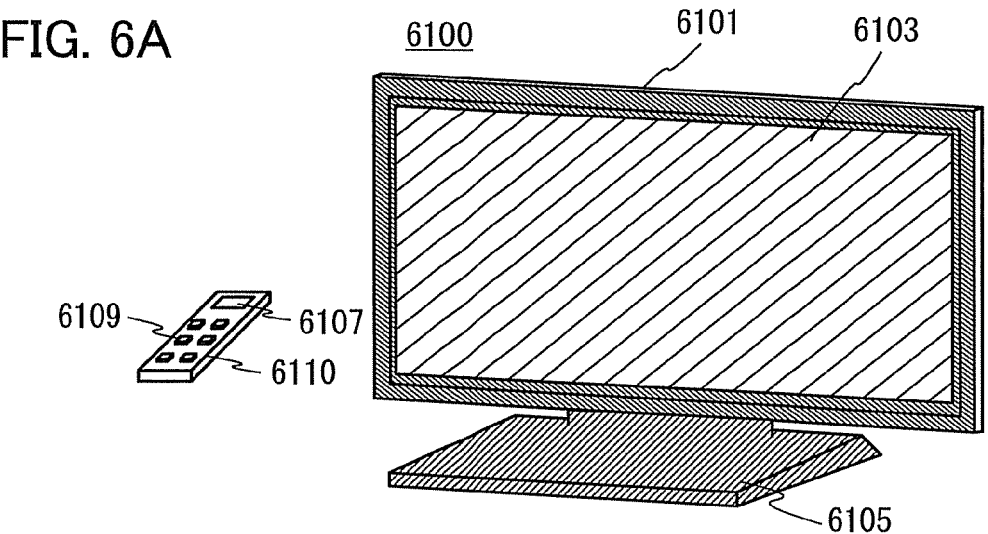
FIGS. 6A to 6E illustrate electronic devices and a lighting device.

FIG. 6A illustrates a television set 6100 as an example of an electronic device. In the television set 6100, a display portion 6103 is incorporated in a housing 6101. Images can be displayed by the display portion 6103, to which the light-emitting device can be applied. Here, the housing 6101 is supported by a stand 6105.

The television set 6100 can be operated with an operation switch of the housing 6101 or a separate remote controller 6110. Channels and volume can be controlled with an operation key 6109 of the remote controller 6110 so that an image displayed on the display portion 6103 can be controlled. Furthermore, the remote controller 6110 may be provided with a display portion 6107 for displaying data output from the remote controller 6110.

Note that the television set 6100 is provided with a receiver, a modem, and the like. With the use of the receiver, general television broadcasting can be received. Moreover, when the television set is connected to a communication network with or without wires via the modem, one-way (from a sender to a receiver) or two-way (between a sender and a receiver or between receivers) information communication can be performed.

Figure 6B:
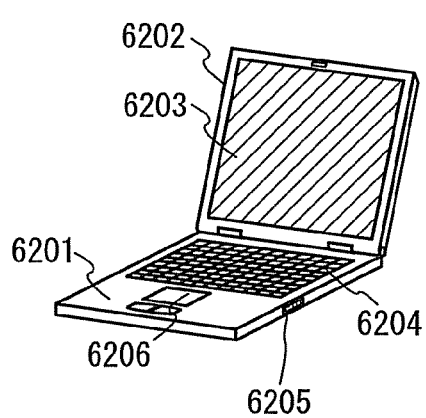

FIG. 6B illustrates a computer as an example of an electronic device. This computer includes a main body 6201, a housing 6202, a display portion 6203, a keyboard 6204, an external connecting port 6205, a pointing device 6206, and the like. Note that the computer is manufactured by using the light-emitting device for the display portion 6203.

Figure 6C:
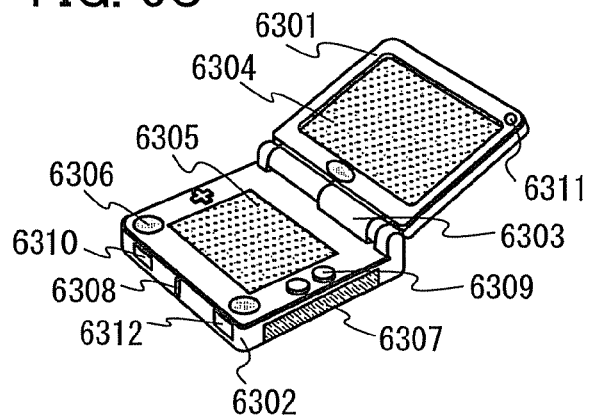

FIG. 6C illustrates a portable amusement machine as an example of an electronic device which includes two housings: a housing 6301 and a housing 6302. The housings 6301 and 6302 are connected with a connection portion 6303 so as to be opened and closed. A display portion 6304 and a display portion 6305 are incorporated in the housing 6301 and the housing 6302, respectively. In addition, the portable amusement machine illustrated in FIG. 6C includes a speaker portion 6306, a recording medium insertion portion 6307, an LED lamp 6308, an input means (an operation key 6309, a connection terminal 6310, a sensor 6311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 6312), and the like. It is needless to say that the structure of the portable amusement machine is not limited to the above as long as the light-emitting device is used for at least either the display portion 6304 or the display portion 6305, or both, and may be provided with an additional accessory as appropriate. The portable amusement machine illustrated in FIG. 6C has a function of reading a program or data stored in a recording medium to display it on the display portion, and a function of sharing information with another portable amusement machine by wireless communication. The portable amusement machine illustrated in FIG. 6C can have any other various functions without limitation to the above.

Figure 6D:
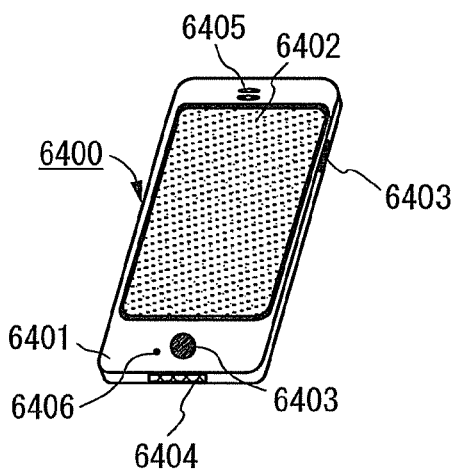

FIG. 6D illustrates a cellular phone as an example of an electronic device. A cellular phone 6400 is provided with a display portion 6402 incorporated in a housing 6401, operation buttons 6403, an external connection port 6404, a speaker 6405, a microphone 6406, and the like. Note that the cellular phone 6400 is fabricated by using the light-emitting device for the display portion 6402.

When the display portion 6402 of the cellular phone 6400 illustrated in FIG. 6D is touched with a finger or the like, data can be input into the cellular phone 6400. Furthermore, operations such as making calls and composing mails can be performed by touching the display portion 6402 with a finger or the like.

There are mainly three screen modes for the display portion 6402. The first mode is a display mode mainly for displaying images. The second mode is an input mode mainly for inputting data such as text. The third mode is a display-and-input mode in which two modes of the display mode and the input mode are combined.

For example, for operations of making calls and composing mails, the display portion 6402 is set to a text input mode mainly for inputting text so that text displayed on the screen can be input. In this case, a keyboard or number buttons are preferably displayed on almost the entire screen of the display portion 6402.

By providing a detection device which includes a sensor for detecting inclination, such as a gyroscope or an acceleration sensor, inside the cellular phone 6400, the direction of the cellular phone 6400 (whether the cellular phone 6400 is placed horizontally or vertically for a landscape mode or a portrait mode) is determined so that display on the screen of the display portion 6402 can be automatically switched.

In addition, the screen mode is switched by touching the display portion 6402 or operating the operation buttons 6403 of the housing 6401. Alternatively, the screen mode can be switched depending on the kind of images displayed on the display portion 6402. For example, when a signal of an image displayed on the display portion is of moving image data, the screen mode is switched to the display mode. When the signal is of text data, the screen mode is switched to the input mode.

Furthermore, in the input mode, when input by touching the display portion 6402 is not performed for a specified period while a signal detected by the optical sensor in the display portion 6402 is detected, the screen mode may be controlled so as to be switched from the input mode to the display mode.

The display portion 6402 can function as an image sensor. For example, an image of a palm print, a fingerprint, or the like is taken by touching the display portion 6402 with the palm or the finger, whereby personal authentication can be performed. Furthermore, by providing a backlight or a sensing light source emitting a near-infrared light for the display portion, an image of a finger vein, a palm vein, or the like can also be taken.

Figure 6E:
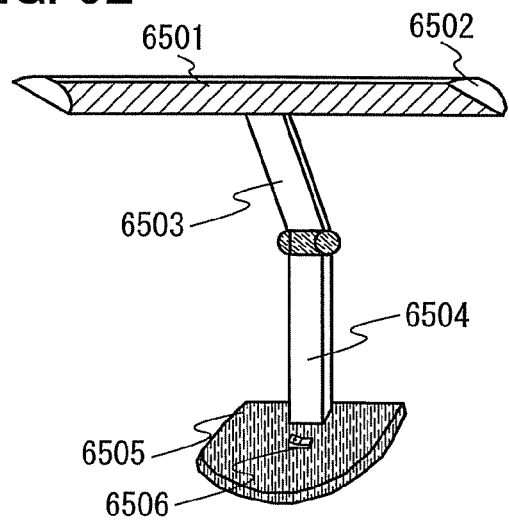

FIG. 6E illustrates a desk lamp as an example of a lighting device which includes a lighting portion 6501, a shade 6502, an adjustable arm 6503, a support 6504, a base 6505, and a power supply 6506. The desk lamp is manufactured using the light-emitting device in the lighting portion 6501.

Figure 7:
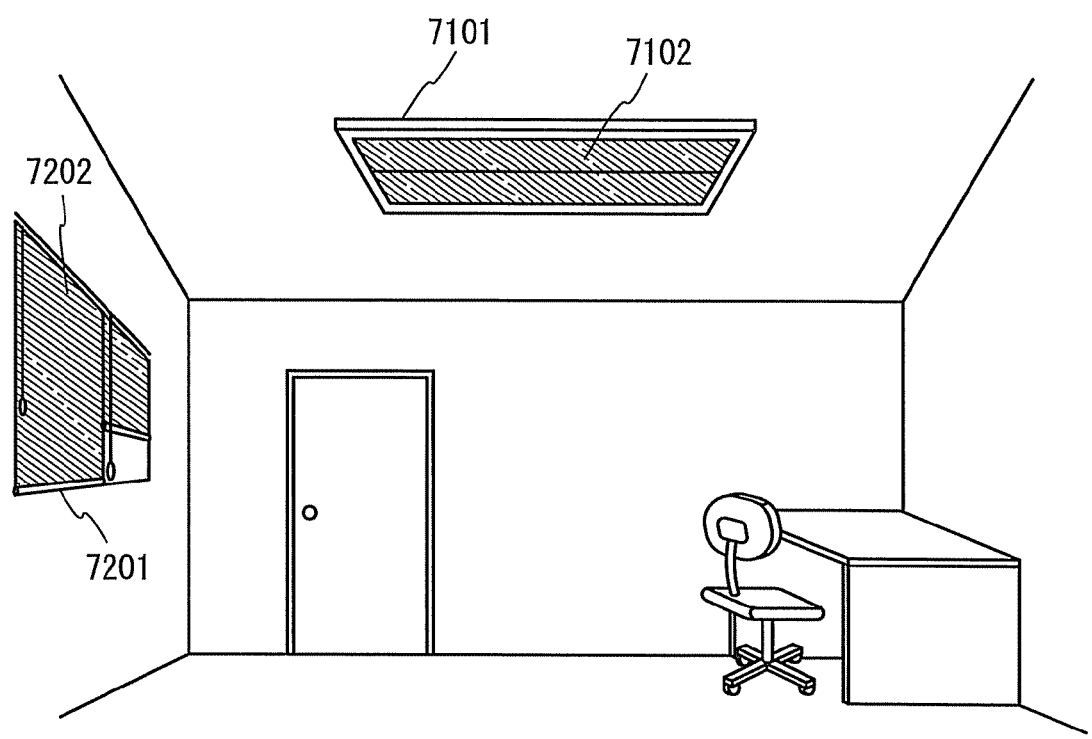
FIG. 7 illustrates lighting devices.

In addition, FIG. 7 illustrates a ceiling light 7101 and a wall light 7201 as examples of lighting devices.

Note that the light-emitting device realizes a larger area device and thus is applicable to a lighting portion 7102 of the ceiling light 7101, a lighting portion 7202 of the wall light 7201, and the like.

As described above, application of the light-emitting device can provide electronic devices and lighting devices. The applicable range of the light-emitting device is extremely wide so that the light-emitting device can be applied to a variety of electronic devices and lighting devices.

Note that in Embodiment 5, the structures described in Embodiments 1 to 4 can be used in appropriate combination.

Example 1

In Example 1, a method of synthesizing the oxadiazole derivative represented by Structural Formula (100) which is one embodiment of the present invention, 2-phenyl-5-[4-(10-phenyl-9-anthryl)phenyl]-1,3,4-oxadiazole (abbreviation: O11PhA), will be specifically described.

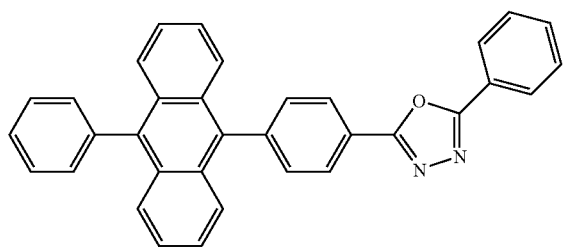

Synthesis of 2-Phenyl-5-[4-(10-phenyl-9-anthryl)phenyl]-1,3,4-oxadiazole

The synthetic scheme of 2-phenyl-5-[4-(10-phenyl-9-anthryl)phenyl]-1,3,4-oxadiazole is shown in (E-1).

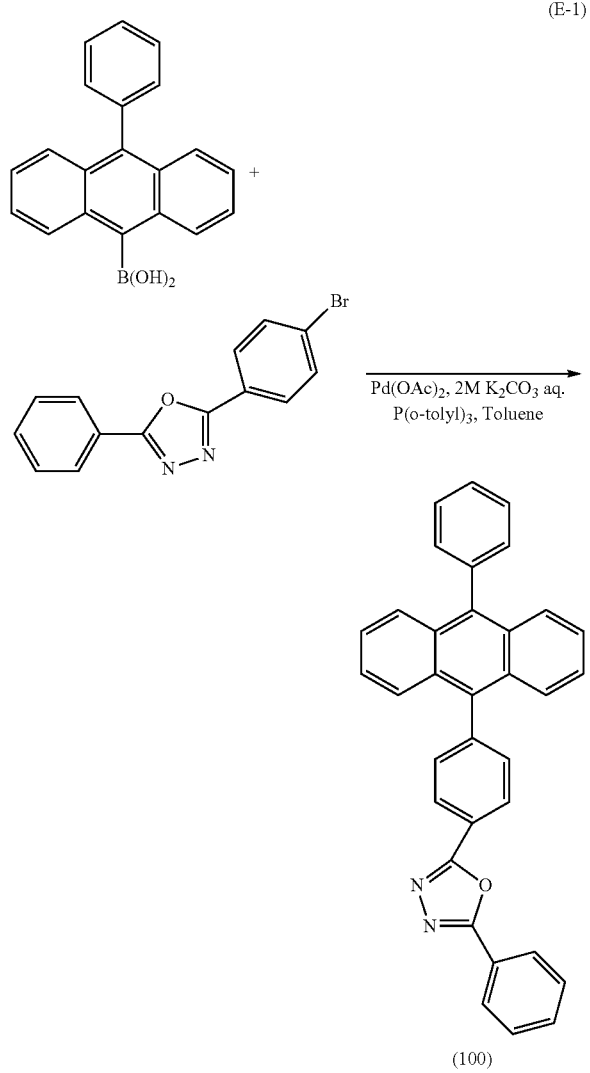

In a 200 mL three-necked flask were placed 2.0 g (6.6 mmol) of 2-(4-bromophenyl)-5-phenyl-1,3,4-oxadiazole, 2.0 g (6.6 mmol) of 10-phenylanthracene-9-boronic acid, and 0.30 g (0.99 mmol) of tri(ortho-tolyl)phosphine, and the atmosphere in the flask was replaced with nitrogen. To this mixture were added 40 mL of toluene and 20 mL of an aqueous solution of potassium carbonate. This mixture was degassed by reducing the pressure, and then the atmosphere in the flask was replaced with nitrogen.

To this mixture was added 0.030 g (0.13 mmol) of palladium(II) acetate, and the resulting mixture was stirred under a nitrogen stream at 100° C. for 5 hours. Then, this mixture was put in chloroform, and the resulting suspension was washed with water. The organic layer was suction filtered through Celite (Wako Pure Chemical Industries. Ltd., Catalog No. 531-16855). The resulting filtrate was concentrated to give a compound, which was purified by silica gel column chromatography. The column chromatography was performed first using toluene as a developing solvent and then using a mixed solvent of a 5:1 ratio of toluene to ethyl acetate as a developing solvent. The fractions obtained were concentrated to give a compound. The compound was recrystallized from a mixed solvent of chloroform and hexane, so that 2.5 g of a pale yellow powdered solid was obtained in 80% yield.

By a train sublimation method, 2.5 g of the obtained solid was purified. Under a reduced pressure of 7.0 Pa with a flow rate of argon at 3.0 mL/min, the sublimation purification was carried out at 240° C. for 20 hours. The amount of the compound was 2.3 g, and the yield thereof was 92%.

The compound obtained through the above synthesis method was examined by a nuclear magnetic resonance (NMR) method. The measurement data are shown below. $^1$H NMR (CDCl$_3$, 300 MHz): δ(ppm)=7.30-7.76 (m, 18H), 8.19-8.24 (m, 2H), 8.41 (d, J=7.8 Hz, 2H).

Figure 9A:
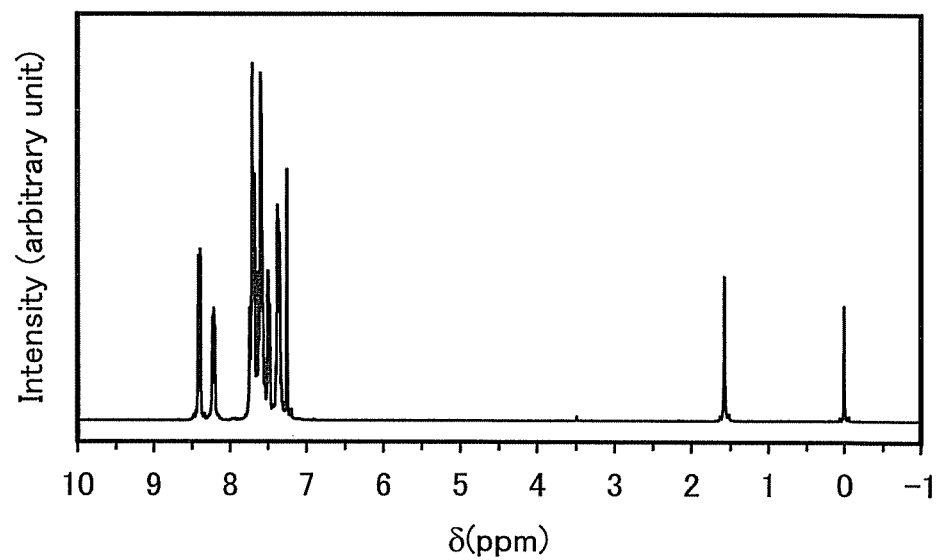
FIGS. 9A and 9B show $^1$H NMR charts of O11PhA represented by Structural Formula (100).
Figure 9B:
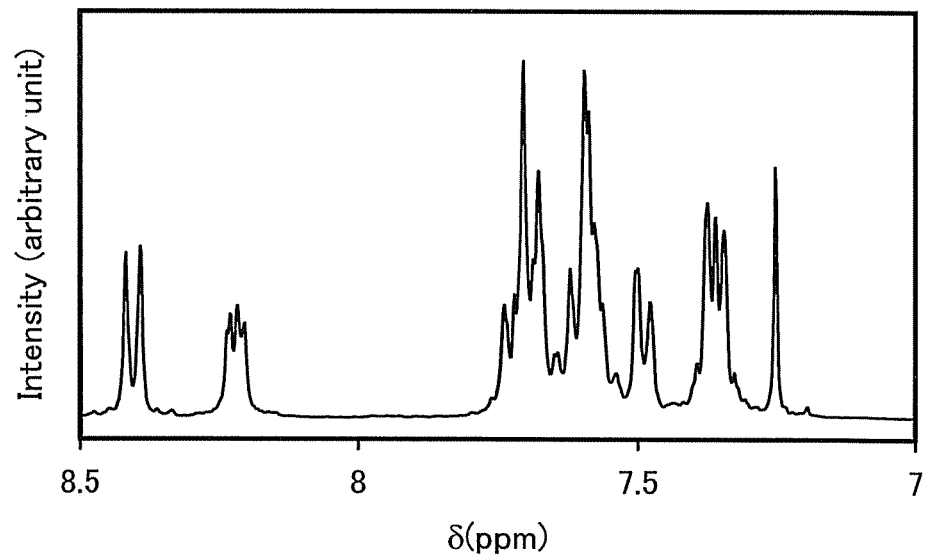

In addition, FIGS. 9A and 9B show $^1$H NMR charts. Note that FIG. 9B is a chart showing an enlarged part in the range of 7.0 ppm to 8.5 ppm in FIG. 9A. The measurement results demonstrate that this compound is 2-phenyl-5-[4-(10-phenyl-9-anthryl)phenyl]-1,3,4-oxadiazole (abbreviation: O11PhA), the oxadiazole derivative represented by the above Structural Formula (100) which is one embodiment of the present invention.

Figure 10A:
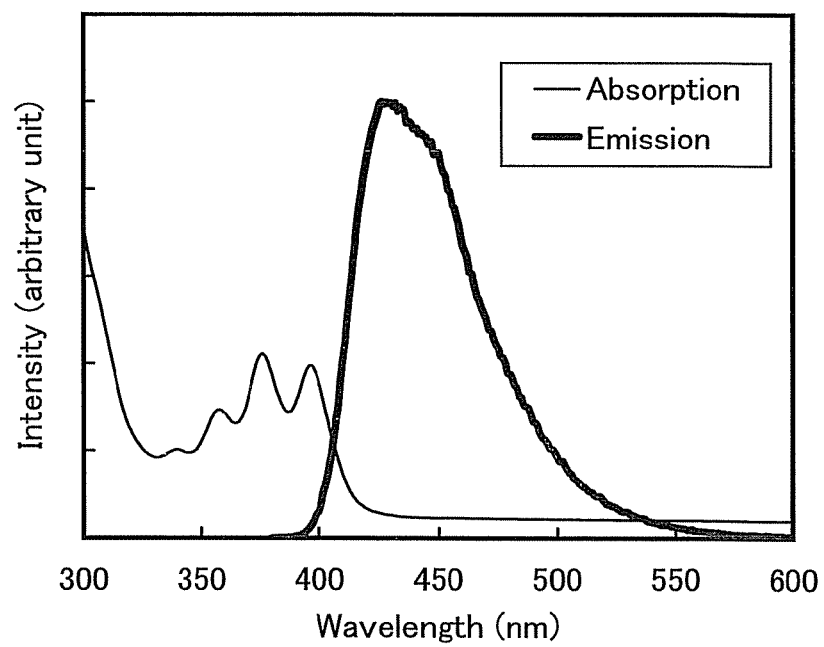
FIGS. 10A and 10B show an ultraviolet-visible absorption spectrum and an emission spectrum of O11PhA represented by Structural Formula (100).
Figure 10B:
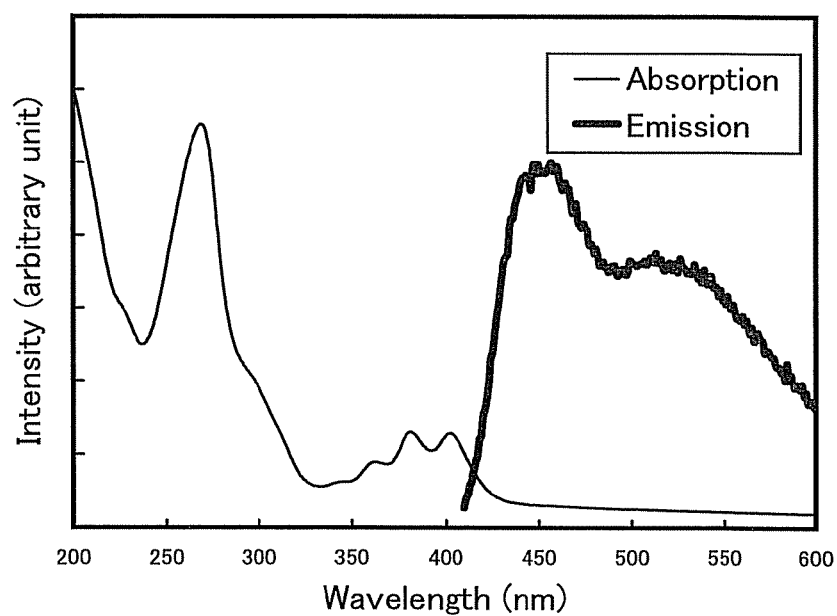

Further, FIG. 10A shows an absorption spectrum of a toluene solution of O11PhA, and FIG. 10B shows an absorption spectrum of a thin film of O11PhA. An ultraviolet-visible spectrophotometer (V-550, manufactured by JASCO Corporation) was used for the measurements. To measure the absorption spectrum of the toluene solution of O11PhA, the toluene solution was put into a quartz cell, and the absorption spectra of quartz and toluene were subtracted from that of the toluene solution in the quartz cell. Further, to measure the absorption spectrum of the thin film of O11PhA, a sample was formed by evaporation of O11PhA onto a quartz substrate, and the absorption spectrum of quartz was subtracted from that of the sample.

In FIG. 10A and FIG. 10B, the horizontal axis represents wavelength (nm) and the vertical axis represents absorption intensity (arbitrary unit). The absorption peaks of the toluene solution were at 338 nm, 356 nm, 375 nm, and 396 nm, while the absorption peak of the thin film was at 402 nm.

Further, FIG. 10A shows an emission spectrum of a toluene solution of O11PhA (an excitation wavelength of 356 nm), while FIG. 10B shows an emission spectrum of a thin film of O11PhA (an excitation wavelength of 402 nm). In FIG. 10A and FIG. 10B, the horizontal axis represents wavelength (nm) and the vertical axis also represents emission intensity (arbitrary unit). The maximum emission wavelength of the toluene solution was 430 nm (excitation wavelength of 356 nm), while the maximum emission wavelengths of the thin film were 457 nm and 526 nm (excitation wavelength of 402 nm).

Furthermore, by measurement with a photoelectron spectrometer (AC-2, manufactured by Riken Keiki, Co., Ltd.) in the atmosphere, the ionization potential of the thin film of O11PhA was found to be 5.51 eV. As a result, the HOMO level was found to be −5.51 eV. Moreover, using data on the absorption spectrum of the thin film of O11PhA, the absorption edge was obtained from Tauc plot, with an assumption of direct transition. The absorption edge was estimated as an optical energy gap, whereby the energy gap was found to be 2.95 eV. The LUMO level was calculated from the obtained values of the energy gap and the HOMO level, and found to be −2.56 eV.

In addition, the oxidation-reduction characteristics of O11PhA were measured. Cyclic voltammetry (CV) was employed. Note that an electrochemical analyzer (ALS model 600A, a product of BAS Inc.) was used for the measurements.

For a solution used in the CV measurements, dehydrated dimethylformamide (DMF, produced by Sigma-Aldrich Inc., 99.8%, Catalog No. 22705-6) was used as a solvent. Tetra-n-butylammonium perchlorate (n-Bu$_4$NClO$_4$, produced by Tokyo Chemical Industry Co., Ltd., Catalog No. T0836), which was a supporting electrolyte, was dissolved in the solvent such that the concentration of tetra-n-butylammonium perchlorate was 100 mmol/L. Furthermore, O11PhA, which was to be measured, was dissolved in the solution such that the concentration thereof was 2 mmol/L. In addition, a platinum electrode (PIE platinum electrode, produced by BAS Inc.) was used as a working electrode, a platinum electrode (Pt counter electrode for VC-3, (5 cm), produced by BAS Inc.) was used as an auxiliary electrode, and an Ag/Ag$^+$ electrode (RE-5 reference electrode for nonaqueous solvent, produced by BAS Inc.) was used as a reference electrode. Note that the measurements were conducted at room temperature.

The oxidation characteristics of O11PhA were examined by 100 cycles of measurements in which a scan for changing the potential of the working electrode with respect to the reference electrode from −0.32 V to 1.39 V and then from 1.39 V to −0.32 V was set to one cycle. Further, the reduction characteristics of O11PhA were examined by 100 cycles of measurements in which a scan for changing the potential of the working electrode with respect to the reference electrode from −0.15 V to −2.50 V and then from −2.50 V to −0.15 V was set to one cycle. Note that the scan rate for the CV measurements was set to 0.1 V/s.

The results reveal that there are no significant changes in the peak position and peak intensity of the CV curve in the oxidation-reduction reactions even after the 100 cycles of measurements. Accordingly, it is found that O11PhA, the oxadiazole derivative which is one embodiment of the present invention, is extremely stable to repetitive oxidation-reduction reactions.

Example 2

In Example 2, a method of synthesizing 3-{10-[4-(5-phenyl-1,3,4-oxadiazol-2-yl)phenyl]-9-anthryl}pyridine (abbreviation: PyAO11), the oxadiazole derivative represented by Structural Formula (121) which is one embodiment of the present invention, will be specifically described.

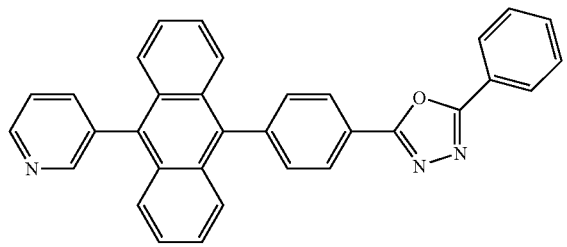

(121)

Step 1: Synthesis of 9-Anthraceneboronic acid

The synthetic scheme of 9-anthraceneboronic acid is shown in (F-1).

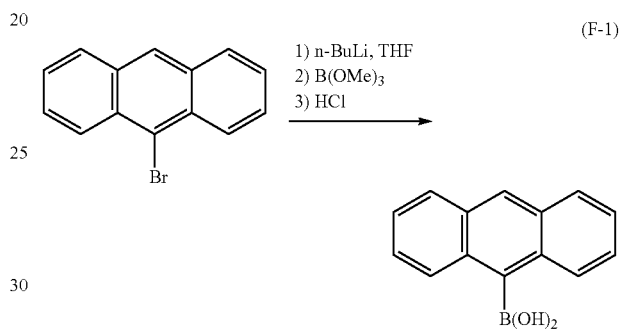

(F-1)

In a 500 mL three-necked flask were placed 7.7 g (30 mmol) of 9-bromoanthracene, and the atmosphere in the flask was replaced with nitrogen. To this mixture was added 200 mL of THF, and the solution was cooled to −80° C. under a nitrogen stream. Then, 18 mL (30 mmol) of 1.6 M n-butyllithium was dripped into the solution and stirred at the same temperature for 2 hours. After a predetermined time has passed, to this solution was added 6.8 mL (60 mmol) of trimethyl borate. The temperature of the solution was raised to room temperature, and then the solution was stirred for 17 hours. After a predetermined time has passed, 100 mL of 1.0 M hydrochloric acid was added to the solution, and stirred for 1 hour. The aqueous layer of the obtained mixture was extracted with ethyl acetate. The resulting extract and the organic layer were combined and washed with saturated brine, and then the organic layer was dried with magnesium sulfate. The obtained mixture was subjected to gravity filtration, and the filtrate was concentrated to give a solid. Recrystallization of this solid from toluene gave 5.2 g of a white powder in 80% yield, which was the desired substance.

Step 2: Synthesis of 3-(9-Anthryl)pyridine

The synthetic scheme of 3-(9-anthryl)pyridine is shown in (F-2).

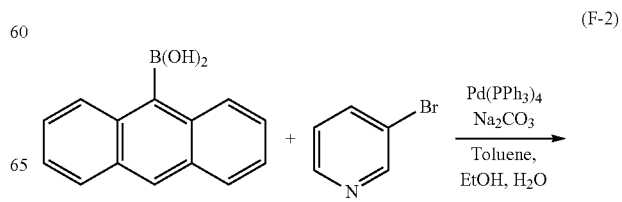

(F-2)

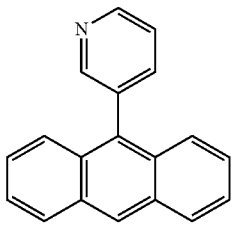

In a 200 mL three-necked flask were placed 5.2 g (23 mmol) of 9-anthraceneboronic acid, 4.0 g (25 mmol) of 3-bromopyridine, 5.2 g (50 mmol) of sodium carbonate, 50 mL of toluene, 25 mL of ethanol, and 25 mL of water. This mixture was degassed by being stirred under reduced pressure, and the atmosphere in the flask was replaced with nitrogen. To the mixture was added 0.28 g (0.25 mmol) of tetrakis(triphenylphosphine)palladium(0), and the mixture was stirred under a nitrogen stream at 80° C. for 7 hours. After a predetermined time has passed, water was added to the mixture, and the aqueous layer was extracted with toluene. The obtained extract and the organic layer were combined and washed with saturated brine, and then the organic layer was dried with magnesium sulfate. The obtained mixture was subjected to gravity filtration, and the resulting filtrate was concentrated to give an oily substance.

Recrystallization of this oily substance from a mixed solvent of toluene and hexane gave 2.8 g of a yellow powder in 46% yield, which was the desired substance.

Step 3: Synthesis of 3-(10-Bromo-9-anthryl)pyridine

The synthetic scheme of 3-(10-bromo-9-anthryl)pyridine is shown in (F-3).

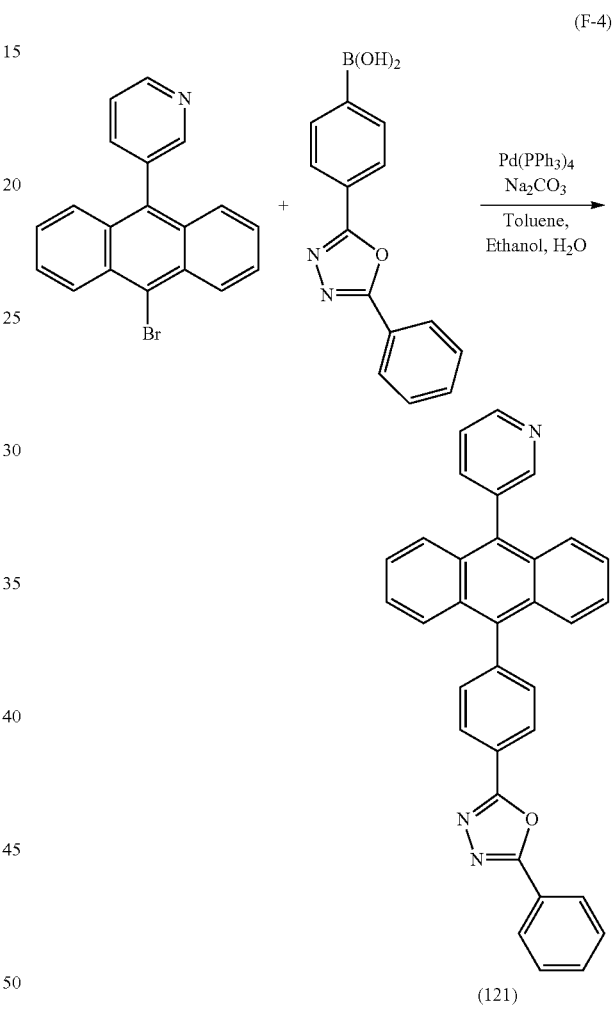

In a 200 mL three-necked flask were placed 1.0 g (4.0 mmol) of 3-(9-anthryl)pyridine and 25 mL of carbon tetrachloride. Under a nitrogen stream, 10 mL of a carbon tetrachloride solution containing 0.83 g (5.1 mmol) of bromine was dripped into this solution, followed by stirring at room temperature for 26 hours. After a predetermined time has passed, 100 mL of a 1.0 M sodium thiosulfate solution was added to this mixture. The aqueous layer of this mixture was extracted with chloroform. The obtained extract and the organic layer were combined and washed with a saturated aqueous solution of sodium hydrogen carbonate and with saturated brine, and dried with magnesium sulfate. This mixture was subjected to gravity filtration, and the filtrate was concentrated to give a solid. A chloroform solution of the obtained solid was suction filtered through Celite (produced by Wako Pure Chemical Industries, Ltd., Catalog No. 531-16855), Florisil (produced by Wako Pure Chemical Industries, Ltd., Catalog No. 540-00135), and alumina, and the filtrate was condensed to give a solid. Recrystallization of this solid from a mixed solvent of ethyl acetate and hexane gave 0.74 g of a pale yellow powder in 53% yield, which was the desired substance.

Step 4: Synthesis of 3-{10-[4-(5-Phenyl-1,3,4-oxadiazol-2-yl)phenyl]-9-anthryl}pyridine The synthetic scheme of 3-{10-[4-(5-phenyl-1,3,4-oxadiazol-2-yl)phenyl]-9-anthryl}pyridine is shown in (F-4).

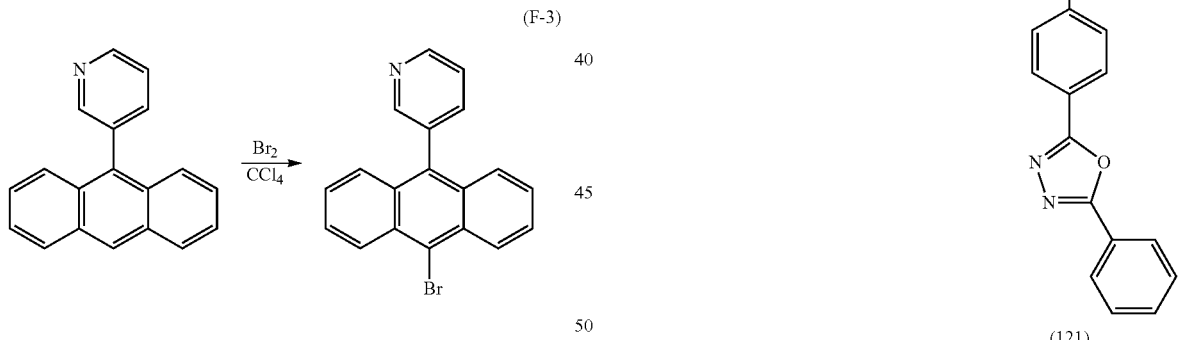

In a 100 mL three-necked flask were placed 0.66 g (2.0 mmol) of 3-(10-bromo-9-anthryl)pyridine, 0.63 g (2.4 mmol) of 4-(5-phenyl-1,3,4-oxadiazol-2-yl)phenylboronic acid, 0.45 g (4.0 mmol) of sodium carbonate, 25 mL of toluene, 3 mL of water, and 6 mL of ethanol. The mixture was degassed by being stirred under reduced pressure, and the atmosphere in the flask was replaced with nitrogen. To this mixture was added 58 mg (0.050 mmol) of tetrakis(triphenylphosphine)palladium(0), and the resulting mixture was refluxed under a nitrogen stream at 120° C. for 23 hours. After a predetermined time has passed, water was added to this mixture, and the aqueous layer was extracted with ethyl acetate. The obtained extract and the organic layer were combined and washed with saturated brine, and then the organic layer was dried with magnesium sulfate. The obtained mixture was subjected to gravity filtration, and the resulting filtrate was concentrated to give a solid. The obtained solid was purified by silica gel column chromatography (a 5:1 ratio of toluene to ethyl acetate). Recrystallization from a mixed solvent of toluene and hexane gave 0.65 g of a solid in 69% yield, which was the desired substance.

Under conditions of a temperature of 240° C., an argon stream (at a flow rate of 3.0 mL/min), and a pressure of 10 Pa, 0.66 g of the desired substance obtained above was subjected to sublimation purification for 18 hours. Accordingly, 0.51 g of the desired substance was obtained in 77% yield.

The compound obtained through the above synthesis method was examined by a nuclear magnetic resonance (NMR) method. The measurement data are shown below. $^1$H NMR (CDCl$_3$, 300 MHz): δ(ppm)=7.38-7.43 (m, 4H), 7.57-7.74 (m, 10H), 7.83-7.87 (m, 1H), 8.20-8.24 (m, 2H), 8.42 (d, J=8.7 Hz, 2H), 8.76 (d, J=1.8 Hz, 1H), 8.85 (dd, J=4.8 Hz, 1.8 Hz, 1H).

Figure 11A:
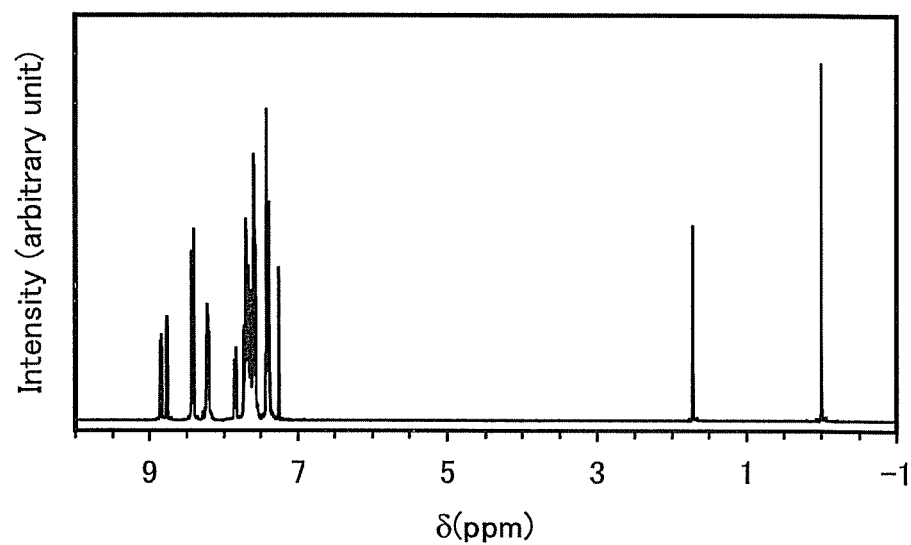
FIGS. 11A and 11B show $^1$H NMR charts of PyAO11 represented by Structural Formula (121).
Figure 11B:
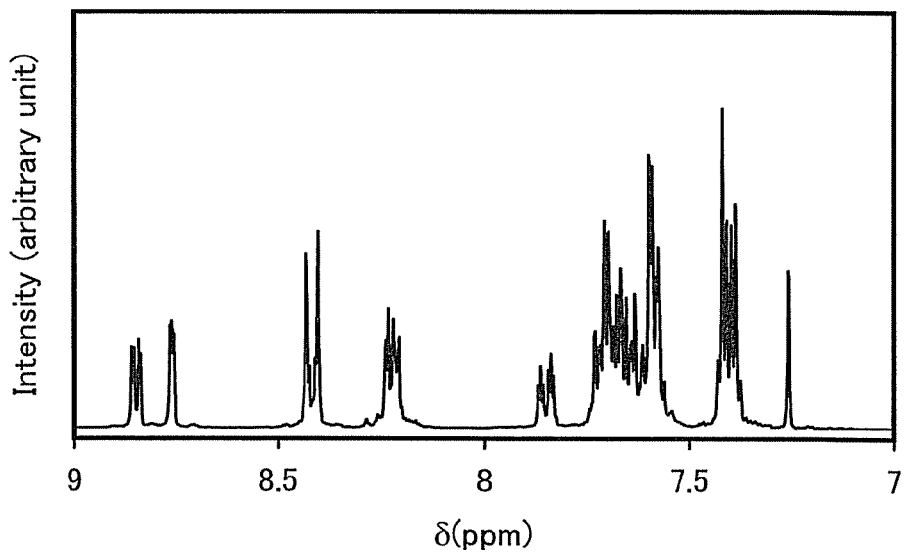

In addition, FIGS. 11A and 11B show $^1$H NMR charts. Note that FIG. 11B is a chart showing an enlarged part in the range of 7.0 ppm to 9.0 ppm in FIG. 11A. The measurement results demonstrate that this compound is 3-{10-[4-(5-phenyl-1,3,4-oxadiazol-2-yl)phenyl]-9-anthryl}pyridine (abbreviation: PyAO11), the oxadiazole derivative represented by the above Structural Formula (121) which is one embodiment of the present invention.

Figure 12A:
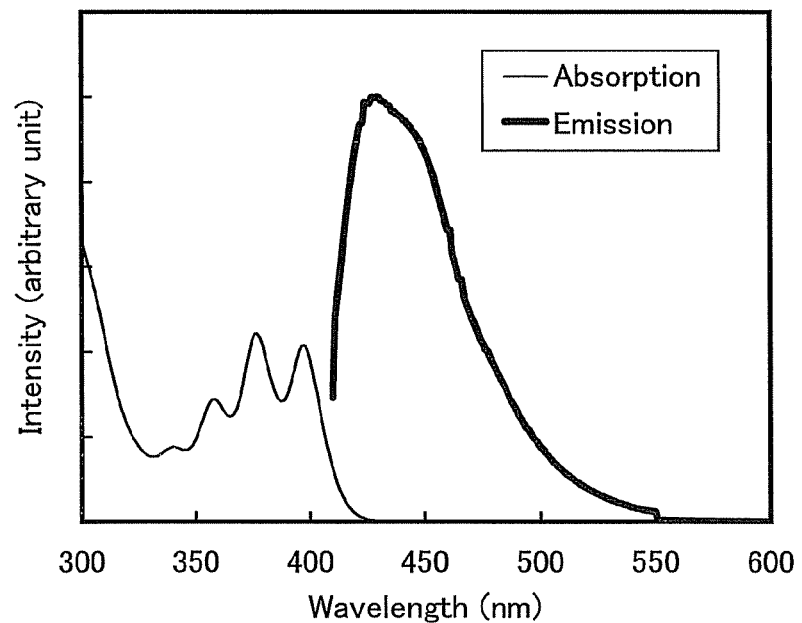
FIGS. 12A and 12B show an ultraviolet-visible absorption spectrum and an emission spectrum of PyAO11 represented by Structural Formula (121).
Figure 12B:
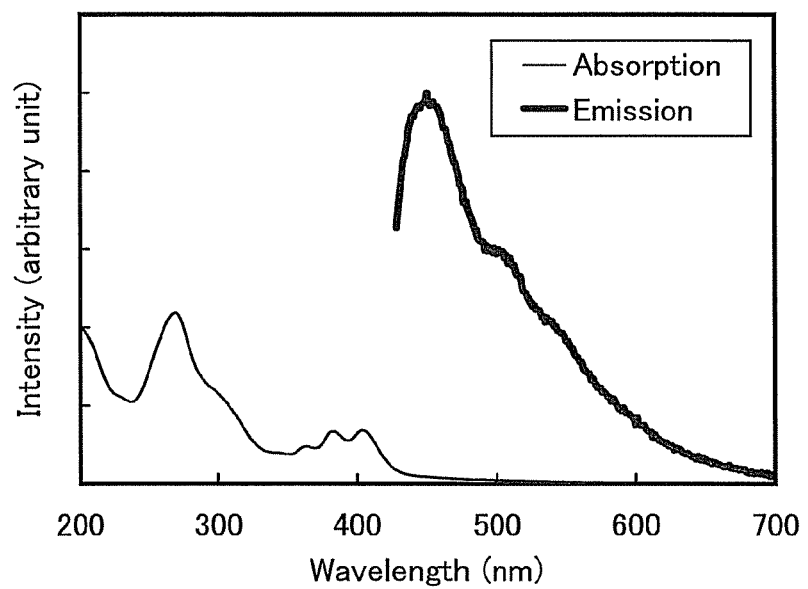

Further, FIG. 12A shows an absorption spectrum of a toluene solution of PyAO11, and FIG. 12B shows an absorption spectrum of a thin film of PyAO11. An ultraviolet-visible spectrophotometer (V-550, manufactured by JASCO Corporation) was used for the measurements. To measure the absorption spectrum of the toluene solution of PyAO11, the toluene solution was put into a quartz cell, and the absorption spectra of quartz and toluene were subtracted from that of the toluene solution in the quartz cell. Further, to measure the absorption spectrum of the thin film of PyAO11, a sample was formed by evaporation of PyAO11 onto a quartz substrate, and the absorption spectrum of quartz was subtracted from that of the sample.

In FIG. 12A and FIG. 12B, the horizontal axis represents wavelength (nm) and the vertical axis represents absorption intensity (arbitrary unit). The absorption peak of the toluene solution was at 397 nm, while the absorption peak of the thin film was at 404 nm.

Further, FIG. 12A shows an emission spectrum of a toluene solution of PyAO11 (an excitation wavelength of 397 nm), while FIG. 12B shows an emission spectrum of a thin film of PyAO11 (an excitation wavelength of 401 nm). In FIG. 12A and FIG. 12B, the horizontal axis represents wavelength (nm) and the vertical axis also represents emission intensity (arbitrary unit). The maximum emission wavelength of the toluene solution was 429 nm (excitation wavelength of 397 nm), while the maximum emission wavelength of the thin film was 451 nm (excitation wavelength of 401 run).

Furthermore, by measurement with a photoelectron spectrometer (AC-2, manufactured by Riken Keiki, Co., Ltd.) in the atmosphere, the ionization potential of the thin film of PyAO11 was found to be 5.78 eV. As a result, the HOMO level was found to be −5.78 eV. Moreover, using data on the absorption spectrum of the thin film of PyAO11, the absorption edge was obtained from Tauc plot, with an assumption of direct transition. The absorption edge was estimated as an optical energy gap, whereby the energy gap was found to be 2.93 eV. The LUMO level was calculated from the obtained values of the energy gap and the HOMO level, and found to be −2.85 eV.

In addition, the oxidation-reduction characteristics of PyAO11 were measured. Cyclic voltammetry (CV) was employed. Note that an electrochemical analyzer (ALS model 600A, a product of BAS Inc.) was used for the measurements.

For a solution used in the CV measurements, dehydrated dimethylformamide (DMF, produced by Sigma-Aldrich Inc., 99.8%, Catalog No. 22705-6) was used as a solvent. Tetra-n-butylammonium perchlorate (n-Bu$_4$NClO$_4$, produced by Tokyo Chemical Industry Co., Ltd., Catalog No. T0836), which was a supporting electrolyte, was dissolved in the solvent such that the concentration of tetra-n-butylammonium perchlorate was 100 mmol/L. Furthermore, PyAO11, which was to be measured, was dissolved in the solution such that the concentration thereof was 2 mmol/L. In addition, a platinum electrode (PTE platinum electrode, produced by BAS Inc.) was used as a working electrode, a platinum electrode (Pt counter electrode for VC-3, (5 cm), produced by BAS Inc.) was used as an auxiliary electrode, and an Ag/Ag$^+$ electrode (RE-7 reference electrode for nonaqueous solvent, produced by BAS Inc.) was used as a reference electrode. Note that the measurements were conducted at room temperature.

The oxidation characteristics of PyAO11 were examined by 100 cycles of measurements in which a scan for changing the potential of the working electrode with respect to the reference electrode from 0 V to 1.20 V and then from 1.20 V to 0 V was set to one cycle. Further, the reduction characteristics of PyAO11 were examined by 100 cycles of measurements in which a scan for changing the potential of the working electrode with respect to the reference electrode from −1.33 V to −2.45 V and then from −2.45 V to −1.33 V was set to one cycle. Note that the scan rate for the CV measurements was set to 0.1 V/s.

The results reveal that there are no significant changes in the peak position and peak intensity of the CV curve in the oxidation-reduction reactions even after the 100 cycles of measurements. Accordingly, it is found that PyAO11, the oxadiazole derivative which is one embodiment of the present invention, is extremely stable to repetitive oxidation-reduction reactions.

Example 3

In Example 3, a method of synthesizing 2,2'-(2-tert-butylanthracene-9,10-diyldi-4,1-phenylene)bis(5-phenyl-1,3,4-oxadiazole) (abbreviation: tO112A), the oxadiazole derivative represented by Structural Formula (158) which is one embodiment of the present invention, will be specifically described.

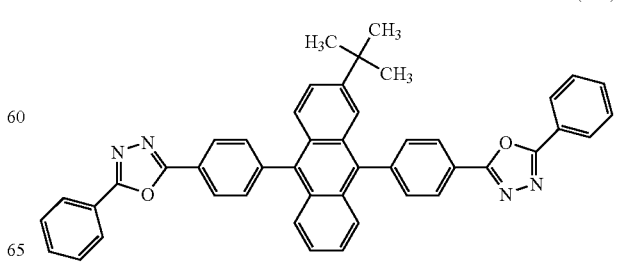

(158)

Step 1: Synthesis of 2-Tert-butyl-9,10-bis[4-(5-phenyl-1,3,4-oxadiazol-2-yl)phenyl]anthracene-9-10-diol The synthetic scheme of 2-tert-butyl-9,10-bis[4-(5-phenyl-1,3,4-oxadiazol-2-yl)phenyl]anthracene-9-10-diol is shown in (G-1).

In a 500 mL three-necked flask was placed 5.0 g (17 mmol) of 2-(4-bromophenyl)-5-phenyl-1,3,4-oxadiazole, and the atmosphere in the flask was replaced with nitrogen. Then, 100 mL of tetrahydrofuran (abbreviation: THF) was added to this mixture. This solution was cooled to −78° C., followed by addition of 13 mL (20 mmol) of a 1.5 mol/L hexane solution of n-butyllithium. This mixture was stirred under a nitrogen stream at −78° C. for 2 hours. Then, a solution in which 2.0 g (7.6 mmol) of 2-tert-butylanthraquinone was dissolved in tetrahydrofuran was added to this mixture a little at a time. This mixture was stirred at room temperature for 24 hours. Then, water was added to the reaction solution and the resulting mixture was stirred, followed by separation of the organic layer from the aqueous layer. The organic layer and the extract were combined and washed with saturated brine, and then the organic layer was dried with magnesium sulfate. Then, this mixture was suction filtered, and the resulting filtrate was concentrated to give a brown oily substance.

Step 2: Synthesis of 2,2′-(2-Tert-butyl-9,10-anthracenediyldi-4,1-phenylene)bis(5-phenyl-1,3,4-oxadiazole)

The synthetic scheme of 2,2′-(2-tert-butyl-9,10-anthracenediyldi-4,1-phenylene)bis(5-phenyl-1,3,4-oxadiazole) is shown in (G-2).

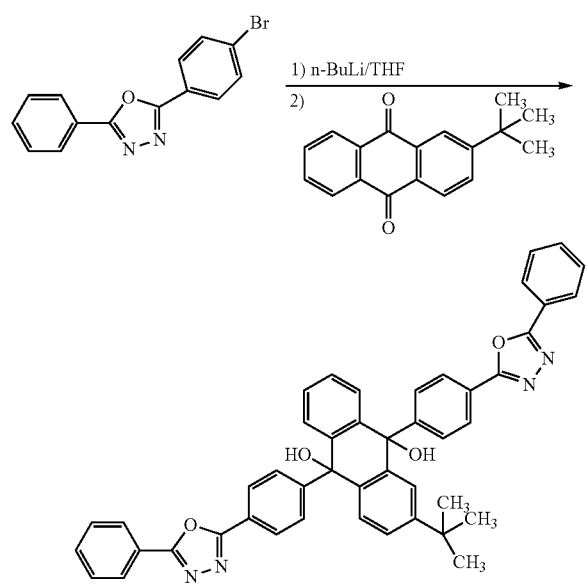

(G-1)

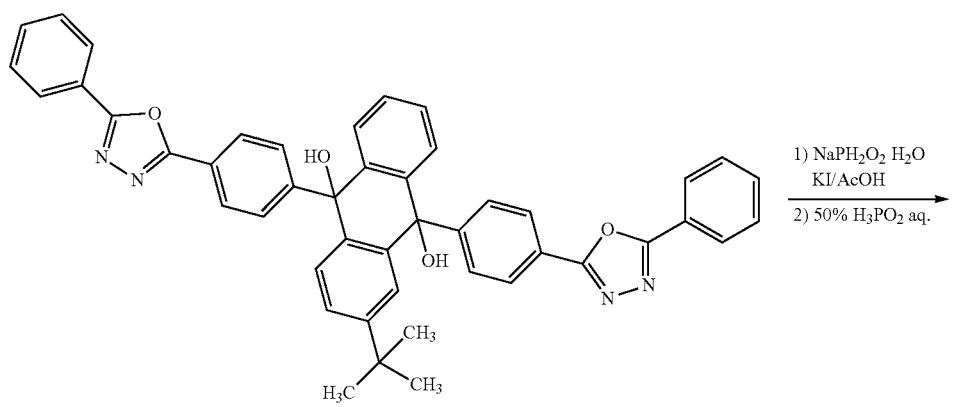

(G-2)

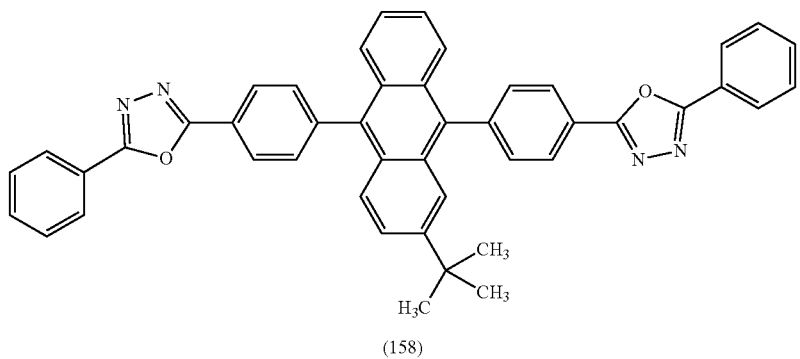

(158)

In a recovery flask were placed 2-tert-butyl-9,10-bis[4-(5-phenyl-1,3,4-oxadiazol-2-yl)phenyl]anthracene-9,10-diol, 6.0 g (36 mmol) of potassium iodide, and 29 g (83 mmol) of sodium phosphinate monohydrate. They are dissolved by the addition of 50 mL of glacial acetic acid. This solution was stirred at 120° C. for 4 hours. Then, 50 mL of a 50% solution of phosphinic acid was added to this solution, and the mixture was stirred at 120° C. for 1 hour. Then, an aqueous solution of sodium hydrogen carbonate was added to this mixture, followed by stirring. After that, the resulting mixture was suction filtered to give a solid. This solid was washed with ethyl acetate. After that, the resulting solid was dissolved in chloroform, and this solution was washed with a saturated aqueous solution of sodium hydrogen carbonate and with saturated brine. Then, magnesium sulfate was added to the organic layer to thy it.

After being dried, this mixture was suction filtered. The resulting filtrate was concentrated to give a compound, which was purified by silica gel column chromatography. The column chromatography was performed first using a mixed solvent of a 1:1 ratio of toluene to hexane as a developing solvent and then using a mixed solvent of a 5:1 ratio of toluene to ethyl acetate as a developing solvent. The fractions obtained were concentrated to give a solid. Recrystallization of this solid from a mixed solvent of chloroform and ethyl acetate gave 1.8 g of a pale yellow powdered solid in 35% yield in the two steps, which was the desired substance.

By a train sublimation method, 1.8 g of the obtained solid was purified. Under a reduced pressure of 7.0 Pa with a flow rate of argon at 3.0 mL/min, the sublimation purification was carried out at 320° C. for 17 hours. The amount of the compound was 1.6 g, and the yield thereof was 89%.

The compound obtained through the above synthesis method was examined by a nuclear magnetic resonance (NMR) method. The measurement data are shown below. $^1$H NMR (CDCl$_3$, 300 MHz): δ(ppm)=1.28 (s, 9H), 7.35-7.39 (m, 2H), 7.48-7.72 (m, 15H), 8.21-8.24 (m, 4H), 8.39-8.45 (m, 4H).

Figure 13A:
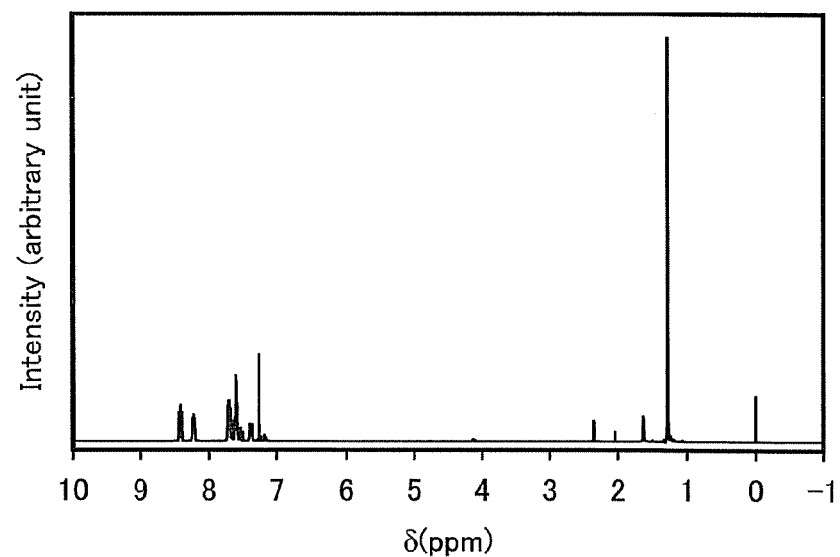
FIGS. 13A and 13B show $^1$H NMR charts of tO112A represented by Structural Formula (158).
Figure 13B:
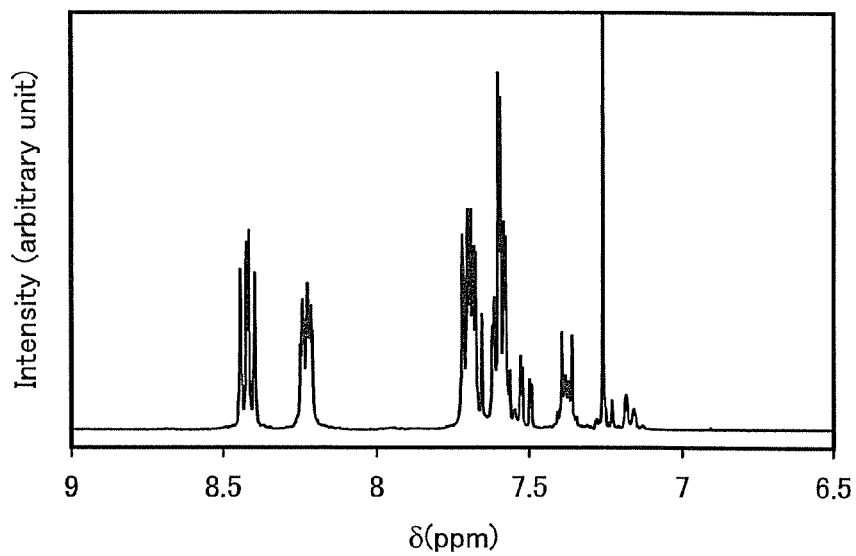

In addition, FIGS. 13A and 13B show $^1$H NMR charts. Note that FIG. 13B is a chart showing an enlarged part in the range of 6.5 ppm to 9.0 ppm in FIG. 13A. The measurement results demonstrate that this compound is 2,2'-(2-tert-butylanthracene-9,10-diyldi-4,1-phenylene)bis(5-phenyl-1,3,4-oxadiazole) (abbreviation: tO112A), the oxadiazole derivative represented by the above Structural Formula (158) which is one embodiment of the present invention.

Figure 14A:
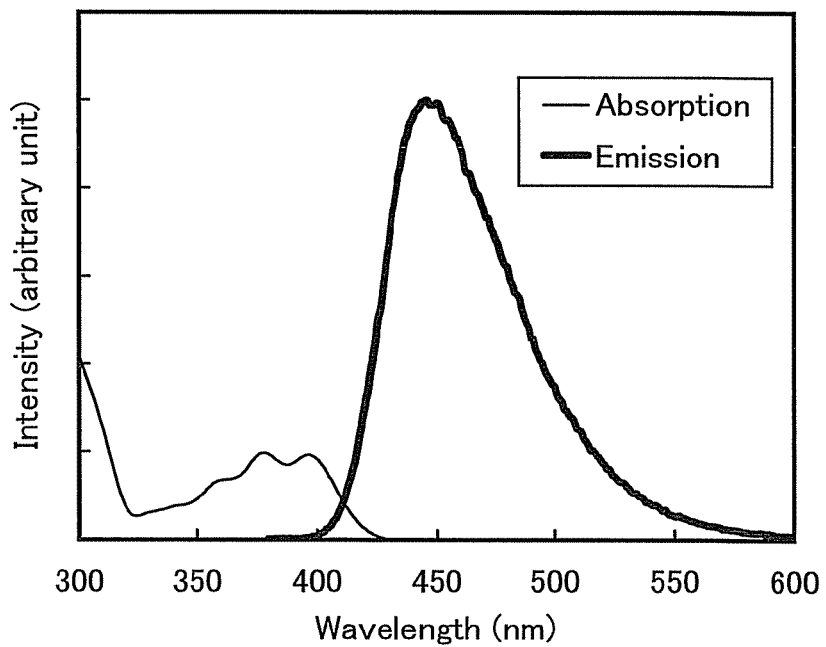
FIGS. 14A and 14B show an ultraviolet-visible absorption spectrum and an emission spectrum of tO112A represented by Structural Formula (158).
Figure 14B:
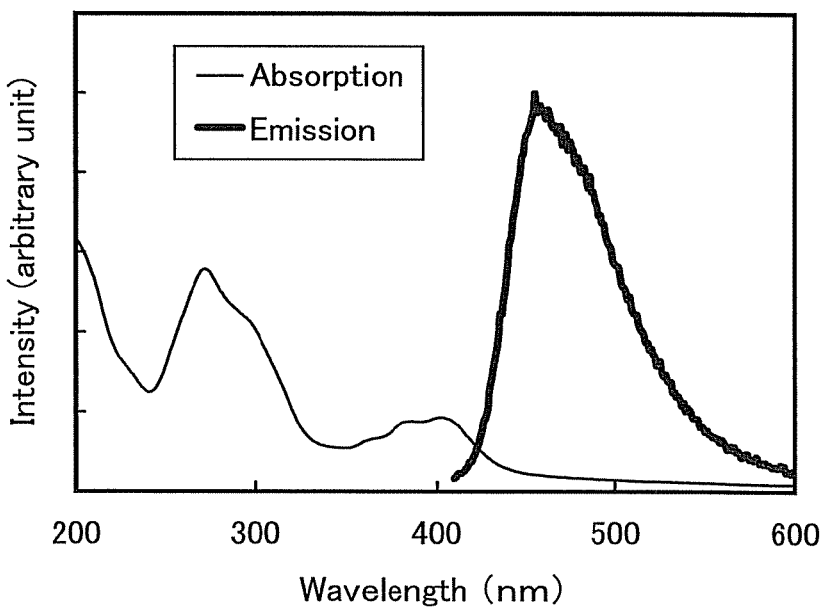

Further, FIG. 14A shows an absorption spectrum of a toluene solution of tO112A, and FIG. 14B shows an absorption spectrum of a thin film of tO112A. An ultraviolet-visible spectrophotometer (V-550, manufactured by JASCO Corporation) was used for the measurements. To measure the absorption spectrum of the toluene solution of tO112A, the toluene solution was put into a quartz cell, and the absorption spectra of quartz and toluene were subtracted from that of the toluene solution in the quartz cell. Further, to measure the absorption spectrum of the thin film of tO112A, a sample was formed by evaporation of tO112A onto a quartz substrate, and the absorption spectrum of quartz was subtracted from that of the sample.

In FIG. 14A and FIG. 14B, the horizontal axis represents wavelength (nm) and the vertical axis represents absorption intensity (arbitrary unit). The absorption peak of the toluene solution was at 396 nm, while the absorption peak of the thin film was at 402 nm.

Further, FIG. 14A shows an emission spectrum of a toluene solution of tO112A (an excitation wavelength of 374 nm), while FIG. 14B shows an emission spectrum of a thin film of tO112A (an excitation wavelength of 402 nm). In FIG. 14A and FIG. 14B, the horizontal axis represents wavelength (nm) and the vertical axis also represents emission intensity (arbitrary unit). The maximum emission wavelength of the toluene solution was 446 nm (excitation wavelength of 374 nm), while the maximum emission wavelength of the thin film was 456 nm (excitation wavelength of 402 nm).

Furthermore, by measurement with a photoelectron spectrometer (AC-2, manufactured by Riken Keiki, Co., Ltd.) in the atmosphere, the ionization potential of the thin film of tO112A was found to be 5.78 eV. As a result, the HOMO level was found to be −5.78 eV. Moreover, using data on the absorption spectrum of the thin film of tO112A, the absorption edge was obtained from Tauc plot, with an assumption of direct transition. The absorption edge was estimated as an optical energy gap, whereby the energy gap was found to be 2.87 eV. The LUMO level was calculated from the obtained values of the energy gap and the HOMO level, and found to be −2.91 eV.

In addition, the oxidation-reduction characteristics of tO112A were measured. Cyclic voltammetry (CV) was employed. Note that an electrochemical analyzer (ALS model 600A, a product of BAS Inc.) was used for the measurements.

For a solution used in the CV measurements, dehydrated dimethylformamide (DMF, produced by Sigma-Aldrich Inc., 99.8%, Catalog No. 22705-6) was used as a solvent. Tetra-n-butylammonium perchlorate (n-Bu$_4$NClO$_4$, produced by Tokyo Chemical Industry Co., Ltd., Catalog No. T0836), which was a supporting electrolyte, was dissolved in the solvent such that the concentration of tetra-n-butylammonium perchlorate was 100 mmol/L. Furthermore, tO112A, which was to be measured, was dissolved in the solution such that the concentration thereof was 2 mmol/L. In addition, a platinum electrode (PTE platinum electrode, produced by BAS Inc.) was used as a working electrode, a platinum electrode (Pt counter electrode for VC-3, (5 cm), produced by BAS Inc.) was used as an auxiliary electrode, and an Ag/Ag$^+$ electrode (RE-5 reference electrode for nonaqueous solvent, produced by BAS Inc.) was used as a reference electrode. Note that the measurements were conducted at room temperature.

The oxidation characteristics of tO112A were examined by 100 cycles of measurements in which a scan for changing the potential of the working electrode with respect to the reference electrode from −0.32 V to 1.30 V and then from 1.30 V to −0.32 V was set to one cycle. Further, the reduction characteristics of tO112A were examined by 100 cycles of measurements in which a scan for changing the potential of the working electrode with respect to the reference electrode from −0.21 V to −2.40 V and then from −2.40 V to −0.21 V was set to one cycle. Note that the scan rate for the CV measurements was set to 0.1 V/s.

The results reveal that there are no significant changes in the peak position and peak intensity of the CV curve in the oxidation-reduction reactions even after the 100 cycles of measurements. Accordingly, it is found that tO112A, the oxadiazole derivative which is one embodiment of the present invention, is extremely stable to repetitive oxidation-reduction reactions.

Example 4

In this example, description is provided of a method of forming a light-emitting element including any of the oxadiazole derivatives described in Embodiment 1 as an electron-transport material of an electron-transport layer, and of measurement results of the element characteristics. Specifically, Light-Emitting Element 1 formed using 2-phenyl-5-[4-(10-phenyl-9-anthryl)phenyl]-1,3,4-oxadiazole (abbreviation: O11PhA), which is described in Example 1, will be described.

Figure 8:
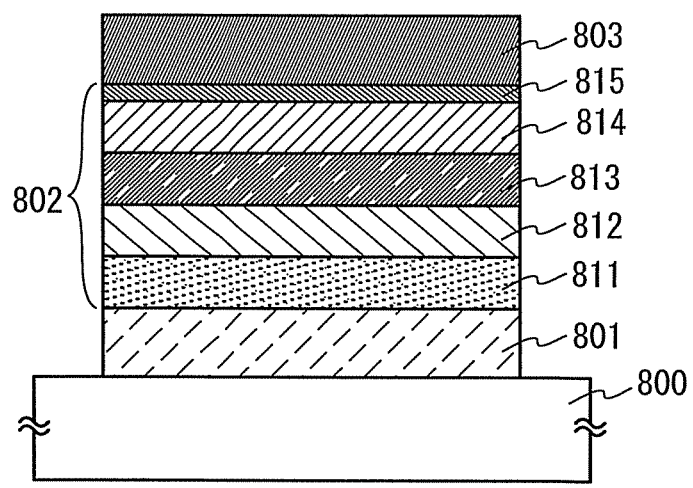
FIG. 8 illustrates a light-emitting element which is one embodiment of the present invention.

Note that FIG. 8 illustrates an element structure of the light-emitting element of this example in which an electron-transport layer 814 is formed using one of the above-described oxadiazole derivatives which are embodiments of the present invention. Organic compounds used in this example are represented by Structural Formulas (i) to (iv) below. In addition, the element structure of the light-emitting element will be described with reference to FIG. 8.

(i)

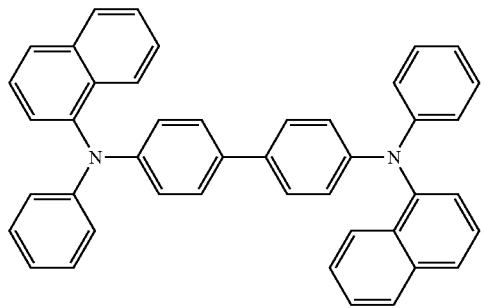

NPB (ii)

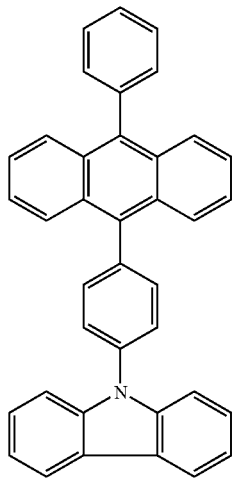

CzPA (iii)

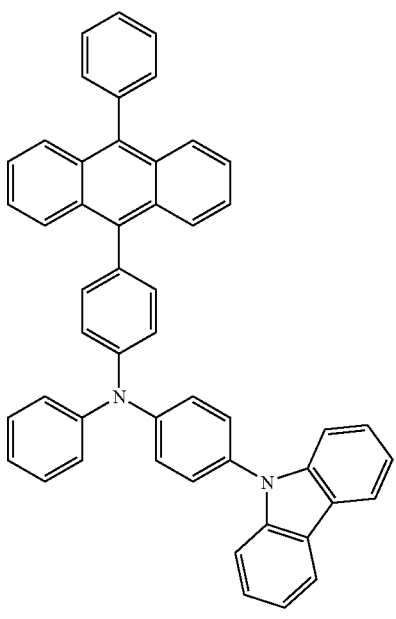

YGAPA

-continued (iv)

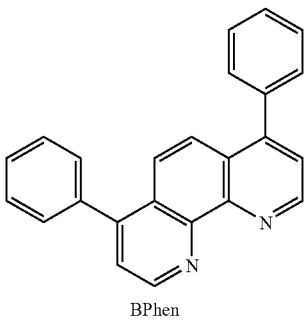

BPhen

<<Fabrication of Light-Emitting Element 1>>

First, as a first electrode 801, a 110 nm-thick film of indium tin oxide containing silicon oxide (ITSO) is formed over a substrate 800 made of glass. Note that the periphery of the ITSO film is covered with an insulating film so that a portion of a surface of the film which is 2 mm square is exposed. Here, the first electrode 801 is an electrode that functions as an anode of the light-emitting element.

Next, as pretreatment for forming the light-emitting element over the substrate 800, the surface of the substrate was washed with water using a porous resin brush, baked at 200° C. for one hour, and subjected to UV ozone treatment for 370 seconds.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 800 was cooled down for about 30 minutes.

Next, the glass substrate 800 provided with the first electrode 801 was fixed to a substrate holder provided in a vacuum evaporation system so that a surface on which the first electrode 801 was formed was placed downward. In this example, a case will be described in which a hole-injection layer 811, a hole-transport layer 812, a light-emitting layer 813, an electron-transport layer 814, and an electron-injection layer 815 which are included in an EL layer 802 are sequentially formed by a vacuum evaporation method.

After the pressure in the vacuum deposition apparatus was reduced to $10^{-4}$ Pa, NPB, which was represented by the above Structural Formula (i), and molybdenum(VI) oxide were co-evaporated with the ratio of NPB to molybdenum(VI) oxide being 4:1 (mass ratio), whereby the hole-injection layer 811 was formed. The thickness thereof was 50 nm. Note that the co-evaporation method refers to an evaporation method in which some different substances are evaporated from some different evaporation sources simultaneously.

Next, NPB was evaporated to a thickness of 10 nm as the hole-transport layer 812.

Next, the light-emitting layer 813 was formed over the hole-transport layer 812. Over the hole-transport layer 812, CzPA and YGAPA, which were respectively represented by the above Structural Formulas (ii) and (iii), were co-evaporated with the ratio of CzPA to YGAPA being 1:0.04 (mass ratio); thus, the light-emitting layer 813 was formed. The thickness thereof was 30 nm.

Next, O11PhA, which was synthesized in Example 1 and represented by Structural Formula (100), was evaporated to a thickness of 10 nm, and then Bphen, which was represented by the above Structural Formula (iv), was evaporated to a thickness of 20 nm, whereby the electron-transport layer 814 was formed. Furthermore, lithium fluoride was evaporated to a thickness of 1 nm over the electron-transport layer 814, whereby the electron-injection layer 815 was formed.

Next, a 200-nm-thick film of aluminum was formed as a second electrode 803. Thus, Light-emitting Element 1, which was one embodiment of the present invention, was obtained. Note that the second electrode 803 is an electrode that functions as a cathode. A resistance heating method was applied to all the above evaporation processes.

Further, this light-emitting element was sealed in a glove box containing a nitrogen atmosphere so as not to be exposed to air.

Note that the following Table 1 shows the element structure of Light-emitting Element 1 which was fabricated.

TABLE 1

| | first electrode 801 | hole-injection layer 811 | hole-transport layer 812 | light-emitting layer 813 | electron-transport layer 814 | electron-injection layer 815 | second electrode 803 |
|---|---|---|---|---|---|---|---|
| Light-emitting Element 1 | ITSO 110 nm | NPB:MoOx (4:1) 50 nm | NPB 10 nm | CzPA:YGAPA (1:0.04) 30 nm | O11PhA 10 nm | BPhen 20 nm | LiF 1 nm | Al 200 nm |

<<Operation Characteristics of Light-Emitting Element 1>>

Operation characteristics of the fabricated Light-emitting Element 1 were measured. Note that the measurements were carried out at room temperature (in the atmosphere kept at 25° C.).

Figure 15:
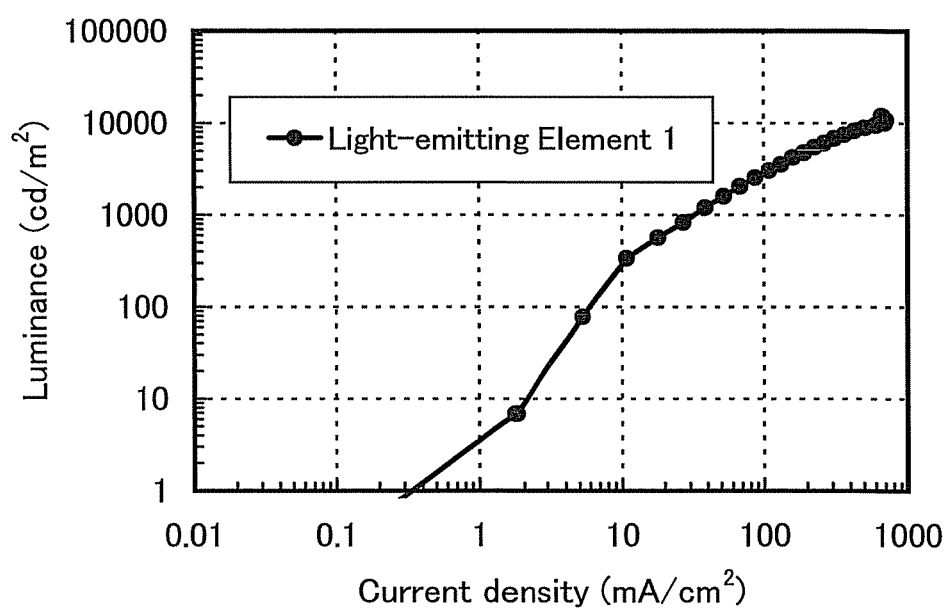
FIG. 15 shows current density vs. luminance characteristics of Light-emitting Element 1.
Figure 16:
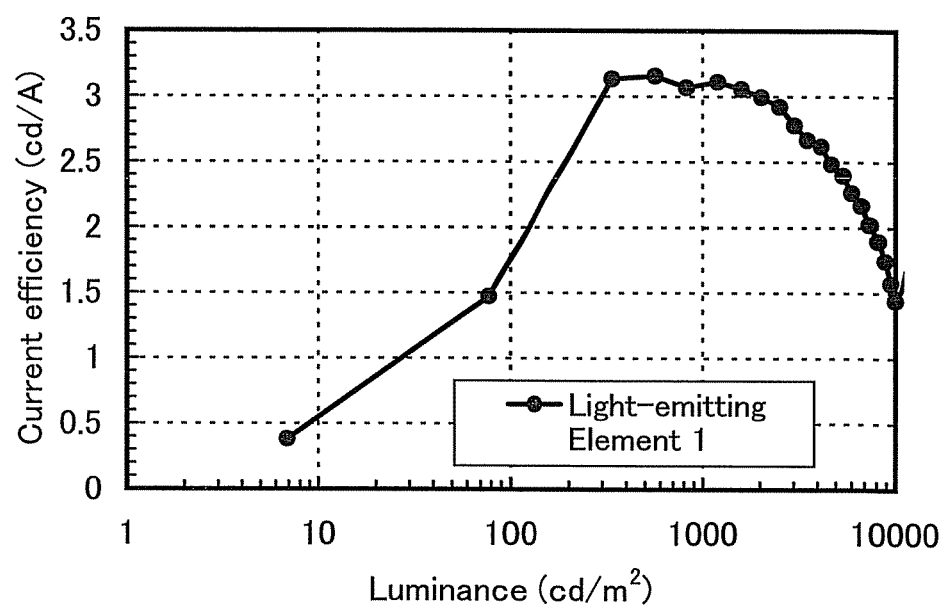
FIG. 16 shows luminance vs. current efficiency characteristics of Light-emitting Element 1.
Figure 17:
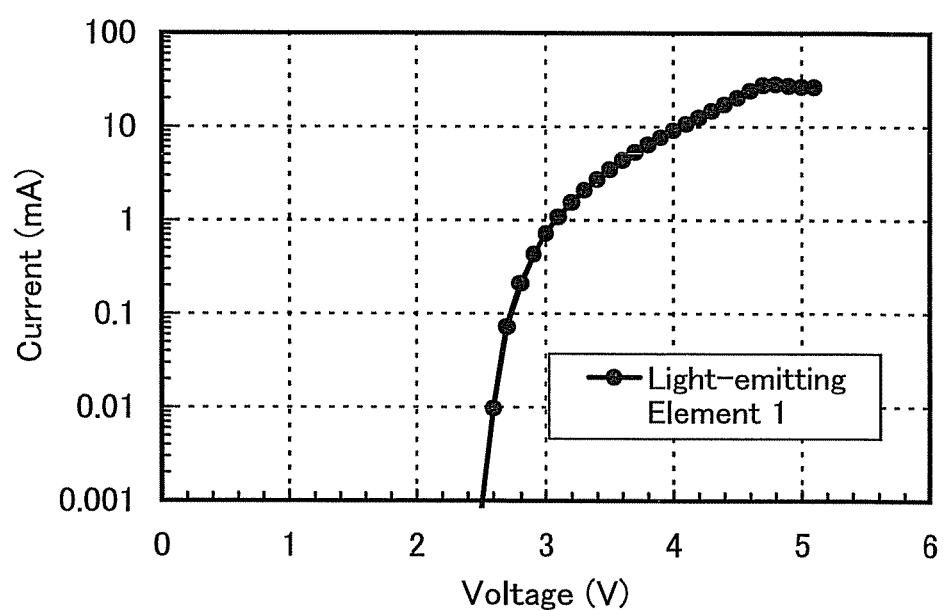
FIG. 17 shows voltage vs. current characteristics of Light-emitting Element 1.

FIG. 15 shows current density vs. luminance characteristics of Light-emitting Element 1. Note that in FIG. 15, the vertical axis represents luminance ($cd/m^2$) and the horizontal axis represents current density ($mA/cm^2$). In addition, FIG. 16 shows luminance vs. current efficiency characteristics of Light-emitting Element 1. Note that in FIG. 16, the vertical axis represents current efficiency (cd/A) and the horizontal axis represents luminance ($cd/m^2$). Further, FIG. 17 shows voltage vs. current characteristics of Light-emitting Element 1. Note that in FIG. 17, the vertical axis represents current (mA) and the horizontal axis represents voltage (V).

As can be seen from the operation characteristics shown above, Light-emitting Element 1 exhibits sufficient current efficiency as a light-emitting element. This demonstrates that the light-emitting element formed using the oxadiazole derivative according to one embodiment of the present invention has high current efficiency.

Figure 18:
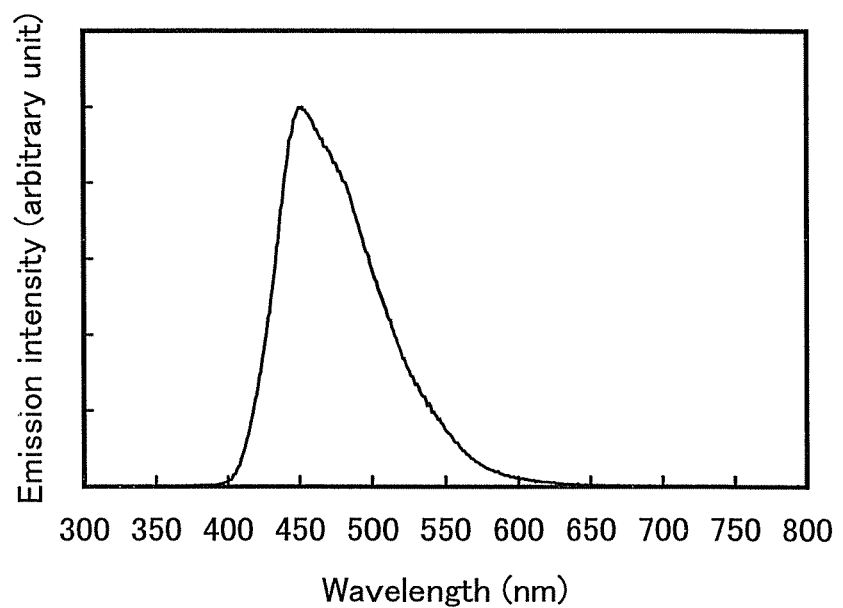
FIG. 18 shows an emission spectrum of Light-emitting Element 1.

FIG. 18 shows the emission spectrum of Light-emitting Element 1 which was obtained by applying a current at a current density of 1 $mA/cm^2$. As apparent from FIG. 18, the emission spectrum of Light-emitting Element 1 has a peak at about 450 nm. This indicates that the emission spectrum of Light-emitting Element 1 is exhibited by light emission of YGAPA which is included in the light-emitting layer 813.

Example 5

In this example, Light-emitting Element 2 was fabricated such that a difference in element structure between it and Light-emitting Element 1 described in Example 4 was a material for forming the light-emitting layer 813. In addition, element characteristics of Light-emitting Element 2 were measured. Specifically, Alq and coumarin 6, which were respectively represented by Structural Formulas (v) and (vi) shown below, were co-evaporated with the ratio of Alq to coumarin 6 being 1:0.01 (mass ratio); thus, the light-emitting layer 813 was formed. The thickness thereof was 40 nm. Note that except for the light-emitting layer 813, the structure and formation method of the layers included in Light-emitting Element 2 are the same as those of Light-emitting Element 1, the description of which is found in Example 4 and omitted here. Further, organic compounds used in this example are represented by the following Structural Formulas (v) and (vi).

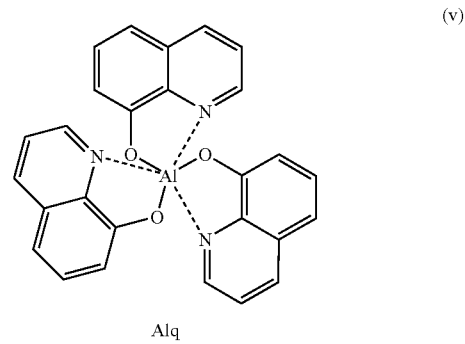

Alq (v)

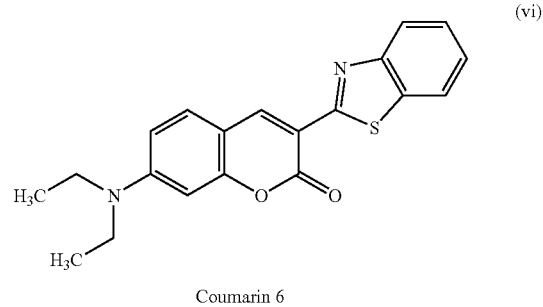

Coumarin 6 (vi)

Note that the following Table 2 shows the element structure of Light-emitting Element 2 which was fabricated.

TABLE 2

| | first electrode 801 | hole-injection layer 811 | hole-transport layer 812 | light-emitting layer 813 | electron-transport layer 814 | electron-injection layer 815 | second electrode 803 |
|---|---|---|---|---|---|---|---|
| Light-emitting Element 2 | ITSO 110 nm | NPB:MoOx (4:1) 50 nm | NPB 10 nm | Alq:coumarin 6 (1:0.01) 40 nm | O11PhA 10 nm | BPhen 20 nm | LiF 1 nm | Al 200 nm |

<<Operation Characteristics of Light-Emitting Element 2>>

Operation characteristics of the fabricated Light-emitting Element 2 were measured. Note that the measurements were carried out at room temperature (in the atmosphere kept at 25° C.).

Figure 19:
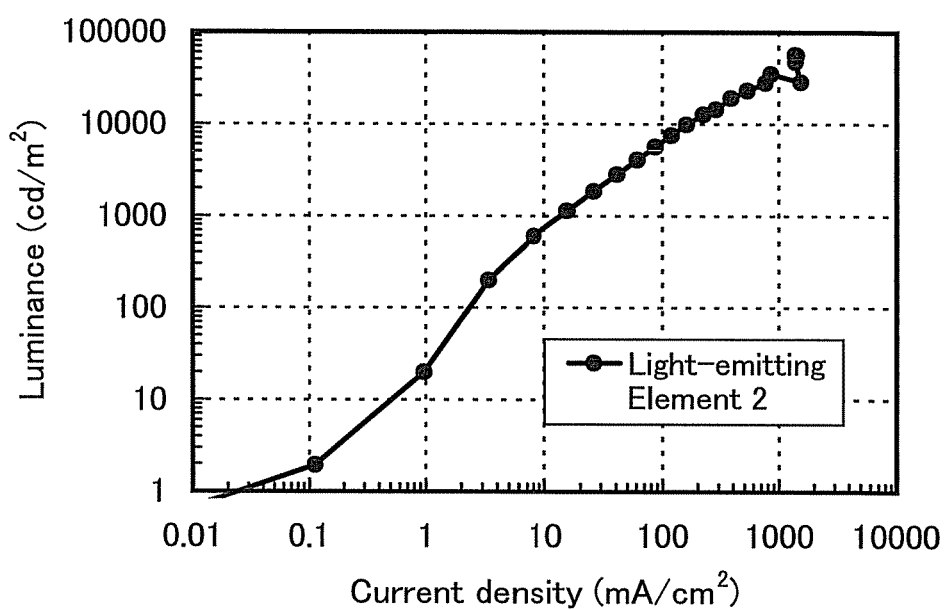
FIG. 19 shows current density vs. luminance characteristics of Light-emitting Element 2.
Figure 20:
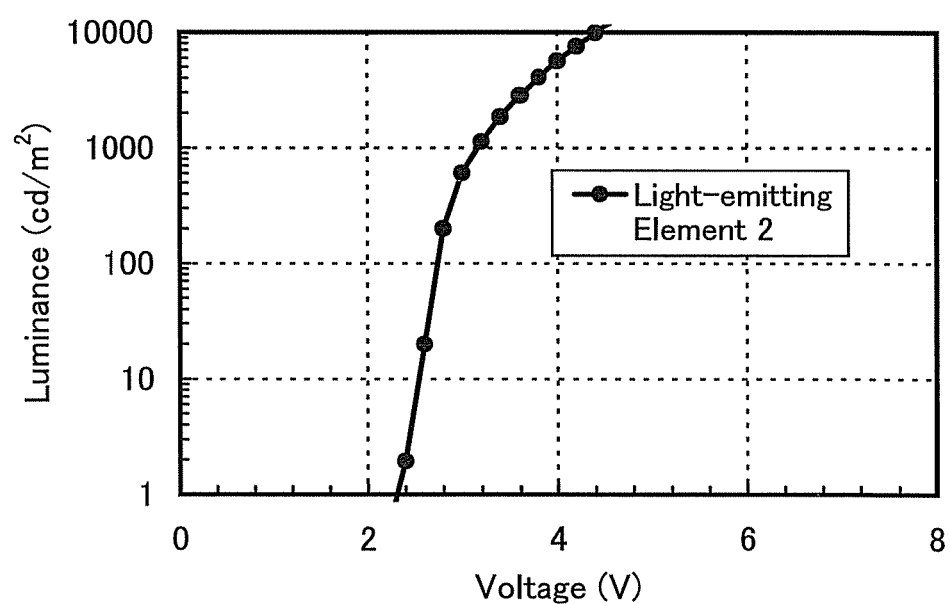
FIG. 20 shows voltage vs. luminance characteristics of Light-emitting Element 2.
Figure 21:
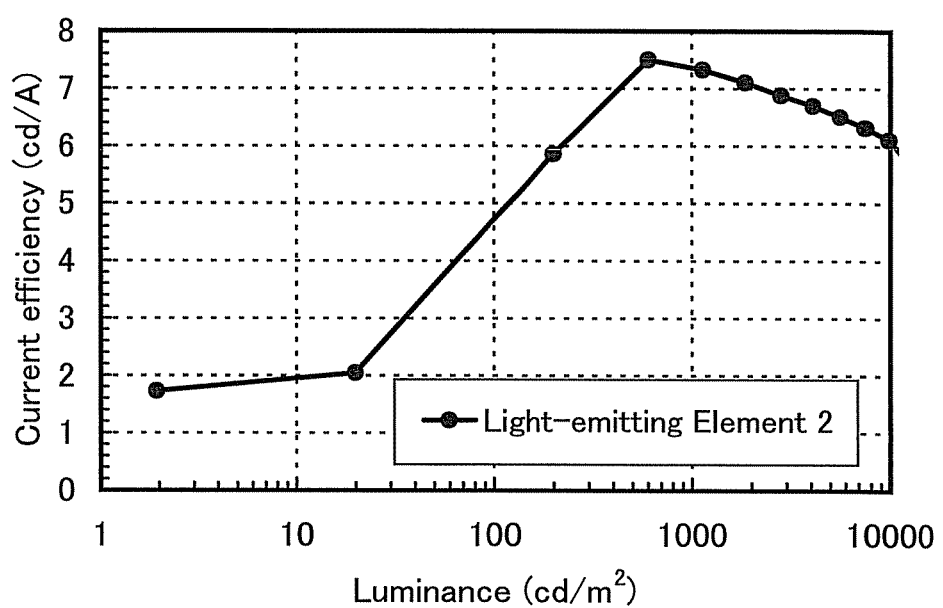
FIG. 21 shows luminance vs. current efficiency characteristics of Light-emitting Element 2.

FIG. 19 shows current density vs. luminance characteristics of Light-emitting Element 2. Note that in FIG. 19, the vertical axis represents luminance (cd/m$^2$) and the horizontal axis represents current density (mA/cm$^2$). Further, FIG. 20 shows voltage vs. luminance characteristics of Light-emitting Element 2. Note that in FIG. 20, the vertical axis represents luminance (cd/m$^2$) and the horizontal axis represents voltage (V). In addition, FIG. 21 shows luminance vs. current efficiency characteristics of Light-emitting Element 2. Note that in FIG. 21, the vertical axis represents current efficiency (cd/A) and the horizontal axis represents luminance (cd/m$^2$).

As can be seen from the operation characteristics shown above, Light-emitting Element 2 exhibits sufficient current efficiency as a light-emitting element. This demonstrates that the light-emitting element formed using the oxadiazole derivative according to one embodiment of the present invention has high current efficiency.

Figure 22:
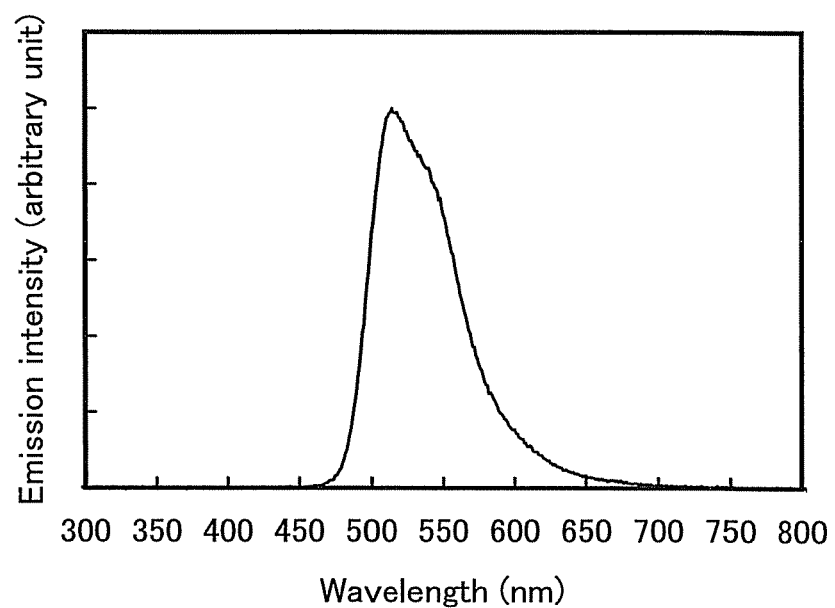
FIG. 22 shows an emission spectrum of Light-emitting Element 2.

FIG. 22 shows the emission spectrum of Light-emitting Element 2 which was obtained by applying a current at a current density of 1 mA/cm$^2$. As apparent from FIG. 22, the emission spectrum of Light-emitting Element 2 has a peak at 515 nm. This indicates that the emission spectrum of Light-emitting Element 2 is exhibited by light emission of coumarin 6, which is included in the light-emitting layer 813.

Example 6

In this example, Light-emitting Element 3 was fabricated such that differences in element structure between it and Light-emitting Element 1 described in Example 4 were materials for forming the light-emitting layer 813, the electron-transport layer 814, and the electron-injection layer 815. In addition, element characteristics of Light-emitting Element 3 were measured. Specifically, a 30-nm-thick film of O11PhA, which was synthesized in Example 1 and represented by Structural Formula (100), was formed as the light-emitting layer 813, and a 10-nm-thick film of Alq was formed as the electron-transport layer 814. As for the electron-injection layer 815, a 20-nm-thick film was formed by co-evaporation with the ratio of Alq to LiF being 1:0.01 (mass ratio). Note that except for the light-emitting layer 813, the electron-transport layer 814, and the electron-injection layer 815, the structure and formation method of the layers included in Light-emitting Element 3 are the same as those of Light-emitting Element 1, the description of which is found in Example 4 and omitted here.

Note that the following Table 3 shows the element structure of Light-emitting Element 3 which was fabricated.

TABLE 3

| | first electrode 801 | hole-injection layer 811 | hole-transport layer 812 | light-emitting layer 813 | electron-transport layer 814 | electron-injection layer 815 | second electrode 803 |
|---|---|---|---|---|---|---|---|
| Light-emitting Element 3 | ITSO 110 nm | NPB:MoOx (4:1) 50 nm | NPB 10 nm | O11PhA 30 nm | Alq 10 nm | Alq:Li (1:0.01) 20 nm | Al 200 nm |

<<Operation Characteristics of Light-Emitting Element 3>>

Operation characteristics of the fabricated Light-emitting Element 3 were measured. Note that the measurements were carried out at room temperature (in the atmosphere kept at 25° C.).

Figure 23:
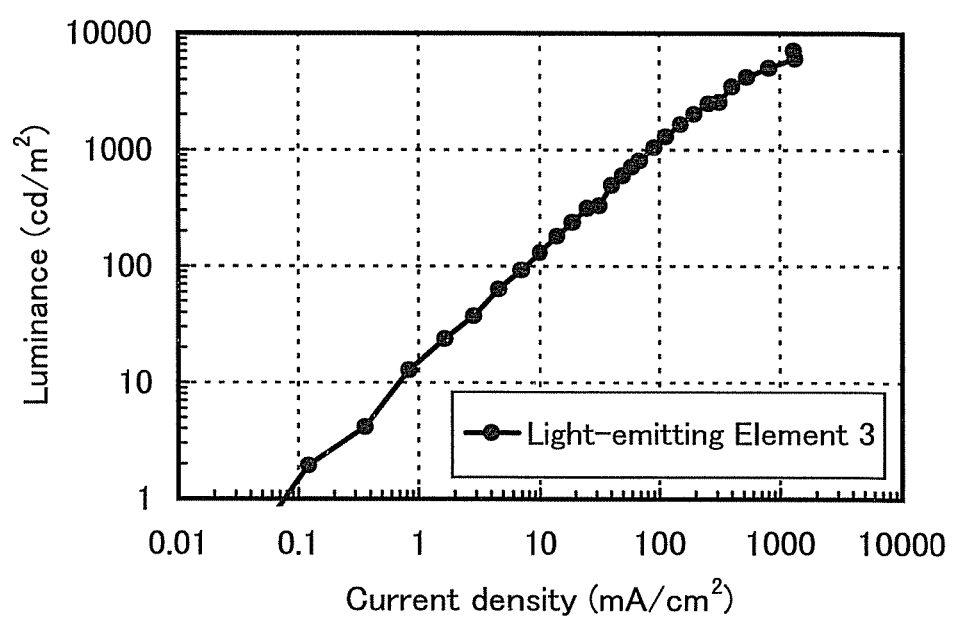
FIG. 23 shows current density vs. luminance characteristics of Light-emitting Element 3.
Figure 24:
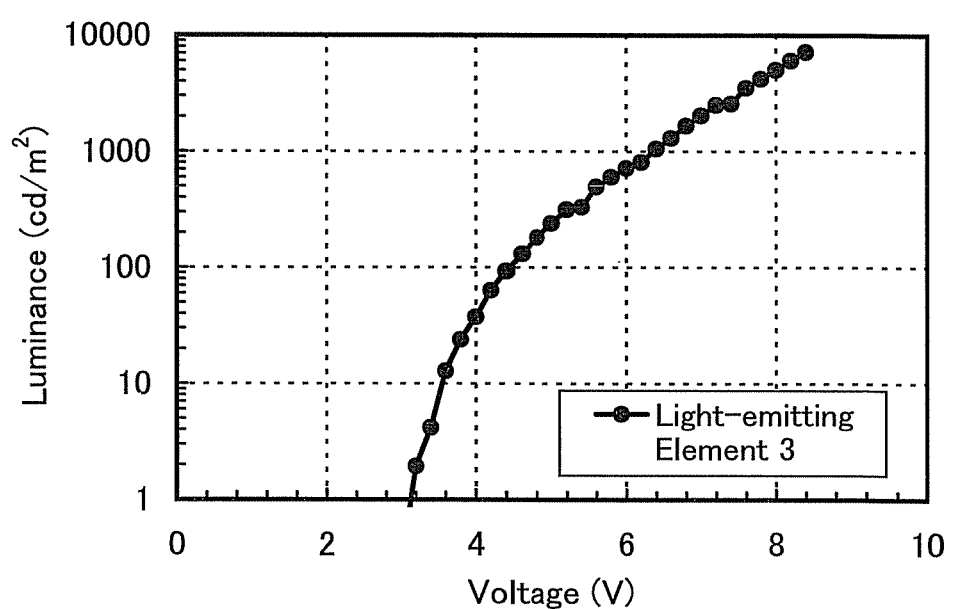
FIG. 24 shows voltage vs. luminance characteristics of Light-emitting Element 3.
Figure 25:
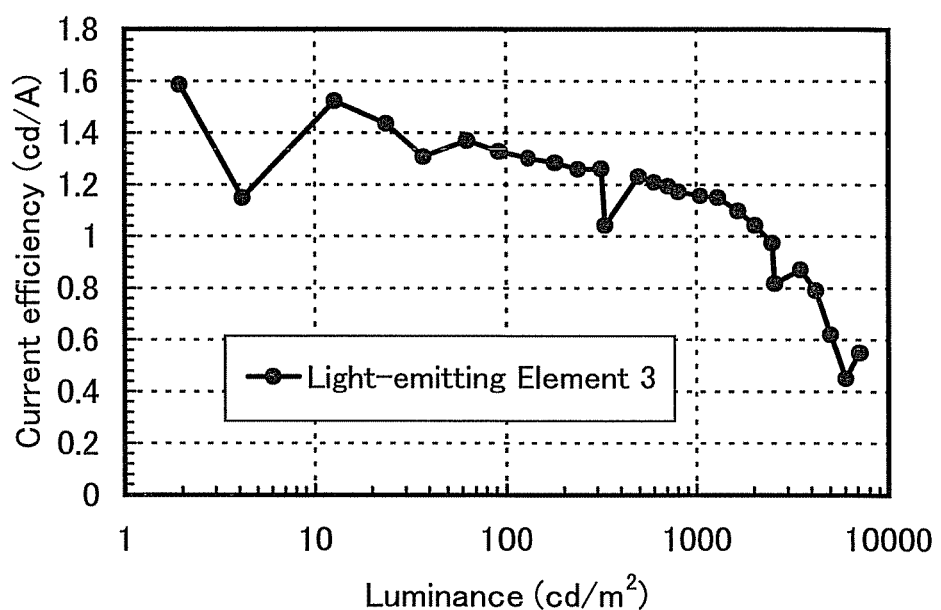
FIG. 25 shows luminance vs. current efficiency characteristics of Light-emitting Element 3.

FIG. 23 shows current density vs. luminance characteristics of Light-emitting Element 3. Note that in FIG. 23, the vertical axis represents luminance (cd/m$^2$) and the horizontal axis represents current density (mA/cm$^2$). Further, FIG. 24 shows voltage vs. luminance characteristics of Light-emitting Element 3. Note that in FIG. 24, the vertical axis represents luminance (cd/m$^2$) and the horizontal axis represents voltage (V). In addition, FIG. 25 shows luminance vs. current efficiency characteristics of Light-emitting Element 3. Note that in FIG. 25, the vertical axis represents current efficiency (cd/A) and the horizontal axis represents luminance (cd/m$^2$).

Note that as can be seen from the operation characteristics shown above, even when the oxadiazole derivative according to one embodiment of the present invention is used for the light-emitting layer of the light-emitting element, this light-emitting element sufficiently functions as a light-emitting element.

Figure 26:
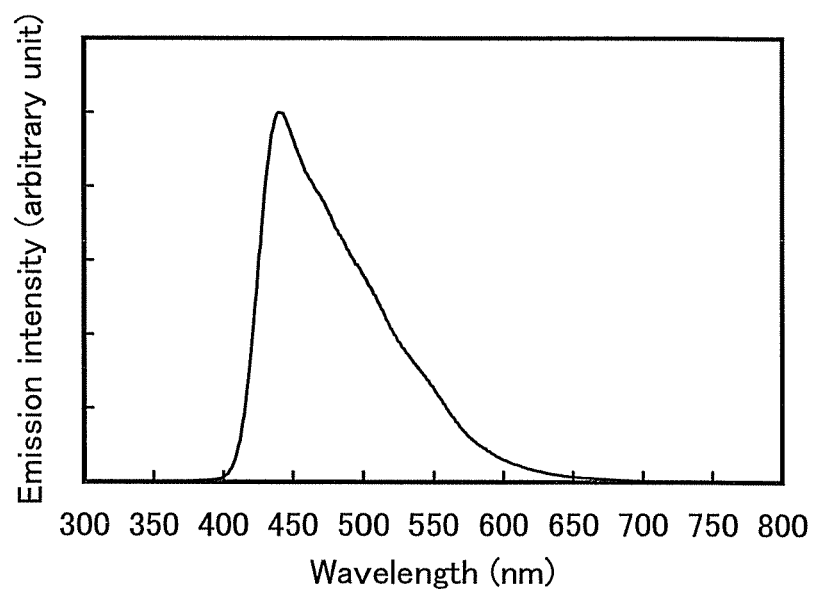
FIG. 26 shows an emission spectrum of Light-emitting Element 3.

FIG. 26 shows the emission spectrum of Light-emitting Element 3 which was obtained by applying a current at a current density of 1 mA/cm$^2$. As apparent from FIG. 26, the emission spectrum of Light-emitting Element 3 has a peak at 445 nm. This indicates that the emission spectrum of Light-emitting Element 3 is exhibited by light emission of O11PhA, which is included in the light-emitting layer 813.

Example 7

In this example, Light-emitting Element 4 was fabricated such that differences in element structure between it and Light-emitting Element 1 described in Example 4 were materials for forming the light-emitting layer 813 and the electron-transport layer 814. In addition, element characteristics of Light-emitting Element 4 were measured. Specifically, CzPA and PCBAPA, which was represented by Structural Formula (vii) shown below, were co-evaporated with the ratio of CzPA to PCBAPA being 1:0.1 (mass ratio); thus, the light-emitting layer 813 was formed. The thickness thereof was 30 nm. As for the electron-transport layer 814, a 30-nm-thick film was formed using PyAO11, which was synthesized in Example 2 and represented by Structural Formula (121). Note that except for the light-emitting layer 813 and the electron-transport layer 814, the structure and formation method of the layers included in Light-emitting Element 4 are the same as those of Light-emitting Element 1, the description of which is found in Example 4 and omitted here. Further, an organic compound used in this example is represented by the following Structural Formula (vii).

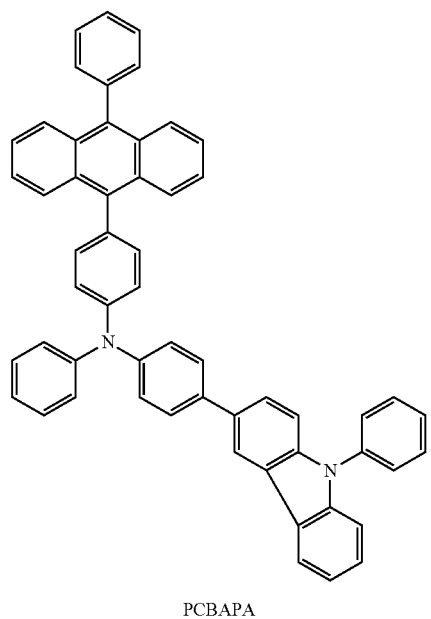

(vii)

PCBAPA

Note that the following Table 4 shows the element structure of Light-emitting Element 4 which was fabricated.

TABLE 4

| | first electrode 801 | hole-injection layer 811 | hole-transport layer 812 | light-emitting layer 813 | electron-transport layer 814 | electron-injection layer 815 | second electrode 803 |
|---|---|---|---|---|---|---|---|
| Light-emitting Element 4 | ITSO 110 nm | NPB:MoOx (4:1) 50 nm | NPB 10 nm | CzPA:PCBAPA (1:0.1) 30 nm | PyAO11 30 nm | LiF 1 nm | Al 200 nm |

<<Operation Characteristics of Light-Emitting Element 4>>

Operation characteristics of the fabricated Light-emitting Element 4 were measured. Note that the measurements were carried out at room temperature (in the atmosphere kept at 25° C.).

Figure 27:
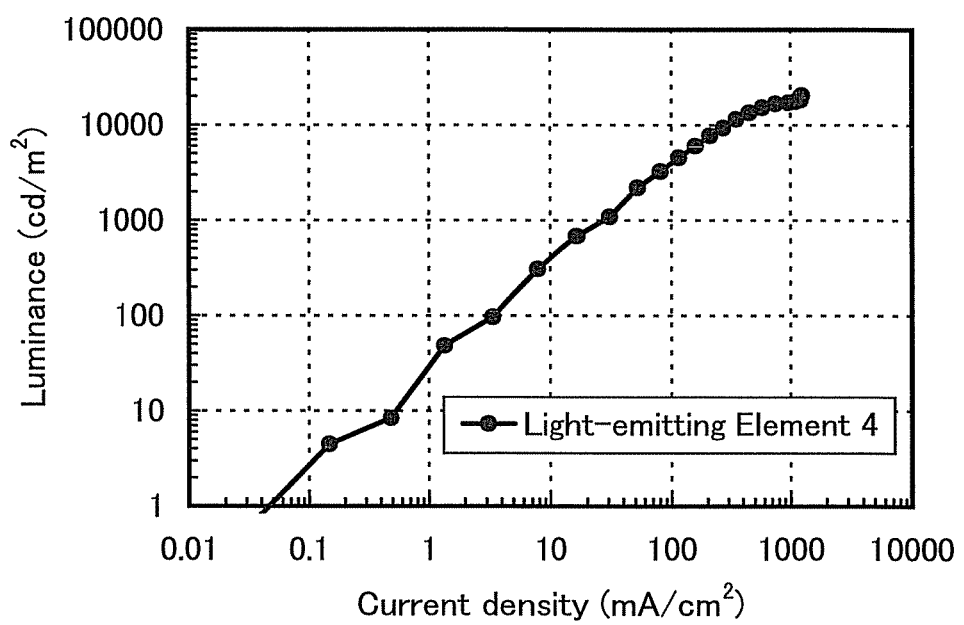
FIG. 27 shows current density vs. luminance characteristics of Light-emitting Element 4.
Figure 28:
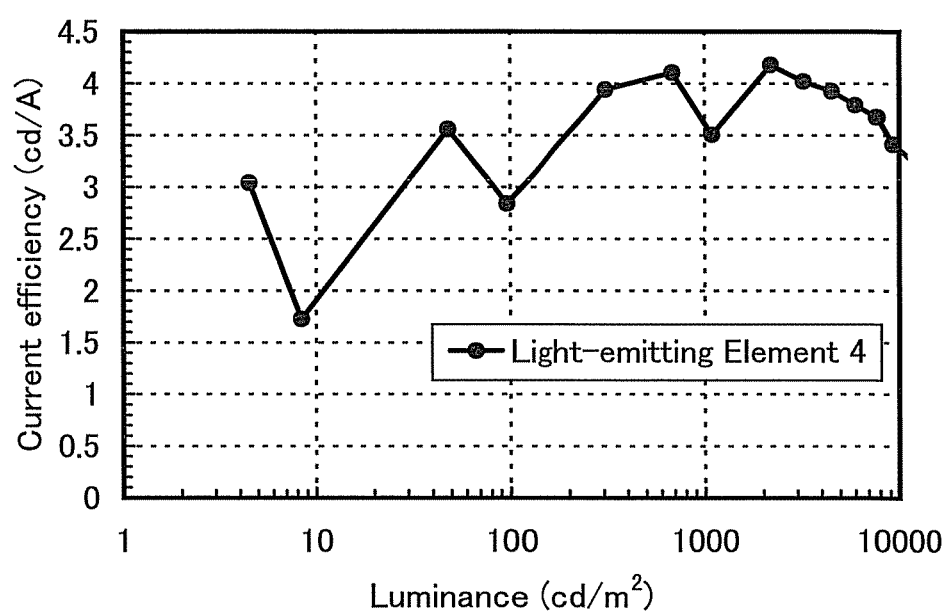
FIG. 28 shows luminance vs. current efficiency characteristics of Light-emitting Element 4.
Figure 29:
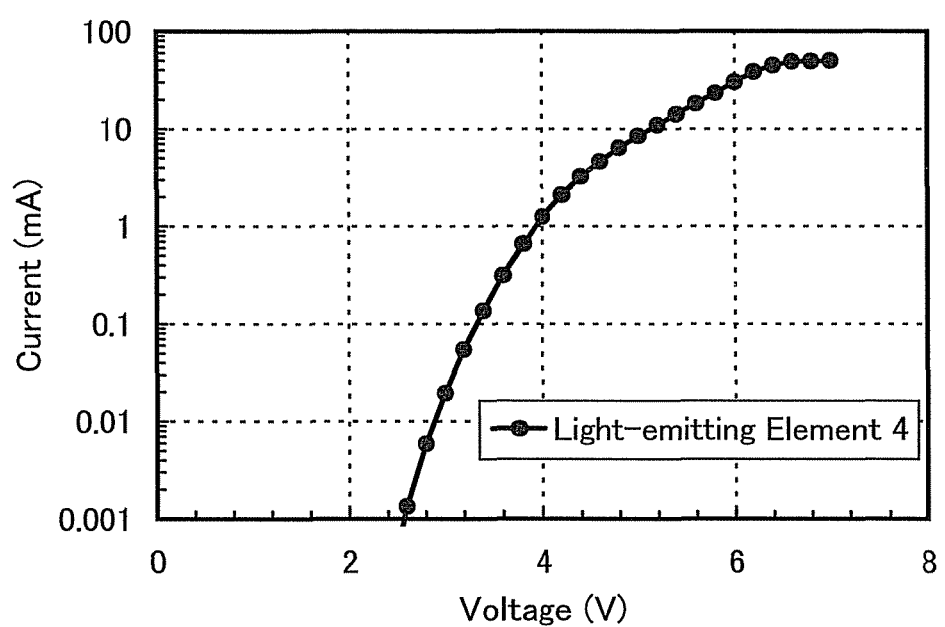
FIG. 29 shows voltage vs. current characteristics of Light-emitting Element 4.

FIG. 27 shows current density vs. luminance characteristics of Light-emitting Element 4. Note that in FIG. 27, the vertical axis represents luminance (cd/m$^2$) and the horizontal axis represents current density (mA/cm$^2$). In addition, FIG. 28 shows luminance vs. current efficiency characteristics of Light-emitting Element 4. Note that in FIG. 28, the vertical axis represents current efficiency (cd/A) and the horizontal axis represents luminance (cd/m$^2$). Further, FIG. 29 shows voltage vs. current characteristics of Light-emitting Element 4. Note that in FIG. 29, the vertical axis represents current (mA) and the horizontal axis represents voltage (V).

Note that as can be seen from FIG. 28, the maximum current efficiency of Light-Emitting Element 4 is 4.2 cd/A. This demonstrates that the light-emitting element formed using the oxadiazole derivative according to one embodiment of the present invention has very high efficiency.

Figure 30:
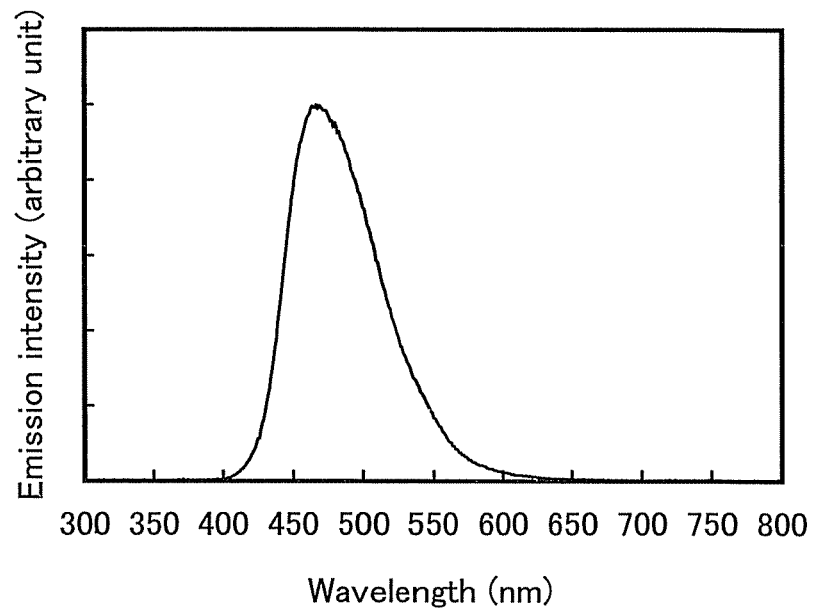
FIG. 30 shows an emission spectrum of Light-emitting Element 4.

FIG. 30 shows the emission spectrum of Light-emitting Element 4 which was obtained by applying a current at a current density of 1 mA/cm$^2$. As apparent from FIG. 30, the emission spectrum of Light-emitting Element 4 has a peak at about 470 nm. This indicates that the emission spectrum of Light-emitting Element 4 is exhibited by light emission of PCBAPA, which is included in the light-emitting layer 813.

This application is based on Japanese Patent Application serial no. 2009-084933 filed with Japan Patent Office on Mar. 31, 2009, the entire contents of which are hereby incorporated by reference.

What is claimed is:

1. An oxadiazole derivative represented by General Formula (G1):

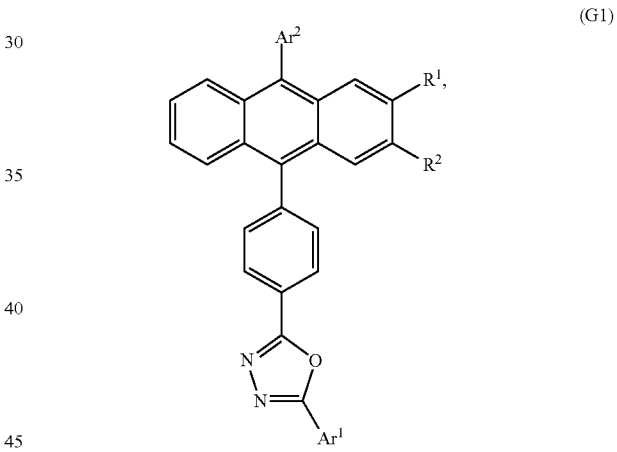

(G1)

wherein:

Ar$^1$ represents a substituted or unsubstituted aryl group having 6 to 10 carbon atoms in a ring;

Ar$^2$ represents an unsubstituted aryl group having 6 to 10 carbon atoms in a ring or an unsubstituted heteroaryl group having 4 to 9 carbon atoms; and R$^1$ and R$^2$ represent a hydrogen atom.

2. An oxadiazole derivative represented by General Formula (G2):

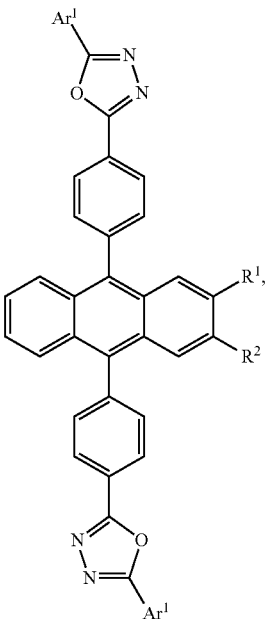

(G2)

wherein:

$Ar^1$ represents a substituted or unsubstituted aryl group having 6 to 10 carbon atoms in a ring; and $R^1$ and $R^2$ represent a hydrogen atom.

3. The oxadiazole derivative according to claim 1, wherein:

the oxadiazole derivative is represented by General Formula (G3):

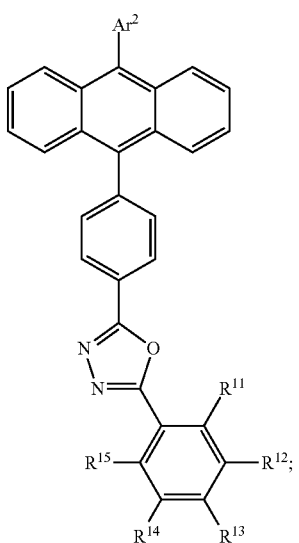

(G3)

and $R^{11}$ to $R^{15}$ independently represent a hydrogen atom, an alkyl group having 1 to 4 carbon atoms, or an aryl group having 6 to 10 carbon atoms in a ring.

4. The oxadiazole derivative according to claim 2, wherein:

the oxadiazole derivative is represented by General Formula (G4):

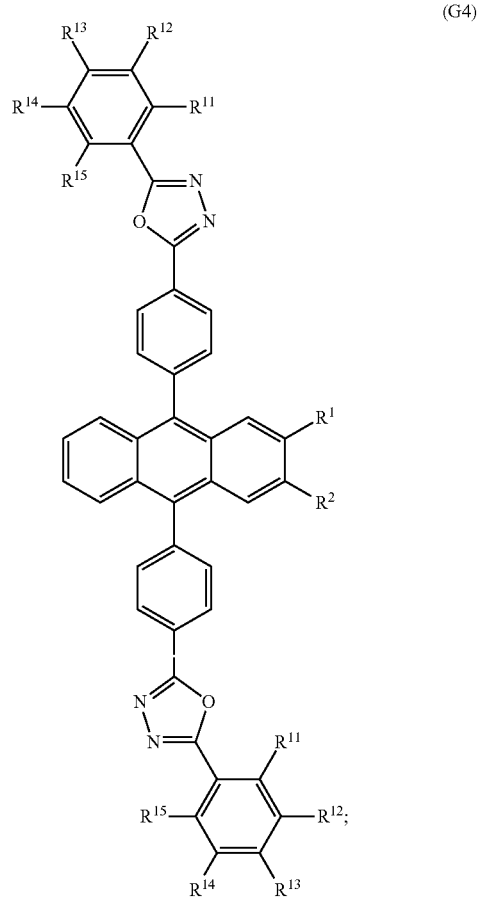

(G4)

and $R^{11}$ to $R^{15}$ independently represent a hydrogen atom, an alkyl group having 1 to 4 carbon atoms, or an aryl group having 6 to 10 carbon atoms in a ring.

5. A light-emitting device comprising:
a pair of electrodes; and
a layer including an oxadiazole derivative represented by General Formula (G1) between the pair of electrodes:

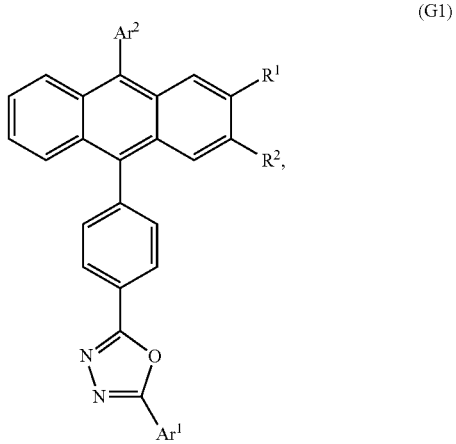

(G1)

wherein:
Ar¹ represents a substituted or unsubstituted aryl group having 6 to 10 carbon atoms in a ring, and when Ar¹ has a substituent, the substituent is an alkyl group having 1 to 4 carbon atoms or an aryl group having 6 to 10 carbon atoms in a ring;
Ar² represents an unsubstituted aryl group having 6 to 10 carbon atoms in a ring or an unsubstituted heteroaryl group having 4 to 9 carbon atoms; and
R¹ and R² represent a hydrogen atom.

6. A light-emitting device comprising:
a pair of electrodes; and
a layer including an wherein the oxadiazole derivative represented by General Formula (G2):

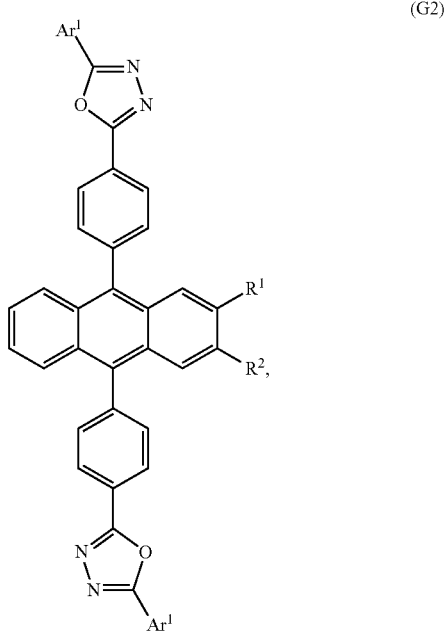

(G2)

wherein:
Ar¹ represents a substituted or unsubstituted aryl group having 6 to 10 carbon atoms in a ring; and
R¹ and R² represent a hydrogen atom.

7. The light-emitting device according to claim 5, wherein:
the oxadiazole derivative is represented by General Formula (G3):

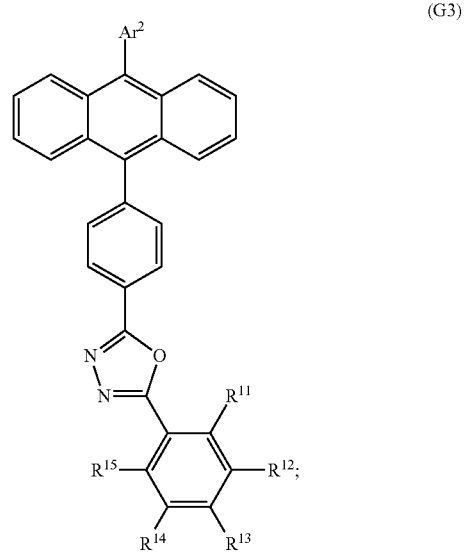

(G3)

and
R¹¹ to R¹⁵ independently represent a hydrogen atom, an alkyl group having 1 to 4 carbon atoms, or an aryl group having 6 to 10 carbon atoms in a ring.

8. The light-emitting device according to claim 6, wherein:
the oxadiazole derivative is represented by General Formula (G4):

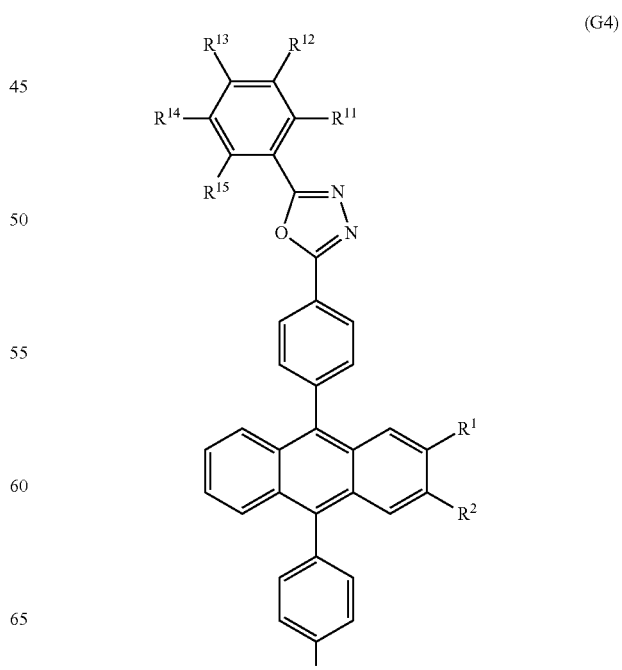

(G4)

-continued

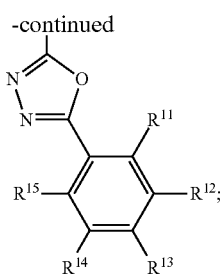

and

R[11] to R[15] independently represent a hydrogen atom, an alkyl group having 1 to 4 carbon atoms, or an aryl group having 6 to 10 carbon atoms in a ring.

9. The light-emitting device according to claim 5, wherein the layer including the oxadiazole derivative is a light-emitting layer.

10. An electronic device comprising the light-emitting device according to claim 5.

11. A lighting device comprising the light-emitting device according to claim 5.

12. The oxadiazole derivative according to claim 1, wherein, when Ar[1] has a substituent, the substituent is an alkyl group having 1 to 4 carbon atoms or an aryl group having 6 to 10 carbon atoms in a ring.

13. The light-emitting device according to claim 5, wherein, when Ar[1] has a substituent, the substituent is an alkyl group having 1 to 4 carbon atoms or an aryl group having 6 to 10 carbon atoms in a ring.

14. The oxadiazole derivative according to claim 1, wherein Ar[2] represents an unsubstituted heteroaryl group having 4 to 9 carbon atoms.

15. The light-emitting device according to claim 5, wherein Ar[2] represents an unsubstituted heteroaryl group having 4 to 9 carbon atoms.

16. The light-emitting device according to claim 5, further comprising a light-emitting layer between the pair of electrodes, wherein the layer including the oxadiazole derivative is an electron-transport layer and in contact with the light-emitting layer.

17. The light-emitting device according to claim 6, wherein the layer including the oxadiazole derivative is a light-emitting layer.

18. An electronic device comprising the light-emitting device according to claim 6.

19. A lighting device comprising the light-emitting device according to claim 6.

20. The light-emitting device according to claim 6, further comprising a light-emitting layer between the pair of electrodes, wherein the layer including the oxadiazole derivative is an electron-transport layer and in contact with the light-emitting layer.

* * * * *